US007074559B2

(12) United States Patent
Kapur et al.

(10) Patent No.: US 7,074,559 B2
(45) Date of Patent: Jul. 11, 2006

(54) MYCOBACTERIAL DIAGNOSTICS

(75) Inventors: Vivek Kapur, Shoreview, MN (US);
John P. Bannantine, Ames, IA (US);
Ling-Ling Li, Moundsview, MN (US);
Qing Zhang, Seattle, WA (US);
Alongkorn Amonsin, Lopburi (TH)

(73) Assignees: Refents of the University of Minnesota, Minneapolis, MN (US); The Unites States of America as represented by the Secretary of Agriculture, Washington, DC (US)

( * ) Notice: Subject to any disclaimer, the term of this patent is extended or adjusted under 35 U.S.C. 154(b) by 179 days.

(21) Appl. No.: 10/137,113

(22) Filed: Apr. 30, 2002

(65) Prior Publication Data
US 2003/0175725 A1  Sep. 18, 2003

Related U.S. Application Data

(60) Provisional application No. 60/362,396, filed on Mar. 6, 2002.

(51) Int. Cl.
C12Q 1/68 (2006.01)
G01N 1/30 (2006.01)
C07H 21/04 (2006.01)
(52) U.S. Cl. ............... 435/6; 435/4; 435/40.5; 435/243; 435/253.1; 435/320.1; 536/23.1; 536/23.7; 536/24.3; 536/24.32
(58) Field of Classification Search ............ 435/4, 435/6, 40.5, 41, 243, 253.1, 320.1; 536/23.1, 536/23.7, 24.3, 24.32
See application file for complete search history.

(56) References Cited

U.S. PATENT DOCUMENTS

| 4,918,178 A | * | 4/1990 | Hurley et al. ............... 536/23.7 |
| 5,314,801 A | | 5/1994 | Nycz et al. |
| 5,504,005 A | | 4/1996 | Bloom et al. |
| 5,589,585 A | | 12/1996 | Mabilat et al. |
| 5,849,901 A | | 12/1998 | Mabilat et al. |
| 5,968,815 A | | 10/1999 | Murray et al. |
| 5,985,576 A | | 11/1999 | Ellingson et al. |
| 6,387,372 B1 | | 5/2002 | Cocito et al. |

OTHER PUBLICATIONS

GenBank Accession No. AF445420.
GenBank Accession No. AF445421.
GenBank Accession No. AF445422.
GenBank Accession No. AF445423.
GenBank Accession No. AF445424.
GenBank Accession No. AF445425.
GenBank Accession No. AF 445426.
GenBank Accession No. AF445427.
GenBank Accession No. AF445428.
GenBank Accession No. AF445429.
GenBank Accession No. AF445430.
GenBank Accession No. AF445431.
GenBank Accession No. AF445432.
GenBank Accession No. AF445433.
GenBank Accession No. AF445434.
GenBank Accession No. AF445435.
GenBank Accession No. AF445436.
GenBank Accession No. AF445437.
GenBank Accession No. AF445438.
GenBank Accession No. AF445439.
GenBank Accession No. AF445440.
GenBank Accession No. AF445441.
GenBank Accession No. AF445442.
GenBank Accession No. AF445443.
GenBank Accession No. AF445444.
GenBank Accession No. AF445445.
GenBank Accession No. AF445446.
Bannantine et al., "Identification of *Mycobacterium paratuberculosis* gene expression signals," *Microbiology*, 1997, 143:921-928.
Bannantine and Stabel, "HspX is present within *Mycobacterium paratuberculosis*-infected macrophages and is recognized by sera from some infected cattle," *Vet. Microbiol.*, 2000, 76:343-358.
Bannantine and Stabel, "Identification of two *Mycobacterium avium* subspecies *paratuberculosis* gene products differentially recognised by sera from rabbits immunised with live mycobacteria but not heat-killed mycobacteria," *J. Med. Microbiol.*, 2001, 50:795-804.
Bannantine et al., "Genome Scale Comparison of *Mycobacterium avium* subsp. *paratuberculosis* with *Mycobacterium avium* subsp. *avium* Reveals Potential Diagnostic Sequences," *J. Clin. Microbiol.*, 2002, 40(4):1303-1310.
Brosch et al., "Comparative genomics of the mycobacteria," *Int. J. Med. Microbiol.*, 2000, 290:143-152.
Cole et al., "Deciphering the biology of *Mycobacterium tuberculosis* from the complete genome sequence," *Nature*, 1998, 393:537-544.
Collins and Sockett, "Accuracy and economics of the USDA-licensed enzyme-linked immunosorbent assay for bovine paratuberculosis," *J. Am. Vet. Med. Assoc.*, 1993, 203(10):1456-1463.

(Continued)

*Primary Examiner*—Rodney P Swartz
(74) *Attorney, Agent, or Firm*—Fish & Richardson P.C.

(57) ABSTRACT

The present invention provides nucleic acid molecules unique to *M. paratuberculosis*. The invention also provides the polypeptides encoded by the *M. paratuberculosis*-specific nucleic acid molecules of the invention, and antibodies having specific binding affinity for the polypeptides encoded by the *M. paratuberculosis*-specific nucleic acid molecules. The invention further provides for methods of detecting *M. paratuberculosis* in a sample using nucleic acid molecules, polypeptides, and antibodies of the invention. The invention additionally provides methods of preventing a *M. paratuberculosis* infection in an animal.

43 Claims, 13 Drawing Sheets

OTHER PUBLICATIONS

Cousins et al., "Mycobacteria distinct from *Mycobacterium avium* subsp. *paratuberculosis* isolated from the faeces of ruminants possess IS*900*-like sequences detectable by IS*900* polymerase chain reaction: implications for diagnosis," *Mol. Cell. Probes*, 1999, 14:431-442.

Dubash et al., "Evaluation of an enzyme-linked immunosorbent assay licensed by the USDA for use in cattle for diagnosis of ovine paratuberculosis," *J. Vet. Diagn. Invest.*, 1995, 7:347-351.

Ellingson et al., "Identification of a gene unique to *Mycobacterium avium* subspecies *paratuberculosis* and application to diagnosis of paratuberculosis," *Mol. Cell. Probes*, 1998, 12:133-142.

Ellingson et al., "Evaluation of the accuracy and reproducibility of a practical PCR panel assay for rapid detection and differentiation of *Mycobacterium avium* subspecies," *Mol. Cell. Probes*, 2000, 14:153-161.

Eriks et al., "Rapid Differentiation of *Mycobacterium avium* and *M. paratuberculosis* by PCR and Restriction Enzyme Analysis," *J. Clin. Microbiol.*, 1996, 34(3):734-737.

Harris and Barletta, "*Mycobacterium avium* subsp. *paratuberculosis* in Veterinary Medicine," *Clin. Microbiol. Rev.*, 2001, 14(3):489-512.

Mahairas et al., "Molecular Analysis of Genetic Differences between *Mycobacterium bovis* BCG and Virulent *M. bovis*," *J. Bacteriol.*, 1996, 178(5):1274-1282.

May et al., "Complete genomic sequence of *Pasteurella multocida*, Pm70," *Proc. Natl. Acad. Sci. USA*, 2001, 98(6):3460-3465.

Stabel et al., "Comparison of polyclonal antibodies to three different preparations of *Mycobacterium paratuberculosis* in immunohistochemical diagnosis of Johne's disease in cattle," *J. Vet. Diagn. Invest.*, 1996, 8:469-473.

Stabel and Whitlock, "An evaluation of a modified interferon-γ assay for the detection of paratuberculosis in dairy herds," *Vet. Immunol. Immunopathol.*, 2001, 79:69-81.

Whipple et al., "Isolation and Analysis of Restriction Endonuclease Digestive Patterns of Chromosomal DNA from *Mycobacterium paratuberculosis* and Other *Mycobacterium* Species," *J. Clin. Microbiol.*, 1987, 25(8):1511-1515.

Marsh et al., "Quality control and optimized procedure of hybridization capture-PCR for the identification of *Mycobacterium avium* subsp. *paratuberculosis* in faeces," *Mol. Cell. Probes*, 2000, 14:219-232.

* cited by examiner

Gene 10 (SEQ ID NO:1)
GTGCGCCCGCACACCGGCGGACGGCGGATCAGCATCTACTGGACGTGGAGCTATCCGTGGGAATCGCAGCG
CGACATTCAGACCCTGGACAACCGCTTCTCCACCATGACCGAAGTGCGCAGGGCGGCCTGGCCCCGATACG
AGGGGCCCGACTGGGACGACGCCCACTTTCTGCAGGGCATCGCCGGCACCTTGGAGCTTTTCCACCGCTCG
ACGCTTGCGTTCCAGGAGCTGGCCGGCGAAGCAACCGGTCAGCAGGTGGCGGTGTTCCAGCGCGTCGACCA
GGCCGGCTACCGGCTGGTGATCGACGAGCGGATATTGGCCGACACCGACACCCTGATGGTGTTCGGGCTGG
ACCATCTCGCCGGGGAAGACGAGGCCGAGCCCGGGGAGATCTCGGCCATCCGTGCCTGGCTGGAACGCGAG
GGCACCTGCCTGCTGCTGGCCCCGCACCACGACGTCGGCGGCACCGACGACATGGCCCAGCGGCAGGTCGA
ATACCTGCACCACGGGGATCCGCTCGTGCCGCGGCAACAACGGTTTTCCGCCTACACCCGCTCGCTGATGA
AGGGGGCTCGACGTTCCCGTCCGCAACAGGTGGGGCCTGCATCCGGCCCGGGTGGCCGCGACCGGTCAGATG
GCACCGCTGACCTGCTTTCGCGACCTGGACGCGCCCGGGCTGCTGGACGATGTCACGACGCTGAACTTTCA
CCCGCATCTGCCGCACTACGAGCTCACCGCCCCGGAAAGCGACGGGCTACGGGTGCTGGCCACCCAACGCG
TCGACCCGGCCCGGCCCCATCCCTTTACCGAGGCGGGCAACAGCGAATTCAACGCGTTGATCTGGATGCCG
CCGCACGCCGAACGAGCCGGTGACATCGTGCTCGTCGACTCGACCAACTTCACGACGCTGTTCGGCGGGTC
CGACAGCCTCAGAAACTTCTGGCACAACCTGGCCACGATGAGGTGA Gene 11 (SEQ ID NO:2)
ATGGTGGCAACCGAACACGAGTGGAGCAAACCCGCGGCCCTGGCCATTCCCAGGGAGGGCTACTTCGAGCT
CGAACGCGGTCGTTACGGGCCGCTGTATCCCCGCACCCCGGCCTGCTACGGCTTTTCCATCATCGCCAAGG
TCAAGGAGGGCCGCGAGGAAGCCGTCCGCGCCTACGGCAAACAGATCGAAGAGGCCATCAAGGCCGATCCG
CACGTGCTTGCCGCGCTGCGGCTGCACTACCTGCGCTGGTTGCTCTTCGACGTCGGATCGGGACTGCACTT
CCAGTACCAGGGCATCTTCGACACGGACTTCGACAAGTACACCGAGGACGCGGTGCAGCTGTTCAGTCAGA
CCGGGATCACCACCGTCTTCACGAACCTCGAGGGGTTTCCCGAAGACTGGCGGGAGAACCCGGACGCCTTC
GTCAAGTTCGTGCGTGAGCACCAGTGCCCGAGCTTTCTGGAGTACGGGGAGTATCCCTACGTCACCGCCGA
CGAGATCAAAAAGGCGTACGGCTCAAGCCGCCTCCCAGACCATGCTGGATCAGATGCAATGACGTCGGTCA
GAGTCTGA Gene 38 (SEQ ID NO:3)
ATGGTGGTAAGCATTTCGGCTCCCACGGTGCCGATACCCCAGGCGATGACGTTCAGCGGTCTGCGGTCAGA
CATCGGACAGAAGCCGACGCGTGGGCAGCACCGTCAACGGGACGCCGCGATCTTCGAACTGCCAGTTCGGC
CCATGAGAGATGTAGGTCATTTCGACTTCCTCCCCGCGCTTCGCTTCGGTGTCCGACCACCGGATGTCGAC
GACCAGGTCGCTGGCCTCGTAGGTCGCGTGCAGATCCGACCAGTGCGGATCGACACCGGTGGCCATGACCT
CGAGGGGACTGACATCGTGCGTCGACAGCGTCGCCATCCAACTGCGGTCGCGGACGGCGGGGAGTTGCTT
GGGATGCGCACCCGCACCGCGTCGCGCGCTCCTGTCCCGAGGCGCTCCACGGATGCTCCGGTGTAGGCGAA
CGGGCGCAGGGCGGGATGCAAATCGAGGACCGAAGCAAGGTCATCTGCGCCGACGCCAAACCCGAGGCTGC
TTTGATGCGCGCCGAACCGACGTAG Gene 56 (SEQ ID NO:4)
ATGAACACTTCTTCCTCTCTACCTGTCGACACCCTGGACGTCACCGCACCACCGGATGCCACTGAGGTTTA
CGGCTGGGCAGCGCACCCAGACCGTCTGGCCGCCCGTGCATTCGAAGCAGCGGTGCGTGACTGCGCCGGCT
ACCGGGTCCGGGTGCGCGGTGCGCAACGCTCCAACGTCACCTGCCGCCGCTGGGTGGCCATCGAAGCCGCA
CCCGGCGCCGACGAGCAAGCGTTGGAGCCCGAAGCGGTGCGGCAGCTGGCGCCGCAGATGAGCGTCACGCC
TACCACGCGCCGGACAGCTGAGATGCTCGACGACGCCGCCTTCGATGCGATCGTCGCGGTGTTCAGTCAAC
GGGCCCGATGCGAGATGCAAACGCTGTCGGGAGGCAAGTGCCCACGGGCTGCGCGCTGGCGCATTGATTTG
CACGGGTGCGAACAGGCCATTGTGTGCGGGCAGCACAAGAAAGCGTGGCTGCAGGAGGCCCTAGCCAACCT
CTGGCGCGGCATTCAACCTCGCTGCCCCACTGCGGAAGAGTGTTCAACAGCTTCCAAGACGCGGTCAGGA
TCACCGCGATATGA Gene 57 (SEQ ID NO:5)
ATGGCCACCAACGACGACCAAGACGACGGGAAGCCACCCATTACCGCGGCCGCTGGCGGTGATGAGACCGC
GATCGGGGCGGCCGCTGATGAAACCGAGCTCGTCGCGCCGCTCACCGTGCCCGCGTCCGAGTTGGCCTGCT
CCCACGAGGACAGCGACGCTGGTGATTACTCGTGGGGCCGGGCTCCGGAACGCGCCAGCATCATCGTGCTC
GCCTGTGCGGCGGTCGCTGTCGTGATCGGTTTGCTGACCTGGCTCGCCTTGCACCTACACGACCAGGCCAA
GCCGACAGCCGGCCCGACGGCCGCGCG

Figure 2-1

```
Gene 128 (SEQ ID NO:6)
ATGAGCGCCAGGGATCTCATCAACATCGGGGTCTTCGGCGCTCTCTACATCGCCACTGTGTTCGCGATCAA
CGTGTTCGCTTTCATCAATCCGCTCGTCATGTTGGTCGCCCTGGCGGTCAGCATGATCGCCGGCGGCGTGC
CGTTCATGTTGTTCCTCACCCGGGTGCGACATGCGGGCATGGTGACGGTGTTTGCGATTATCACGGCCGGA
CTGCTCGCACTGACCGGGCACCCCCCGATCTGCTTCGTGATCACAGTTGCGTGCGCGTTGGTGGCCGAAGT
CGTCCTGTGGCTGGGACGCTATCGCTCCCGCACCATGGGTGTACTGGCGTACGCAATCTACGCGGCGTGGT
ACATCGGCCGCTGCTGCCCATCTTCTACGCTCGCGATGAATATTTCTCCAGTCCCGGCATGGCACAGATG
GGTCCGCGCTACCTCGAAGAGATGGAACGGTTGTTGTCGCCAGCCGTGCTAATCGCATTCGACCTGTCCAC
GGTGGTATTCGGGCTGATCGGCGGACTGCTCGGAGTAAGGTTGCTGCGCAAGCATTTTCAGAGGGCCGGCC
TAGCTTGA Gene 135 (SEQ ID NO:7)
ATGGCGGGGATGCCGGAGGAGGTCGCTGCGCTTCTGCGCGGTTTCCCACGCATCGGCGCGCGCGAGCAGGC
GTTTGCGTTCTTGACCGTTGACACTGGCGGGTTTCCACATGCGGCGTTGCTGTCGCGCTGCGAGCTCGAGC
CTGGGCGGGACCCCCAAACACTGATGGCCGCCATAGCTAGCCGACAGACCCGCGCCAACTTGCGGCGTAGC
GGCACCGCGGGGCTGCTCGCAATCAATGGCACTAGTTGCCACCACCTCAAGCTGCGAGTGGTCGCCTCGCT
CGTCGGTCGCGGAATACTCGGATGTGTGTTTGCCGTGACCGAACATAAGCGCGATGACATGGGAATACCCT
TGCAGCCTACGCTATTTCGGACCTCGGCCGAGATCTCGGTGCTTGAGGACTGGCCGCGTAGTCGGGCCATG
TTCGACCGTCTCGCAGCGCTGCGCAGCGCAGCGCGGGAGGTCCTATGA Gene 159 (SEQ ID NO:8)
ATGCGTTTCGCCCTCCCGACGCGCATCCTGCACTGGCTGATGGCGCCGATGGTCATCGGGCAGCTGCTCAT
CGGGGTGGTCATGATCACCTCGTTGACCTACTATCCGCTGCTGCTGGCCATCCACCGGCCGTTGGGCGCCT
TGATCCTGGCGTTTGCGGTGGTGCGCCTGGCGAACCGGTTCACCCACCGGCTGCCGCCCTTCCTTGCCACG
ATGGGCCCCGTCGAACGCCGCGTCGCGACATGGTCGGAGTACCTGCTCTATGCCCTGCTGCTAGCCCAGCC
CTTGATCGGGTGGGCGATGCTGTCGGCGGCGCGGTTCCCGGTCGTCTTGGTGGGACCCGTGCATCTGCCCG
GCATCGCACCGCACAACGTCGACGTCTATGCGGCGCTGCGCCAAGCCCACAACGTCGGCGCCTTCCTGCTT
TTCCTGACCTTCACGGCCCACGTCTGCGCGGTCCTCTTTCATACGCTCGGCCTGCGCGACCGGCTCCTCGA
TCGCATGGCGCTGTGGCCCACCAAGCCCGTCGCCTCGCGGCAGGACGAAATCAAGGCGTGA Gene 217 (SEQ ID NO:9)
CTGCGCAGGCTGATGGCCGAACGCGGACTGTTCAACACGACAGCGTTGCGGCCACTGCTGGCCGAACGCGG
GGTGCAGCTGTCGGCCAGCCAGGTCTACCGGCTCGTGACCGAGAAACCGGAACGGTTGAGCCTGCCCACCC
TGGTGGCACTGGTGGACATTTTGAGGTGTGCGATGGACGAGTTGATCGAGATCGTGCCCGCCACAGCTGCC
TCGGCGAAGAAGGCCGCGGGCGCACCGGAGCGCAGCAAACCGGTCAGGACGCGGGAACTTGGTGGCCACCG
CCCCGTCCGGGCCAAGATCGTCGACGCGGATTCCTAG Gene 218 (SEQ ID NO:10)
ATGCGCGGAAACCGCAGCGAGTTCGTGACGGTGATCGTCACTGCAGTGGGCGCGATCGAGCCGCACCTGAG
CCACGACGATGTCCGCACCGCGATCGAGGGGATGGGCCTGTCGGCCGCGCAGTTGCAGAGGCTGTCTAGAA
CGCTGCGGCGCGACGGTAGCGTGCTCACCGGCCCGGCGGCAGCGACTGCGCCGCCGACATCGAGCAGCTG
ATCCTGTGTCTGCGCCAACTCGGCGCCATGCGTGTTCGAGCGCCGCGGTGTGCCCAGTGCGGCCGCAACGA
TTCCGAAACCTACTCGCGCAAGCTCAAGAAGCGCATCTGCCGAGCCTGTTCGATGCAGGGTTGGCAGCCGG
CTGTCGGTGAATGCCCGGGCTGCGGCGCGGTGGACAAGTTGATCTACCGGCCGCGGCACGGCGATGGCCTG
TTGTGTCGGAGGTGCAAGCCCGAACCCGACGTCGATCACGCCGCCAAGGTTCGTGACGGTATCGCGCAACT
GCGGACCGGGCTTTCGGCCACCGAGATTGACCGGGTGGCGTCGGTGTTCGGCACGGCGGTCGCGCAGCGCG
AGCTTAACTGGATCTTGCAGGACACCCCGGAGTGTTTCGCGGTGAGATCGCCCACCGCTCGGCGGTCTCG
GTGCGGCTCGCCGAACTACTTGTCGCTGCCGGTGCCGACAATGTGCGCCTTCCGCAGTGCCCGTTGTGTTT
GCGCACCGTGAAGCTCGGCAGCCAGATTGACGGGTTCGCTGCTGCCATACCTGCTGGGGTCACCACTTCA
GCCGCGGCACCTGCGCTCGTTGCGGTTGCCAGCGTCACCTTATCAATTATCACGGTGCCGGCGAGCGCCTC
TGTCACCGTTGTTTCGAGCATGATCCGGTCAATCATGAGCCGTGTACACGGTGCGGTCGTGTGGACTTCAT
CAACCACCATGACGGCCAAGCGAAGCTCTGCCGGCGCTGCTACCCGGCACCCACCGCGGTCTGCAGCTCGT
GCGGACGTACTCGCCCATGCACCCGCACCCGGACGGGAAAGCCGATCTGCGGCACCTGCTCGGCCAAACAG
CGCCCACCCCAACCCTGTTCGGTATGCGGCAACATCCGCTCCGTGCACACCCGGACTGACGCCGGTGAGCC
```

Figure 2-2

```
GGTGTGTAACCCGTGCGCACGAAGTCGGGAACCGTGCGCCCGGTGCGGCAAAACGCTGGGGGTCTCGGCGC
GGCTTGCCGGGGTCGGGCCGCTGTGCTCGGCCTGCCTGCAACGTGAACCCGCCTATTTCACCGACTGTGTG
CAATGCGGCGCCCATGGACGGACGTACCACCGTGGGCTGTGCCCGGCCTGCGCCTGTCCCGGTGAGCTCCG
CGAATTGTTCGCCAAGAACGGCGAATTGAGCGGCGCCGCCAGCCGCATCGTCGAGGCGTTGCTGCAATGTG
ACGCCATGCCGGTGCTGCGATGGGTCAGACGCATGCGATCGAACAGTGAACTGCCCGCGCAGCTCGCCGAA
CTCGGCGACACCCTCAGCCACCACGACCTCGATGACCTCCCGGCCAGCAAATCCGTGGAATGGCTTCGCAA
CATCCTGGTGACCGCCGAGGGTCTGCCAGACCGCGACCCCTATCTGCACCGCACCGAGCAGTACATCGCCG
CCCGGCTGGCCACCATCAGCAACCGCGACGATCGCGCGGCCGTCCGCGCATTCACCGAATGGAATCATTTG
CGTAAACTCCGGGCCCGCGCCGACAAAGGACCACTCAAACGCAACCACGGCCTCGCCGCCCAGATCATGGC
CGCCGCCATCACCGACTTCGTCTCCGAACTCAACGCGCACGGACTGGCCTTGGCCTCATGCCAGCAGGCGT
TCGTCGACGACTGGTTGGTGCGCAACCCCACTCGCCGCCAGATCCACCAATTCCTCGCCTGGGCGGTCCAC
CGTGGCTACGCCCACGACGTCGCGGCTCCCGTACCGCAAACCCGCCGCACCCGCCACACCCTGCCCGGCGA
CGACGAACGATGGCGCCTGATCCAATACCTGATCGAACACCCCGACTTGGAGACGCGCGATCGGGTCGCCG
GGCTGCTCGTGCTGCTCTACAGCCAACCCGCCGCCCGCCTGGTCACCCTCAAGGTTGCCGACGTCACCATC
ACCGACGACGCGGTCCAACTCACCCTCGGCGCCGTCCCGCTCACCGTGCCCAGCCCCGTCGACCGCCTGCT
CGCCGATCTCGTACAGCAGCGCCGCGGATACGCCGCGGTCACCGTGGCCACCAATCCATGGCTGTTTCCCG
GAGGACGCTCCGGTGGGCACCTGTCCGCCAACCAAGTGGGGCTGCGGCTCAAACGAATTGGCATCTCCCCC
CGGATCGCCCGCAACACCGCGCTGATCGACCTCGCCGGCGAACTGCCCGCTGTCGTGCTCGCCAAACTCCT
CGGCTTCAGCATCAAACGCGCCGTCACCTGGAGCGAAGAAGCCGGCAACACTCGCCCCCGCTACGCCGCCG
AGGTCGCCCGCCGCAACTCGTGA

Gene 219 (SEQ ID NO:11)
GTGTCAACATCTACTGAGCGCCGTTTGCGCTTACAGGTCGCCGTTCACGAGAGCTGGGCGCGCACCGAAAA
CCGTTCCGCGCAACGCATAACGCCCGTAAGGCGGCATGGGACCGCTTCGAAAAGCAGGTCGATCCCGAGG
GCAAGCTACCCCCGCCCTGCGCGCCAAGATGGCCGAGAACGCCCGCGCGGCCCACTTCAAGAAGATGGCG
TTGAAGTCCGTCGAGTCCCGGCGCCGTCGCCGGGACGGGGTGGCGGCGTGA Gene 228 (SEQ ID NO:12)
GTGCCATACGCCGAATCGCCCAGGACCCGCACCGGGGGTGTGTTCACCCTCGAGCAGGCTCAGCCCGACGA
CGGCCTCGTGGTTGTCCGCGCCGCTGGCCTTGGTCAACGCGCAATCGGTGATGATTCCGGTGTCGGGCTCG
ACGGCAAGGTGGGCTTTGAAGCCGTCCTGGCGGCGGTGCACCGTCTTGTGAGCGTGCCGCGTGTCGGCATC
GACGGTGGAGATCACGCGATCCCCACTGACCTGCTGCGCGATGCGCCAGTGCCCGTCGGTGCCATCAGAGC
CCTCGACCGGTTCAACGTCTTGACCGGCGATCAACGCCAACAACGCCACCGCCTCAGCAGCCCGCGGCGCG
AGTTCCTGGTCAGGCAGATAGCCCAGCACCCGGTGAGCATCACCGACCAAACCATCCACCAGCCGATCCCG
AGCGGCCTTATCCTCCCACGCAATCGCGGGTTTCCCCGGATCGTCGTAATCATGGGCGCTGCAGTGGGCTT
CGATCACCGCTGCAGCGCCAGGGACTTCGCGGCGCACTCGTCGGATCGCGGCGATCAACTGCGTCACGGTG
TCCTGCGTGGCCACCGCATCGTCGAGCACCGTGGAATCCAAGGCCCGCCGTGTCTTGCCCGCCAACACCCC
GGTCTCGGCCACCACCGTCTTGACCGCCTCGAAGATCCGGTTGGGCCGATCCGAAGCCGCCAACCGACGCC
GCCAATACGTCAACGTCGTCGAATGAAACGCGCCCGCCGTGATCGGCAACCCGCACGCTGCTTTCCAGCGC
AGATCGAAAGTCACCGCATCCACGGTCTCGTTATCCGAAAAACCGTGCAGGGCCTGCAAGGTGATCACCGA
GGCCATCACCTCAGCCGGCACGCTGGGCCGGCCCGCTGCGACGGGAACAAGTCCGCGAACATCTCCTCGG
GAAACAACTGGCTGCGGTGCGCCGCCAGGAACGCAAACATGCTGTCGGCCTTCAGAAGATGCCCGGCAACC
GACTCCGCATCCAACAACTCACGCTGATCATCAGAGCGACCCTGCACCCAACAATCATCCCCAAAACCCCA
GGACAACTCGTCCCGCCACGCGGAATTAATTCAGCAGGCTCCTAG Gene 240 (SEQ ID NO:13)
TTGGTCATTGCGCTAGCTGCCTTGTGGAGCATCCGTTTGGCCTGGCACATCCCGTTCGAGCGAGCAGCAGT
GTTGGCACTGGCGTTTATGTGTGCCCAGTTGGTCCTGGCGCTCGGGCCGGTGGACGGGTGGCTGAGCCCAT
TGCTCCACGACATGACGGGCGTGTGGAACCTCGAAGACCTCATCGGCCATCTGCTCTACGTGTACGGCTTG
TTCTCGATCATGTATCTGGTCGCTGACCACTGCGACATGACGCCGGTCAGCTCAGGTGGTTCGTTCGGAA
CCGGTTGGAACTGCCGTCGGTCGTCATCTGCGCCGTCATGATCGCGGTCTTCGTCGCAGGCGACATCGGCG
AGACCTGTGTTCCCGATGTTGTGGCCACAGAACACACGCCCTGGCTCCGCGTCTACTGGTTCGTAATGATC
GCGGCTCTTGCGTACATCATTGTCTCTACCGGTCGAATCCTGTTGATCCTGAGGCAGCACCCACGCTCGAG
GCATGCCGCCACGGCCTATCTCGTAGCGCTCGGTATCACTGGCGCGTGCTGCGTGGTTTTCATCATCGGAA
```

Figure 2-3

TCCCTTGGCTGCAATGGCTTCTCGTGCGGTGCGAGGTAGTCGGCTATGCGGTGGCCGCCTCGTACTCCTGG
CGTAACAAAGTGGCTTACTTTCGTGGACGCTAG

Gene 241 (SEQ ID NO:14)
TTGCACGAAATCCTCCGGTTTGGCGGGAAAACCGACGAATTGATCGGTTTTGCCCGCGCTTTGTCGGTTCA
GACTGCTACCCTGCCGGGCATGTCTTCGCATTCGCCTGTGTCGGCCGCCGCCCTGGCCAGCCGATTGCGGA
TGATCATGGGCGACCGCAAGCTGTCCCGTACCCGTCTTTCTCACGAGACAGGTATCAGCCGCCCGAGCCTT
TCTAGCAAGCTCGATGGCAAGGTCGAGTTCACCTACAGTGAGCTACTTACGATCGCCCAGGCGGTCGATGT
TCCGCTGGACAAGCTGCTCGCCGGAGACGACGATGAGCGGCCCTTCCGCCTGACTGACTTGAGACCTCGAC
CCGATCGACCTCTGTGA Gene 250 (SEQ ID NO:15)
ATGGTTGCGGCGCAAGGCTCCTCGATGCTAACCGCTGCCGATTTCGCCGCGCAATGGGCCGATGTTCCCCC
GTGGGAACCGCCGGACGAACCACCGCAGCGAAACGGCCAACGACAGCAGCAGGCAAGCGCCGAGCCGACCA
CGTGGGAGGCGTTCGATCTCGGACCCTACCTGCGCGGCGAAATCGAACGCCCACATCCCGGTATCGGCATA
TCACGCTCCGACGGGCAGCGGTCGCTCTACCCTGGTCGCGAGCACGCCATAGTCGGTGAAACCGAAAGCGG
TAAAACCTGGTTCGCGTTGGGCTGCGCCGCCGCAGAACTCAACGCCGGCAACGACGTCGTGTATATCCACT
ACGAAGAACCCGACGCGACGAGCACCGTCGAGAAGCTGTGCTTGCTTGGGGTCGACCCCGCGGTGATCAAG
GCCCGGTTTCGGTTCGTCGCTCCCAGCCGCCCCGTCCGTGAGGAGTGGCTGAACGCACTACTTGACCCTTC
ACCGACGCTGGTCATCCACGACGGCGTCAACGAAGCGATGGCGCTGCACGGCGACGAGATCAAGGCCGTCG
AGGGCGCCGCGGGCGTTTCGCCGGCCGACTGA Gene 251 (SEQ ID NO:16)
ATGGTGCGCGACGGCAGCCGCCGCGATGCCTACGGTTCGGTGCATAAGGGCAACGCGCTCGACGGGGCTCG
GTTCGTGCTCGAGAACTCGGCGCCGTTCGGCCGGCGGCTGCGCGGCGTCTCCTACGTCTTCGTGACCAAAG
ACCGCCCCGGGCATCTACGGGCCAACGGGCGCGCAACGAAGTCGCCCGGCAAGACGTTCATGGGAACTCTG
GTCGTCGATGACTCGCAGGCGTTCGGTCCTGACTTCACGATGCGGTTCTTCGCGCCCAGGGACGACGACGT
GCCTGAGAGCGATCCGAACGCCGAGCTGGCTGACGCTGTCTTTCGCGTCGTTGCTGCGGCTCCCGACCACG
CTGTTGGGTCGATGCGGCTGTTGTTCGCTGAGTTACGCAACGTCGACATCCAGTTCCGTGACGACGATGTG
CGCGACGTCGTCGATGACCTTGTGGTGTCAGGCCGTCTCGTAGAGATATCAGGCAAGCGTGGCGCCAAGGG
GTTCAGGGCCGTTGTGGAGGACGCCGATGGGGACAGCACGTGA Gene 252 (SEQ ID NO:17)
ATGACCACCGACAACCCCACGCCCTCTGATGACCAGGCACTGGCCGCCCTCTACGCCACAGCACTCGGCGT
GCTCCTGGCCGGCCTCGTCAACGACGGACGCCTCACGACCGAGATCGAGCGCATCATCGCCGCCGGCAGA
AAGTCACCGCCGGCGTCCTCGGCTTCCTGACCGCAGCAGCCGCCAACGCCTACGAATACGAGCACGGCAGC
CGAGAAGCCGCCATCGACGCAGTCACCGCAGACCTGGCCACCGTGCTGCTCGCCGCCGGAGAGGGACAGCC
CTCATGA Gene 253 (SEQ ID NO:18)
TTGACCGCGTTGACGGCGTTGCGCGACGTCCTGGCGGCGGCGATCGATGAATGCGGGTCGAAACGTGATTT
GGCCGCGTTGTTGCGGCAGTTCACCGCTGTCCTGGCGCAGATCGAGGCGGCGCGGGTACGGCCACCGCAAC
GTCGGATTGCCGATGAGATTGCGGCCCGGCGGACAGCTCGGCAGGCCGCGGCCGCTGCCGATGCGAAGAGC
GCGGACCGCTGA Gene 254 (SEQ ID NO:19)
ATGAGCGACGAGTTACGCCAGCGCTACAAGGTGATTTTCGATGCAGTCCGGGTGAGCGAAATCGAGATCAC
CCCGGATCTTGCGCGGTGCCTCGTGCACTGGCTCGGTGATTACATCCGGCTCAAGCAGCAGCCTGGGCAGC
CCGGTGTCCCGGAGGGGTTAGTTGCGGCGCAGACGGCGCTTGCCGAGGCGTACGCCGCGGTTACTCACTCG
CCTCGAAGCGAGCGGGATCGCCCGATCGGGGCTGGATTCGTATTCTCAGCCCATGACGCGTGGGTGGGCAC
TGCGGAAGCCGCTGAGATGCTCGGGATCAAGGCGGGCAGCGTCGGTTGGCTTTGCCGGGAGAGTCATCTTG
AGCACCGGAAAGTTGGCCGGCAGTACATGATTTCGACCGCATCGATCGAGGACTACAAACGCCGCAAGGCT
GAAAGGAGCGCGTGA

Figure 2-4

Gene 255 (SEQ ID NO:20)
ATGGTCAACGTGCCGCGTGCGGAACTTGCGCGGCTGGTGGGGGTTTCGCCGGACGTCGACGATCTAACGTT
GCAGCAGGCCATCGATTCCAAGCTCGCGCAGAATGAGGCCGAAAAGCACGCTCACGCGGTGTCTGCGGCCG
AGCAGCGGGCCCGCGCGGATGACCGGCGAATCGTCATCGCTGCCTACAACGAAGGCCGGATTCCGCAGAGC
CGCATCGACTTCTGGTGCGAAGCAATGCAACGAGACCGCGCCGGCAACAGGGCTATCCTCGCGGCTTTGGC
GCCGGGACTGGCCCCGCCTGAAAAGCTCCCTACTGACCCGCAGATCGAACATGTCCACGCGAAAGTCCTTG
CTCGGATGGGCATCCGGCCGCCGGCATCTGCTCCCACATCGCAGACTGTCGCTGCGTCATCGCCACCGCCG
TCACCAGGCGTCGATGATTTGGGCATACCGATCGCGCCGTTGCCGCCACCTGTGCGCATCGTGCGCATCGT
GCACGGCAAAGATCCGGCCACGTGGTCCAAAGAAGAGCGCGATAACGCGCTGCTGTACGGGCTCGGCCCCC
GGTTCGCCGCAGCGGCGGCGGCGCGTGGGATCCACGCCCACCCGGAGGCTCCGGGTACTACCAGCCGACC
GGCATCGAGCCCTACGAGCCCGTCGACCTGGGTGGCGGTCAGATCGAGTGGCGCGCCAAGCCCGACTACCG
GCCGCGGGGTGACTGA Gene 256 (SEQ ID NO:21)
ATGCCATACCGAATGAGTCCCCGCGTCCAGATGCTGGCCGTCAACGACCAGAACGGGATCATTTGGCATCA
CTACCAAAGACCTGTCGGGGGTGCCCGCAACCTTGGTCCGATCATTGCGTGGATTGGCCCTGACTACCGGG
ATCGCTGGCTACGCATGGGCCTCATCGAGGAGATCCCCGACGACGCCGCGGCCGCCCTGTCACAGCCCCCG
CCCAGCGATGCAGTCGCCGGCCCCAATACCGATCTCGTCGACGAGTGCATCGCCGCGCTCGACCGTTTCGA
TGTGCCAGCCGATGCCGGCGCCCCGACCGCGCGGAAAGCCCTGCGCGACAGGGGGCAAGCCTGGGGCAACG
AGACCATCGCTGCTGCTGTCCGCGCGCGCAAGGCCCGTGCCGCGCCGTCCGGGACGCCGGCAGGGTCATGA Gene 257 (SEQ ID NO:22)
ATGAGCACCACGACGGTGCCAGTCGGCACGACACCCGCTGCGATCACAGGGGATTCCGCCGGACGTCGACTC
GGTGCAAGTCCTCAACTCCAGCGAGGGGCTCGGTGATGCCGCCGGCGTCGACATCGTCGTCAACAACTCCG
GAGGCTGTTCGCTGGACCCGCAGACGGGGATCCGGCTCAAACCCGCCGAGTTCTTCGTGTTCTCGCTACGC
CAGCCACATGGGGGCCCGGCCGNTTGCCGCTGTACGCGGTCGCGGCCGGCCCTGGTGGTCAGTTGA

481 (SEQ ID NO:23)
TCAACTGACCACCAGGCCGGCCGCGACCGCGTACAGCGGCAANCGGCCGGGCCCCCATGTGGCTGGCGTA
GCGAGAACACGAAGAACTCGCCGGGTTTGAGCCGGATCCCCGTCTGCGGGTCCAGCGAACAGCCTCCGGAG
TTGTTGACGACGATGTCGACGCCGGCGGCATCACCGAGCCCCTCGCTGGAGTTGAGGACTTGCACCGAGTC
GACGTCCGGCGGAATCCCTGTGATCGCAGCGGGTGTCGTGCCGACTGGCACCGTCGTGGTGCTCATGACCC
TCCCGGCGTCCCGGACGGCGCGGCACGGGCCTTGCGCGCGCGGACAGCAGCAGCGATGGTCTCGTTGCCCC
AGGCTTGCCCCCTGTCGCGCAGGGCTTTCCGCGCGGTCCGGGGCGCCGGCATCGGCTGGCACATCGAAACGG
TCGAGCGCGGCGATGCACTCGTCGACGAGATCGGTATTGGGGCCGGCGACTGCATCGCTGGGCGGGGCTG
TGACAGGCCGGCCGCGGCGTCGTCGGGGATCTCCTCGATGAGGCCCATGCGTAGCCAGCGGATCCCGGTAGT
CAGGGCCAATCCACGCAATGATCGGACCAAGGTTGCGGGCACCCCGACAGGTCTTTGGTAGTCGATGCCAA
ATGATCCCGTTCTGGTCCTTGACGGCCAGCATCTCGACGCGGGGACTCATTCGGTATGCCATGTCAGTCAC
CCCGCGGCCGGTAGTCGGGCTTGGCGCGCCACTCGATCTGACCGCCACCCAGGTCGACGGGCTCGTAGGGC
TCGATGCCGGTCGGCTGGTAGTACCGGAGCCTCCGGGTGGGCGTGGGATCCCACGCGCCCCGCCGCTGC
GGCGAACCGGGGGCCGAGCCCGTACAGCAGCGCGTTATCGCGCTCTTCTTTGGACCACGTGGCCGGATCTT
TGCCGTGCACGATGCGCACGATGCGCACAGGTGGCGGCAACGGCGCGATCGGTATGCCCAAATCATCGACG
CCTGGTGACGGCGGTGGCGATGACGCAGCGACAGTCTGCGATGTGGGAGCAGATGCCGGCGGCCGGATGCC
CATCCGAGCAAGGACTTTCGCGTGCACATGTTCGATCTGCGCGGTCAGTAGCGAGCTTTTCAGGCGGGGCCA
GTCCCGGCGCCAAAGCCGCGAGGATAGCCCTGTTGCCGGCGCGGTCTCGTTGCATTGCTTCGCACCAGAAG
TCGATGCGGCTCTGCGGAATCCGGCCTTCGTTGTAGGCAGCGATGACGATTCGCCGGTCATCCGCGCGGGC
CCGCTGCTCGGCCGCAGACACCGCGTGAGCGTGCTTTTCGGCCTCATTCTGCGCGAGCTTGGAATCGATGG
CCTGCTGCAACGTTAGATCGTCGACGTCCGGCGAAACCCCCACCAGCCGCGCAAGTTCCGCACGCGGCACG
TTGACCATGCCCATCACGCGCTCCTTTCAGCCTTGCGGCGTTTGTAGTCCTCGATCGATGCGGTCGAAATC
ATGTACTGCCGGCCAACTTTCCGGTGCTCAAGATGACTCTCCCGGCAAAGCCAACCGACGCTGCCCGCCTT
GATCCCGAGCATCTCAGCGGCTTCCGCAGTGCCCACCCACGCGTCATGGGCTGAGAATACGAATCCAGCCC
CGATCGGGCGATCCCGCTCGCTTCGAGGCGAGTGAGTAACCGCGGCGTACGCCTCGGCAAGCGCCGTCTGC
GCCGCAACTAACCCCTCCGGGACACCGGGCTGCCCAGGCTGCTGCTTGAGCCGGATGTAATCACCGAGCCA
GTGCACGAGGCACCGCGCAAGATCCGGGGTGATCTCGATTTCGCTCACCCGGACTGCATCGAAAATCACCT

Figure 2-5

```
TGTAGCGCTGGCGTAACTCGTCGCTCATCAGCGGTCCGCGCTCTTCGCATCGGCAGCGGCCGCGGCCTGCC
GAGCTGTCCGCCGGGCCGCAATCTCATCGGCAATCCGACGTTGCGGTGGCCGTACCCGCGCCGCCTCGATC
TGCGCCAGGACAGCGGTGAACTGCCGCAACAACGCGGCCAAATCACGTTTCGACCCGCATTCATCGATCGC
CGCCGCCAGGACGTCGCGCAACGCCGTCAACGCGGTCAACGCATCACCGGACTTCGCCGCCTTAGAAACCG
AATTACGCGGTGTTACAACGTGACTCGTAGTTCCAGCATTACGCCTGACCATCAGTCAATCATCCCCTTGA
CGTGTGGAAATCTGCCAGGGGAGAGAAACAAGCGACCCGGCGGCGGTCGCCGAGGGGCCCCCTCCCCTCAA
GAAAATCGGCGGGTGGGGTCGACGTGTGCTCCTCGGGCATTACACGTCGGTGCTTGGGCGTGGGTCCGATC
GCAGGCGCGCACCGTTGGTCGGCGGTGGCTCTGTGTTCTTCTCGGCGTGGGTCGTTGTGTCTGGTGTCGCG
GGTGACCGGTCGTGGCCGGTAGCTGTTCATGAGGGCTGTCCCTCTCCGGCGGCGAGCAGCACGGTGGCCAG
GTCTGCGGTGACTGCGTCGATGGCGGCTTCTCGGCTGCCGTGCTCGTATTCGTAGGCGTTGGCGGCTGCTG
CGGTCAGGAAGCCGAGGACGCCGGCGGTGACTTTCTCGCCGGCGGCGATGATGCGCTCGATCTCGGTCGTG
AGGCGTCCGTCGTTGACGAGGCCGGCCAGGAGCACGCCGAGTGCTGTGGCGTAGAGGGCGGCCAGTGCCTG
GTCATCAGAGGGCGTGGGGTTGTCGGTGGTCATGGTGTGCCTTTCGGGTTGGGGTGGATGGGGTGTTGCTT
TCTGGGTCGGCCGCGCTGTTGGGTGCGGAGCTGGCCCGCTACGACGCCGTGCGGCCGGTGTCTGGCGGGTA
GGGCGTTGAACCATGCGCGGCAGCGGTCGGCGGCCGGACACCGCGAACACAGGCCGAGGACCTGGGCGTGG
CGCTGCTCAACGACTTCGGGGGCCTCGTTCGGTGCTGCTTCGTCGAACAGGTGATGCCGGCCGCGGCATCT
GGCACCTGGCAACGACGGTGCAGCGGCCAGCGCTTCGAGGAGGTGGTGCAGCGCGGTCATCGGGTGGCTCG
GTTCAACGGGGTCGTCCCTCCGGGATCGGGTTTTCTTGACTGTTTTCCGACTGCGTCCCGCGACCGCGTCC
TGCGTCCCCCCTACGGGGGGTGGGACGCAGTCGGACGCAGTCGCAGTCCGCTTGAACGCCACTGCGTCCGG
ACGCGGTGGGACGCAGTCGGACGCAGTCACGTGCTGTCCCCATCGGCGTCCTCCACAACGGCCCTGAACCC
CTTGGCGCCACGCTTGCCTGATATCTCTACGAGACGGCCTGACACCACAAGGTCATCGACGACGTCGCGCA
CATCGTCGTCACGGAACTGGATGTCGACGTTGCGTAACTCAGCGAACAACAGCCGCATCGACCCAACAGCG
TGGTCGGGAGCCGCAGCAACGACGCGAAAGACAGCGTCAGCCAGCTCGGCGTTCGGATCGCTCTCAGGCAC
GTCGTCGTCCCTGGGCGCGAAGAACTGCATCGTGAAGTCAGGACCGAACGCCTGCGAGTCATCGACGACCA
GAGTTCCCATGAACGTCTTGCCGGGCGACTTCGTTGCGCGCCCGTTGGCCCGTAGATGCCCGGGGCGGTCT
TTGGTCACGAAGACGTAGGAGACGCCGCGCAGCCGCCGGCCGAACGGCGCCGAGTTCTCGAGCACGAACCG
AGCCCCGTCGAGCGCGTTGCCCTTATGCACCGAACCGTAGGCATCGCGGCGGCTGCCGTCGCGCACCATCG
GGAGGTGGTCGCACGCCAGCGTGGCCGCGCCGACACGTAGGCATGGCAGGCATCAGTCGGCCGGCGAAACG
CCCGCGGCGCCCTCGACGGCCTTGATCTCGTCGCCGTGCAGCGCCATCGCTTCGTTGACGCCGTCGTGGAT
GACCAGCGTCGGTGAAGGGTCAAGTAGTGCGTTCAGCCACTCCTCACGGACGGGGCGGCTGGGAGCGACGA
ACCGAAACCGGGCCTTGATCACCGCGGGGTCGACCCCAAGCAAGCACAGCTTCTCGACGGTGCTCGTCGCG
TCGGGTTCTTCGTAGTGGATATACACGACGTCGTTGCCGGCGTTGAGTTCTGCGGCGGCGCAGCCCAACGC
GAACCAGGTTTTACCGCTTTCGGTTTCACCGACTATGGCGTGCTCGCGACCAGGGTAGAGCGACCGCTGCC
CGTCGGAGCGTGATATGCCGATACCGGGATGTGGGCGTTCGATTTCGCCGCGCAGTAGGGTCCGAGATCG
AACGCCTCCCACGTGGTCGGCTCGGCGCTTGCCTGCTGCTGTCGTTGGCCGTTTCGCTGCGGTGGTTCGTC
CGGCGGTTCCCACGGGGGAACATCGGCCCATTGCGCGGCGAAATCGGCAGCGGTTAGCATCGAGGAGCCTT
GCGCCGCAACCAT
```

Figure 2-6

Gene 10 (SEQ ID NO:24)
VRPHTGGRRISIYWTWSYPWESQRDIQTLDNRFSTMTEVRRAAWPRYEGPDWDDAHFLQGIAGTLELFHRS
TLAFQELAGEATGQQVAVFQRVDQAGYRLVIDERILADTDTLMVFGLDHLAGEDEAEPGEISAIRAWLERE
GTCLLLAPHHDVGGTDDMAQRQVEYLHHGDPLVPRQQRFSAYTRSLMKGLDVPVRNRWGLHPARVAATGQM
APLTCFRDLDAPGLLDDVTTLNFHPHLPHYELTAPESDGLRVLATQRVDPARPHPFTEAGNSEFNALIWMP
PHAERAGDIVLVDSTNFTTLFGGSDSLRNFWHNLATMR*

Gene 11 (SEQ ID NO:25)
MVATEHEWSKPAALAIPREGYFELERGRYGPLYPRTPACYGFSIIAKVKEGREEAVRAYGKQIEEAIKADP
HVLAALRLHYLRWLLFDVGSGLHFQYQGIFDTDFDKYTEDAVQLFSQTGITTVFTNLEGFPEDWRENPDAF
VKFVREHQCPSFLEYGEYPYVTADEIKKAYGSSRLPDHAGSDAMTSVRV*

Gene 38 (SEQ ID NO:26)
MVVSISAPTVPIPQAMTFSGLRSDIGQKPTRGQHRQRDAAIFELPVRPMRDVGHFDFLPALRFGVRPPDVD
DQVAGLVGRVQIRPVRIDTGGHDLEGTDIVRRQRRHPTAVADGGGVAWDAHPHRVARSCPEALHGCSGVGE
RAQGGMQIEDRSKVICADAKPEAALMRAEPT*

Gene 56 (SEQ ID NO:27)
MNTSSSLPVDTLDVTAPPDATEVYGWAAHPDGLAARAFEAAVRDCAGYRVRVRGAQRSNVTCRRWVAIEAA
PGADEQALEPEAVRQLAPQMSVTPTTRRTAEMLDDAAFDAIVAVFSQRARCEMQTLSGGKCPRAARWRIDL
HGCEQAIVCGQHKKAWLQEALANLWRGIQPRCAHCGRVFNSFQDAVRITAI*

Gene 57 (SEQ ID NO:28)
MATNDDQDDGKPPITAAAGGDETAIGAAADETELVAPLTVPASELAWSHEDSDAGDYSWGRAAERASIIVL
ACAAVAVVIGLLTWLALHLHDQAKPTAGPTAA Gene 128 (SEQ ID NO:29)
MSARDLINIGVFGALYIATVFAINVFAFINPLVMLVALAVSMIAGGVPFMLFLTRVRHAGMVTVFAIITAG
LLALTGHPPICFVITVACALVAEVVLWLGRYRSRTMGVLAYAIYAAWYIGPLLPIFYARDEYFSSPGMAQM
GPRYLEEMERLLSPAVLIAFDLSTVVFGLIGGLLGVRLLRKHFQRAGLA*

Gene 135 (SEQ ID NO:30)
MAGMPEEVAALLRGFPRIGAREQAFAFLTVDTGGFPHAALLSRCELEPGRDPQTLMAAIASRQTRANLRRS
GTAGLLAINGTSCHHLKLRVVASLVGRGILGCVFAVTEHKRDDMGIPLQPTLFRTSAEISVLEDWPRSRAM
FDRLAALRSAAREVL*

Gene 159 (SEQ ID NO:31)
MRFALPTRILHWLMAPMVIGQLLIGVVMITSLTYYPLLLAIHRPLGALILAFAVVRLANRFTHRLPPFLAT
MGPVERRVATWSEYLLYALLLAQPLIGWAMLSAARFPVVLVGPVHLPGIAPHNVDVYAALRQAHNVGAFLL
FLTFTAHVCAVLFHTLGLRDRLLDRMALWPTKPVASRQDEIKA*

Gene 217 (SEQ ID NO:32)
LRRLMAERGLFNTTALRPLLAERGVQLSASQVYRLVTEKPERLSLPTLVALVDILRCAMDELIEIVPATAA
SAKKAAGAPERSKPVRTRELGGHRPVRAKIVDADS*

Gene 218 (SEQ ID NO:33)
MRGNRSEFVTVIVTAVGAIEPHLSHDDVRTAIEGMCLSAAQLQRLSRTLRRDGSVLTGPGGSDCAADIEQL
ILCLRQLGAMRVRAPRCAQCGRNDSETYSRKLKKRICRACSMQGWQPAVGECPGCGAVDKLIYRPRHGDGL
LCRRCKPEPDVDHAAKVRDGIAQLRTGLSATEIDRVASVFGTAVAQRELNWILQDTPGVFRGEIAHRSAVS
VRLAELLVAAGADNVRLPQCPLCLRTVKLGSQIDGLRCCHTCWGHHFSRGTCARCGCQRHLINYHGAGERL
CHRCFEHDPVNHEPCTRCGRVDFINHHDGQAKLCRRCYPAPTAVCSSCGRTRPCTRTRTGKPICGTCSAKQ
RPPQPCSVCGNIRSVHTRTDAGEPVCNPCARSREPCARCGKTLGVSARLAGVGPLCSACLQREPAYFTDCV
QCGAHGRTYHRGLCPACACPGELRELFAKNGELSGAASRIVEALLQCDAMPVLRWVRRMRSNSELPAQLAE
LGDTLSHHDLDDLPASKSVEWLRNILVTAEGLPDRDPYLHRTEQYIAARLATISNRDDRAAVRAFTEWNHL

Figure 3-1

RKLRARADKGPLKRNHGLAAQIMAAAITDFVSELNAHGLALASCQQAFVDDWLVRNPTRRQIHQFLAWAVH
RGYAHDVAAPVPQTRRTRHTLPGDDERWRLIQYLIEHPDLETRDRVAGLLVLLYSQPAARLVTLKVADVTI
TDDAVQLTLGAVPLTVPSPVDRLLADLVQQRRGYAAVTVGTNPWLFPGGRSGGHLSANQVGLRLKRIGISP
RIARNTALIDLAGELPAVVLAKLLGFSIKRAVTWSEEAGNTRPRYAAEVARRNS*

Gene 219 (SEQ ID NO:34)
VSTSTERRLRLQVAVHESWARTENRSARTHNARKAAWDRFEKQVDPEGKLPPALRAKMAENARAAHFKKMA
LKSVESRRRRRDGVAA*

Gene 228 (SEQ ID NO:35)
VPYAESPRTRTGGVFTLEQAQPDDGLVVVRAAGLGQRAIGDDSGVGLDGKVGFEAVLAAVHRLVSVPRVGI
DGGDHAIPTDLLRDAPVPVGAIRALDRFNVLTGDQRQQRHRLSSPRREFLVRQIAQHPVSITDQTIHQPIP
SGLILPRNRGFPRIVVIMGAAVGFDHRCSARDFAAHSSDRGDQLRHGVLRGHRIVEHRGIQGPPCLARQHP
GLGHHRLDRLEDPVGPIRSRQPTPPIRQRRRMKRARRDRQPARCFPAQIESHRIHGLVIRKTVQGLQGDHR
GHHLSRHAGPAPLRREQVREHLLGKQLAAVRRQERKHAVGLQKMPGNRLRIQQLTLIIRATLHPTIIPKTP
GQLVPPRGINSAGS*

Gene 240 (SEQ ID NO:36)
LVIALAALWSIRLAWHIPFERAAVLALAFMCAQLVLALGPVDGWLSPLLHDMTGVWNLEDLIGHLLYVYGL
FSIMYLVADHCDMTPGQLRWFVRNRLELPSVVICAVMIAVFVAGDIGETCVPDVVATEHTPWLRVYWFVMI
AALAYIIVSTGRILLILRQHPRSRHAATAYLVALGITGACCVVFIIGIPWLQWLLVRCEVVGYAVAASYSW
RNKVAYFRGR*

Gene 241 (SEQ ID NO:37)
LHEILRFGGKTDELIGFARALSVQTATLPGMSSHSPVSAAALASRLRMIMGDRKLSRTRLSHETGISRPSL
SSKLDGKVEFTYSELLTIAQAVDVPLDKLLAGDDDERPFRLSDLRPRPDRPL*

Gene 250 (SEQ ID NO:38)
MVAAQGSSMLTAADFAAQWADVPPWEPPDEPPQRNGQRQQQASAEPTTWEAFDLGPYLRGEIERPHPGIGI
SRSDGQRSLYPGREHAIVGETESGKTWFALGCAAAELNAGNDVVYIHYEEPDATSTVEKLCLLGVDPAVIK
ARFRFVAPSRPVREEWLNALLDPSPTLVIHDGVNEAMALHGDEIKAVEGAAGVSPAD*

Gene 251 (SEQ ID NO:39)
MVRDGSRRDAYGSVHKGNALDGARFVLENSAPFGRRLRGVSYVFVTKDRPGHLRANGRATKSPGKTFMGTL
VVDDSQAFGPDFTMRFFAPRDDDVPESDPNAELADAVFRVVAAAPDHAVGSMRLLFAELRNVDIQFRDDDV
RDVVDDLVVSGRLVEISGKRGAKGFRAVVEDADGDST*

Gene 252 (SEQ ID NO:40)
MTTDNPTPSDDQALAALYATALGVLLAGLVNDGRLTTEIERIIAAGEKVTAGVLGFLTAAAANAYEYEHGS
REAAIDAVTADLATVLLAAGEGQPS*

Gene 253 SEQ ID NO:41)
LTALTALRDVLAAAIDECGSKRDLAALLRQFTAVLAQIEAARVRPPQRRIADEIAARRTARQAAAAADAKS
ADR*

Gene 254 (SEQ ID NO:42)
MSDELRQRYKVIFDAVRVSEIEITPDLARCLVHWLGDYIRLKQQPGQPGVPEGLVAAQTALAEAYAAVTHS
PRSERDRPIGAGFVFSAHDAWVGTAEAAEMLGIKAGSVGWLCRESHLEHRKVGRQYMISTASIEDYKRRKA
ERSA*

Gene 255 (SEQ ID NO:43)
MVNVPRAELARLVGVSPDVDDLTLQQAIDSKLAQNEAEKHAHAVSAAEQRARADDRRIVIAAYNEGRIPQS
RIDFWCEAMQRDRAGNRAILAALAPGLAPPEKLPTDPQIEHVHAKVLARMGIRPPASAPTSQTVAASSPPP

Figure 3-2

SPGVDDLGIPIAPLPPPVRIVRIVHGKDPATWSKEERDNALLYGLGPRFAAAAAARGIPRPPGGSYYQPT
GIEPYEPVDLGGGQIEWRAKPDYRPRGD*

Gene 256 (SEQ ID NO:44)
MAYRMSPRVEMLAVKDQNGIIWHHYQRPVGGARNLGPIIAWIGPDYRDRWLRMGLIEEIPDDAAAALSQPP
PSDAVAGPNTDLVDECIAALDRFDVPADAGAPTARKALRDRGQAWGNETIAAAVRARKARAAPSGTPAGS*

Gene 257 (SEQ ID NO:45)
MSTTTVPVGTTPAAITGIPPDVDSVQVLNSSEGLGDAAGVDIVVNNSGGCSLDPQTGIRLKPGEFFVFSLR
QPHGGPAXCRCTRSRPALVVS*

Figure 3-3

Gene 10 (SEQ ID NO:1)
GTGCGCCCGCACACCGGCGGACGGCGGATCAGCATCTACTGGACGTGGAGCTATCCGTGGGAATCGCAGCG
CGACATTCAGACCCTGGACAACCGCTTCTCCACCATGACCGAAGTGCGCAGGGCGGCCTGGCCCCGATACG
AGGGGCCCGACTGGGACGACGCCCACTTTCTGCAGGGCATCGCCGGCACCTTGGAGCTTTTCCACCGCTCG
ACGCTTGCGTTCCAGGAGCTGGCCGGCGAAGCAACCGGTCAGCAGGTGGCGGTGTTCCAGCGCGTCGACCA
GGCCGGCTACCGGCTGGTGATCGACGAGCGGATATTGGCCGACACCGACACCCTGATGGTGTTCGGGCTGG
ACCATCTCGCCGGGGAAGACGAGGCCGAGCCCGGGGAGATCTCGGCCATCCGTGCCTGGCTGGAACGCGAG
GGCACCTGCCTGCTGCTGGCCCCGCACCACGACGTCGGCGGCACCGACGACATGGCCCAGCGGCAGGTCGA
ATACCTGCACCACGGGGATCCGCTCGTGCCGCGGCAACAACGGTTTTCCGCCTACACCCGCTCGCTGATGA
AGGGGCTCGACGTTCCCGTCCGCAACAGGTGGGGCCTGCATCCGGCCCGGGTGGCCGCGACCGGTCAGATG
GCACCGCTGACCTGCTTTCGCGACCTGGACGCGCCCGGGCTGCTGGACGATGTCACGACGCTGAACTTTCA
CCCGCATCTGCCGCACTACGAGCTCACCGCCCCGGAAAGCGACGGGCTACGGGTGCTGGCCACCCAACGCG
TCGACCCGGCCCGGCCCCATCCCTTTACCGAGGCGGGCAACAGCGAATTCAACGCGTTGATCTGGATGCCG
CCGCACGCCGAACGAGCCGGTGACATCGTGCTCGTCGACTCGACCAACTTCACGACGCTGTTCGGCGGGTC
CGACAGCCTCAGAAACTTCTGGCACAACCTGGCCACGATGAGGTGA 75% sequence identity to Gene 10 (SEQ ID NO:102)
CTGCGCGCGCTCAGCGGGGGACGCGGGAACAGGATCTAGTGGTCGTGGTGCTTTCCCTGGGATTCGCTGGG
CGACTTTCTCACCGTGCACAACGGCTACAGCACCTTGACTGAAGAGCGGAGGGGGGCCAGGCGCCCATTCC
AGGGCCCCCACTCCGACGTCGCCGACATTGTGGAGGCCATCGCGGGCTCGTTGGTGCAATTCCTGCGCACG
ACCCTTGCCTTCCTGGTGCTGGCCCGGGATGCTTCCGGTCACCTGGTGGGGAGTACCTGCGCGTCGAGCA
CGGCGGCATCCGGCTCCTGTTCGACGACCGGATATTGGCCGACACCGACACCCTGATGGTGTTCGGGCTGG
TCCTTCTCCCCGCCGAAGTCGTGGCCCAGCCGGGGCAGAACTCGGCGATCGGAGCCAGGGTGGATCGCGTG
GGCTCCAGCCTGCTCCTCGCCCGGCAGCAGGACGACGCCGGCTCCGACGTCAAGCCCGACCGGGAGGACGA
TTAGCTGCACCTCGGGCATCGGCACGTCCCCCCGCTACATCGGTTATCGGCCTACACGGGCTCCCTGTTCA
AGGCGCTGGACCTTGCCGTGCGCATCACGTCGGGGCTGCTTCCGGCGCCCCTGGCCGCCACCGCTCTGATG
GCTCCCCTGAGCAGGTTTCGCGTCCTCGAGGCGGCCGCGGTCCTGCACGTTGTCTCGACCCTCAACATTGA
CCGGCAACTCCCCCACTTCGACCTCACCCGCCGGGTAAGGGACGGCCTAGGGGAGCTGCCCAGCCTACGGG
TGGACGCGCGCCGGCCCCATCGCTATAGCGAGCCGGCCAACTGCGATTTCTACGGGTAGTTCAGGATCCCG
CGGCTCCCCGTACGTGGCGCTGTCCTCGAGCTGGTCGTCTCCACGATCTACAGGAGGCTGATCGGCAGATC
CGACAGTTTCAGAATCTCCTAGCACTTCCTGCCCAGGATGAAGTGA 80% sequence identity to Gene 10 (SEQ ID NO:103)
CTGCCCCCGCACTCCGGCCGAGGGCCGATCTGCATGTACTGGACCTCGAGCAATGCGTGGGATTCGCACCG
CGAGATTCTGACCCAGGTCAAGCGGTTCTGCACCTTGACCGATGTGGGCAGCGCGGCGTCGCCCCGTTACG
TGGGGGCCGAGTGCGACGAGGCGCACTTTCTGCACGCCAACGCCGGCACGTTGCAGCTTTACCAGCGCTGG
ACGCTAGCCTTCCTGGAGCAGGCGGGCGTAGGAACCGGACAGGAGGTGGCCGAGTTCGAGCGCGTCCTGCA
GGCCGGCAACGGGCTGGTGAACGTCGAGCCGATAATGCCCGTCACCGTCACCGTGATCGTGTACGGGCTCG
ACGATCTCGGCGGGGAAGAGGAGGGCCAGGCCGGGGACATCTGGGCCTTCCGTCCCTCCCTGGAACCCGTG
GGCACCTCCCTGCACCTGGGCCCGCTCCACGTCGTCGCCGGTACCGACGTCAAGGCCCTGCGGGAGGACGA
AAACCAGCACCAGGGGCATCCCCTCGAGCCGGGGCTACAAGGGATTACCGCCTACTCCGGCTCGCAGATCA
AGGCGCTCGTCGTTGCCCTCCGCTACAGGAGGCGCGTGCATCCGCCCGGGGTGGCCGGGACGGGACAGTTG
GCACGGCTGAGCTGCTATCCCCACCTCGACGGGCCCGGGCAGGTGGACGTTGTCAGGACCCTGAACATTCT
CCGGCATCTCCCCCACTTCGTGCACACCGCCCCGGTAACCGACCGGCTTCGCGTGCAGGCCACCGAACCCG
TCGTCCCGCCCCGCCGCATGCCTTAACCGTGGCCGGCAACTGCGAAATCATCGGGTTGTTCTGCATGCCG
GCGCAGGCCGATCGACCCGGAGAGATCGTGCTGGTCGTCTCCACCTACATCACGTCGCTCTTCGGGGGTG
CGACTGCCACAGATACTTCAGGCTCAAGCTGCCCACGAAGAGCTGA 85% sequence identity to Gene 10 (SEQ ID NO:104)
CTGCGCCCGCTCACCGCGGGAGGGCGGTTCAGCATCTACTGGAGGTGGAGCTTTCCGTGGGAAACGCAGCG
GGACATTCTGACCGTGGACAAGCGCTACTGCACCTTGACCGTAGTGCGCTGGGCCGGCTGGCCCCGTTACC
AGGGCCCCGACTGCGACGACGCCCAGTTTCAGCAGGGGATCGCCGCCACCATGGACCTTTACCTCCCCTCG
ACCCTTGCGTACCAGGTGCTGGCCGGCGAAGGAACCGGACAGGAGGTCGCGGTGATCCACCGCGTCGTCCA
GGCCCGCTACCGGGTGGTGATCCACGTGCGGAAATTGGCCGACTCCGACAGCCTGATCGTGTTCGGCCTGC

Figure 4-1

ACCAACTCGCGGGGGAACACGAGGCCGTGCCCCGGGACATCACGGCCTTCCGAGCCTGGCTCGAACGCGTG
GGCACCAGCCAGCTGCTGCCCCCGCTCCACGAGGTCGGCCGCAGCGACCACATGGCGCAGCGCCAGGTGGA
ATACCTGCTCCACGGCGATCCGGTCCTGCGGCGGCATCAACGGTTTTCCGCCAAGACCGGCTCGCTGATCA
AGGGGCTCGACGTTCGCGTCCGCTTCAGCTGGGGCCAGCATCCGGCCGGGGTGGGCGCGACCGGACAGATG
GCTCCGCAGACCTCCTTTCGGGACCTGGTCGCGCGCCGGCTGCAGGACCATGTCACCACGCTGATCTTTCA
CCGGCTTCTGCCGCTCTACGAGCACACCGCCCCGCAAACGGACGGCCTACGGGTGGTGGGCACCCTACGCC
TCGACCCGGGCCGGCGCCATCCCATTACCGTGGCGGGCAAGAGCGAATACAACGGGTTGATGTGGAAGCCG
CCGCTCGCCGTACGAGCCGGAGACATGGTGCACGTCCACTCGTCCATCTTCACGACGCAGTGCGGCGCGTC
CGACAGCATCAGAAACTTCTGGCACATCCCGGCCACGATGAGGTGA

90% sequence identity to Gene 10 (SEQ ID NO:105)
GTGCGGCCGCACTCCGGCGGACGGCGGTTCAGCTTCTACTGGACGTGCAGCTAACCGTGGCAATCGCAGCG
CGACATTGAGACCGTGGACAACCGCATCTCGACCATGACCGAAGTGCGGAGGGCCGCCTGGCCGCGATACG
AGGGCCCCCACTGGGACGACGCCCACTATCTGCAGCGCATGGCCGGCACCTTCGAGCTATTCCACCGCTCG
ACGCTAGCGTTGCAGGAGGTGGCCGGCGAAGCAACGGGTCAGCTGGTGGCGCTGTTCCACCGCGTCGACCA
GGCCCGCTTCCGGCTGGTGATCGACCAGGGGATATTGGCCGTCACCGTCACCCTGATGGTGTTGGGGCTGG
TCCATCTGGCCGGGGAAGACGAGCCCGAGCCCGGCGTGATCTCGGCCAACCGTGCCTGGCTCGAACCCGAG
GGCACCTGCCAGCTGCAGGCCCCGCACCACCACGTGGGCGGCACCGACGACTTGGGCCAGCGGCAGGTCGA
ATTCCTGCACGACGGCATCCGCTCGTGCCGGGGCAACATCGGTTTACCGCCTAGACCCGCTCGCTGATGA
ACGGGCTCGTCGTTCGCGTCCGCTACAGGTGGGGCCTCCATCCGGGCCGGGTGGCCGCGTCCGGTCACATG
GCACCGCTGAGCTGCTTTCGGGAGCTGGACGCGCCCGCGCTGCTGGACGAAGTCACGACGCTCAACTTTCA
CCCGCTTCTGCCCCACTACGAGCTCACGGCCCCGGTAAGCGACGGGCTAGGGGTGCAGGCCAGCCAACGCC
TCGACCCGGCCCGCCCCCAACCCTTTACCGAGCCGGGCAACAGCGTATTCATCGCGTTGATCTGGAAGCCG
CCGCACGGCGAACGTGCCGGTCACATCGTGCTCCTCGACACGACCAACTTCACGAGGCTGTACGGCGGGTC
CGAGAGCCACAGAAACTCTGGCACTACCTGGCGACGATGAGGTGA 95% sequence identity to Gene 10 (SEQ ID NO:106)
CTGCGCCCGCACACCGGCGGACGGCGGATCAGCATCTACTGGACGTGGTGCTATCCGTGGGAATCGCACCG
CGACATTCAGACCCTGGACAACCCCTTCTCCACCAAGACCGAAGTGCGCAGGGCGCCCTGGCCCCGATACG
AGGGGCCCGACAGGGACGACGCCCACTTTCTGCAGGGCATGGCCGGCACCTTGGAGCATTTGCACCGCTCG
ACGCTTCCGTTCCAGGAGCTGGCCGGCGAAGCAACCGGTCTGCAGGTGGCGGTGTTGCAGCGCGTCGACCA
GGCCGGCTACCGGGTGGTGATCGAGGAGCGGATATTGGCCGACACCCACACCCTGATGGTGTTCGGGCTGG
ACCATCTCCCCGGGGAAGACGAGGCCGTGCCCGGGGAGAACTCGGCCATCCGTGCGTGGCTGGAACGCGAG
GGCACCTGCCTGCTGCTGGCCCCGCACCACGACGTCGCCGGCACCGACGACATGGGCCAGCGGCAGGTGGA
ATACCAGCACCACGGGGATCCGCTCGAGCCGCGGCAACAACGGTTTTCCGCCTACACGCGCTCGCTGATGA
AGCGGCTCGACGTTCCCGTCCGCAACAGCTGGGGCCTGCATCCGGCGCGGGTGGCCGCGACCGGTCAGATG
GCACCGCTGACCTGCTATCGCGTCCTGGACGCCCCCGGGCTGCTGGACGATCTCACGACGCTGAACATTCA
CCCGCATCTGCCGCACTACGAGCACACCGCCCCGGAAAGCGACGGGCTACGGGTGCTGGCCACGCAACGGG
TCGACCCGGCGCGGCCCCATCCCTTTACCGAGGCGGGCAACAGCGAATACAACGCGTTGATCTGGATCCCG
CCGCACGCCGATCGAGCCGGTGACATCGTGGTCGTCGACTCGACGAACTTCACGACGCTGTTCGGCGGGTC
CGACAGCCTCAGAAACTTCTGGCACAACCTGGCCACGATGAGGTGA 99% sequence identity to Gene 10 (SEQ ID NO:107)
CTGCGCCCGCACACCGGCGGACGGCGGATCAGCATCTACTGGACGTGGAGCTATCCGTGGGAATCGCAGCG
CGACATTCAGACCCTGGACAACCGCTTCTCCACCATGACGGAAGTGCGCAGGGCGGCCTGGCCCCGATACG
AGGGGCCCGACTGGGACGACGCCCACTTTCTGCAGGGCATCGCCGGCACCTTGGAGCTTTTCCACCGCTCG
ACGCTTGCGTTCCAGGAGCTGGCCGGCGAAGCTACCGGTCAGCAGGTGGCGGTGTTCCAGCGCGTCGACCA
GGCCGGCTACCGGCTGGTGATCGACGAGCGGATATTGGCCGACACCGACACCCTGATGGTGTTCGGGCAGG
ACCATCTCGCCGGGGAAGACGAGGCCGAGCCCGGGGAGATCTCGGCCATCCGTGCCTGGCTGGAACGCGAG
GGCACCTGCCTGCTGCTGGCCCCGCACCACGACGTCGGCGGCACCGACGACATGGCCCAGCGCCAGGTCGA
ATACCTGCACCACGGGGATCCGCTCGTGCCGGGGCAACAACGGTTTTCCGCCTACACCCGCTCGCTGATGA
AGGGGCTCGACGTTCCCGTCCGCAACAGGTGGGGCCTGCATCCGGCCCGGGTGGCCGCGACCGGTCAGATG
GCTCCGCTGACCTGCTTTCGCGACCTGGACGCGCCCGGGCTGCTGGACGATGTCACGACGCTGAACTTTCA
CCCGCATCTGCCGCACTACGAGCTCACCGCCCCGGAAAGCGACGGGCTACGGGTGCTGGCCACCCAAGGCG

Figure 4-2

```
TCGACCCGGCCCGGCCCCATCCCTTTACCGAGGCGGGCAACAGCGAATTCAACGCGTTGATCTGCATGCCG
CCGCACGCCGAACGAGCCGGTGACATCGTGCTCGTCGACTCGACCAACTTCACGACGCTGTTCGGCGGGTC
CGACAGCCTCAGAAACTTCTGGCACAACCTGGCCACGATGAGGTGA
```

MYCOBACTERIAL DIAGNOSTICS

CROSS REFERENCE TO RELATED APPLICATIONS

This application claims priority under 35 U.S.C. §119(e) of U.S. provisional application Ser. No. 60/362,396, filed Mar. 6, 2002.

FEDERALLY SPONSORED RESEARCH OR DEVELOPMENT

The U.S. Government may have certain rights in this invention pursuant to USDA Grant Nos. 00-35201-9200, 58-3625-0-137, and 00-02215.

TECHNICAL FIELD

This invention relates to detection of bacteria, and more particularly to detection of *Mycobacterium avium* subsp. *paratuberculosis*.

BACKGROUND

The disorder known as Johne's disease was first described in 1895. Today, *Mycobacterium avium* subsp. *paratuberculosis* (*M. paratuberculosis*), the causative agent of Johne's disease, is widely distributed both nationally and internationally in domestic ruminants such as cattle, sheep, goats, as well as wildlife such as rabbits, deer, antelopes, and bison. In 1996, the National Animal Health Monitoring System conducted a survey of dairy farms using serological analysis to determine the prevalence of Johne's disease in the U.S. The results of that study showed an estimated 20–40% of surveyed herds have some level of *M. paratuberculosis*. Furthermore, it is estimated that annual losses in the U.S. from *M. paratuberculosis* in cattle herds may exceed $220 million.

The pathogenesis of *M. paratuberculosis* has been recently reviewed by Harris and Barletta (2001, *Clin. Microbiol. Rev.*, 14:489–512). Cattle become infected with *M. paratuberculosis* as calves but often do not develop clinical signs until 2 to 5 years of age. The primary route of infection is through ingestion of fecal material, milk or colostrum containing *M. paratuberculosis* microorganisms. M cells likely serve as the port of entry for *M. paratuberculosis* into the lymphatic system similar to other intracellular pathogens such as salmonella. *M. paratuberculosis* survive and may even replicate within macrophages in the wall of the intestine and in regional lymph nodes. After an incubation period of several years, extensive granulomatous inflammation occurs in the terminal small intestine, which leads to malabsorption and protein-losing enteropathy. Cattle shed minimal amounts of *M. paratuberculosis* in their feces during the subclinical phase of infection, and yet over time, this shedding can lead to significant contamination of the environment and an insidious spread of infection throughout the herd before the animal is diagnosed. During the clinical phase of infection, fecal shedding of the pathogen is high and can exceed $10^{10}$ organisms/g of feces. The terminal clinical stage of disease is characterized by chronic diarrhea, rapid weight loss, diffuse edema, decreased milk production, and infertility. Although transmission of *M. paratuberculosis* occurs primarily through the fecal-oral route, it has also been isolated from reproductive organs of infected males and females.

SUMMARY

The present invention provides nucleic acid molecules unique to *M. paratuberculosis*. The invention also provides polypeptides encoded by the *M. paratuberculosis*-specific nucleic acid molecules of the invention, and antibodies having specific binding affinity for the polypeptides encoded by the *M. paratuberculosis*-specific nucleic acid molecules. The invention further provides for methods of detecting *M. paratuberculosis* in a sample using nucleic acid molecules, polypeptides, or antibodies of the invention. The invention additionally provides for methods of preventing a *M. paratuberculosis* infection in an animal.

In one aspect, the invention provides an isolated nucleic acid, wherein the nucleic acid comprises a nucleic acid molecule of 10 nucleotides to 969 nucleotides, the molecule having at least 75% sequence identity to SEQ ID NO:1, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Homo sapiens*, *Pseudomonas aeruginosa*, *Streptomyces viridochromogenes*, *Mus musculus*, *Felis catus*, and *Xanthomonas campestris*.

For example, a nucleic acid of the invention can have the sequence shown in SEQ ID NO:1. A nucleic acid of the invention can have at least 75% sequence identity to SEQ ID NO:1 (e.g., SEQ ID NO:102). A nucleic acid of the invention can have at least 80% sequence identity to SEQ ID NO:1 (e.g., SEQ ID NO:10). A nucleic acid of the invention can have at least 85% sequence identity to SEQ ID NO:1 (e.g., SEQ ID NO:104). A nucleic acid of the invention can have at least 90% sequence identity to SEQ ID NO:1 (e.g., SEQ ID NO:105). A nucleic acid of the invention can have at least 95% sequence identity to SEQ ID NO:1 (e.g., SEQ ID NO:106). A nucleic acid of the invention can have at least 99% sequence identity to SEQ ID NO:1 (e.g., SEQ ID NO:107).

In another aspect of the invention, there is provided an isolated nucleic acid, wherein the nucleic acid comprises a nucleic acid molecule of 10 nucleotides to 576 nucleotides, the molecule having at least 75% sequence identity to SEQ ID NO:2, or the complement of the molecule, wherein any molecule that is 10 to 30 nucleotides, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Thermotoga maritima*, *Homo sapiens*, *Thermotoga neapolitana*, *Pseudomonas aeruginosa*, *Deinococcus radiodurans*, *Streptomyces coelicolor*, *Oryza sativa*, *Rhizobium leguminosarum*, *Frankia alni*, and *Mesorhizobium loti*.

In another aspect of the invention, there is provided an isolated nucleic acid, wherein the nucleic acid comprises a nucleic acid molecule of 10 nucleotides to 522 nucleotides, the molecule having at least 75% sequence identity to SEQ ID NO:3, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Halobacterium* NRC-1, *Oryza sativa*, *Glycine max*, *Streptomyces coelicolor*, and *Mus musculus*.

In another aspect of the invention, there is provided an isolated nucleic acid, wherein the nucleic acid comprises a nucleic acid molecule of 10 nucleotides to 582 nucleotides, the molecule having at least 75% sequence identity to SEQ ID NO:4, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Oryza sativa*, *Caenorhabditis elegans*, *Leishmania mexicana*, *Drosophila melangaster*, *Homo sapiens, Zea mays, Halobacterium* NRC-1, *Pseudomonas aeruginosa, Ralstonia solanacearum,* and *Streptomyces coelicolor.*

In another aspect of the invention, there is provided an isolated nucleic acid, wherein the nucleic acid comprises a nucleic acid molecule of 10 nucleotides to 311 nucleotides, the molecule having at least 75% sequence identity to SEQ ID NO:5, or the complement of the molecule, wherein any molecule that are 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Homo sapiens, Streptomyces coelicolor, Ictalurid herpesvirus, Mesorhizobium loti,* and *Oryza sativa.*

In another aspect of the invention, there is provided an isolated nucleic acid, wherein the nucleic acid comprises a nucleic acid molecule of 10 nucleotides to 576 nucleotides, the molecule having at least 75% sequence identity to SEQ ID NO:6, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Pseudomonas aeruginosa, Ralstonia solanacearum, Arabidopsis thaliana, Pseudomonas fluorescens, Homo sapiens,* and *Mesorhizobium loti.*

In another aspect of the invention, there is provided an isolated nucleic acid, wherein the nucleic acid comprises a nucleic acid molecule of 10 nucleotides to 474 nucleotides, the molecule having at least 75% sequence identity to SEQ ID NO:7, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Homo sapiens, Pantoea agglomerans, Rattus norvegicus, Erwinia uredovora, Escherichia coli,* and *Pantoea ananatis.*

In another aspect of the invention, there is provided an isolated nucleic acid, wherein the nucleic acid comprises a nucleic acid molecule of 10 nucleotides to 558 nucleotides, the molecule having at least 75% sequence identity to SEQ ID NO:8, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Neisseria meningitides, Homo sapiens, Streptomyces coelicolor, Arabidopsis thaliana, Escherichia coli, Pseudomonas aeruginosa, Streptomyces hygroscopicus* var. *ascomyceticus, Ralstonia solanacearum, Deinococcus radiodurans, Rhizobium meliloti, Rickettsia typhi, Streptomyces* sp., and *Mus musculus.*

In another aspect of the invention, there is provided an isolated nucleic acid, wherein the nucleic acid comprises a nucleic acid molecule of 10 nucleotides to 321 nucleotides, the molecule having at least 75% sequence identity to SEQ ID NO:9, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Mycobacterium tuberculosis, Homo sapiens, Streptomyces coelicolor, Drosophila melanogaster, Ralstonia solanacearum, Mesorhizobium loti,* and *Pseudomonas cruciviae.*

In another aspect of the invention, there is provided an isolated nucleic acid, wherein the nucleic acid comprises a nucleic acid molecule of 10 nucleotides to 2508 nucleotides, the molecule having at least 75% sequence identity to SEQ ID NO:10, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Sinorhizobium meliloti, Xanthomonas albilineans, Halobacterium* NRC-1, *Ralstonia solanacearum, Deinococcus radiodurans, Halobacterium salinarium, Micromonospora griseorubida, Pseudomonas paucimobilis,* and *Streptomyces lividans.*

In another aspect of the invention, there is provided an isolated nucleic acid, wherein the nucleic acid comprises a nucleic acid molecule of 10 nucleotides to 264 nucleotides, the molecule having at least 75% sequence identity to SEQ ID NO:11, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Caulobacter crescentus, Brucella melitensis, Pyrobaculum aerophilum, Mycobacterium tuberculosis, Sinorhizobium meliloti,* and *Mycobacterium leprae.*

In another aspect of the invention, there is provided an isolated nucleic acid, wherein the nucleic acid comprises a nucleic acid molecule of 10 nucleotides to 1110 nucleotides, the molecule having at least 75% sequence identity to SEQ ID NO:12, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Mesorhizobium loti, Bacillus halodurans, Ralstonia solanacearum, Homo sapiens, Drosophila melanogaster,* and *Rhizobium meliloti.*

In another aspect of the invention, there is provided an isolated nucleic acid, wherein the nucleic acid comprises a nucleic acid molecule of 10 nucleotides to 672 nucleotides, the molecule having at least 75% sequence identity to SEQ ID NO:13, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of a *Mycobacterium* sp. other than *M. paratuberculosis*.

In another aspect of the invention, there is provided an isolated nucleic acid, wherein the nucleic acid comprises a nucleic acid molecule of 10 nucleotides to 372 nucleotides, the molecule having at least 75% sequence identity to SEQ ID NO:14, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Brucella melitensis, Streptomyces coelicolor, Drosophila melanogaster, Mycobacterium tuberculosis, Trypanosoma rangeli, Trypanosoma minasense, Trypanosoma leeuwenhoeki,* and *Brassica napus*.

In another aspect of the invention, there is provided an isolated nucleic acid, wherein the nucleic acid comprises a nucleic acid molecule of 10 nucleotides to 600 nucleotides, the molecule having at least 75% sequence identity to SEQ ID NO:15, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Ralstonia solanacearum, Sinorhizobium meliloti, Homo sapiens, Mesorhizobium loti, Oryza sativa, Drosophila melanogaster, Rhizobium leguminosarum, Xylella fastidiosa, Deinococcus radiodurans, Achromobacter cycloclastes,* and *Candida cylindracea*.

In another aspect of the invention, there is provided an isolated nucleic acid, wherein the nucleic acid comprises a nucleic acid molecule of 10 nucleotides to 540 nucleotides, the molecule having at least 75% sequence identity to SEQ ID NO:16, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Streptomyces lavendulae, Xylella fastidiosa, Streptococcus pneumoniae, Mycobacterium tuberculosis, Pseudomonas aeruginosa, Ralstonia solanacearum, Sinorhizobium meliloti, Sus scrofa, Mycobacterium leprae,* and *Streptomyces coelicolor*.

In another aspect of the invention, there is provided an isolated nucleic acid, wherein the nucleic acid comprises a nucleic acid molecule of 10 nucleotides to 291 nucleotides, the molecule having at least 75% sequence identity to SEQ ID NO:17, or the complement of the molecule, wherein any molecule that is 10 to 25 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Pseudomonas* sp., *Homo sapiens, Pseudomonas aeruginosa, Thauera aromatica, Oryza sativa, Ralstonia solanacearum, Rhizobium leguminosarum, Streptomyces coelicolor, Brucella melitensis, Drosophila melanogaster, Deinococcus radiodurans, Streptomyces noursei, Rhizobium meliloti, Synechococcus elongatus,* and *Mesorhizobium loti*.

In another aspect of the invention, there is provided an isolated nucleic acid, wherein the nucleic acid comprises a nucleic acid molecule of 10 nucleotides to 225 nucleotides, the molecule having at least 75% sequence identity to SEQ ID NO:18, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Rhodobacter capsulatus, Agrobacterium tumefaciens, Mycobacterium smeginatis, Pseudomonas aeruginosa, Ralstonia solanacearum,* and *Drosophila virilis*.

In another aspect of the invention, there is provided an isolated nucleic acid, wherein the nucleic acid comprises a nucleic acid molecule of 10 nucleotides to 441 nucleotides, the molecule having at least 75% sequence identity to SEQ ID NO:19, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Homo sapiens, Mus musculus, Leishmania malor, Pseudomonas aeruginosa,* and *Botrytis cinerea*.

In another aspect of the invention, there is provided an isolated nucleic acid, wherein the nucleic acid comprises a nucleic acid molecule of 10 nucleotides to 726 nucleotides, the molecule having at least 75% sequence identity to SEQ ID NO:20, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Oryza sativa, Caulobacter crescentus, Rhodobacter sphaeroides, Streptomyces coelicolor, Spermatozopsis similis, Homo sapiens, Sus scrofa,* and *Giardia intestinalis*.

In another aspect of the invention, there is provided an isolated nucleic acid, wherein the nucleic acid comprises a nucleic acid molecule of 10 nucleotides to 426 nucleotides, the molecule having at least 75% sequence identity to SEQ ID NO:21, or the complement of the molecule, wherein any molecule that is 10 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *Streptomyces coelicolor, Homo sapiens, Triticum aestivum, Oryza sativa, Brucella melitensis, Caulobacter crescentus, Pseudomonas aeruginosa, Ralstonia solanacearum, Bovine herpesvirus,* and *Mesorhizobium loti*.

In another aspect of the invention, there is provided an isolated nucleic acid, wherein the nucleic acid comprises a nucleic acid molecule of 10 nucleotides to 279 nucleotides, the molecule having at least 75% sequence identity to SEQ ID NO:22, or the complement of the molecule, wherein any molecule that is 10 to 30 nucleotides in length, in combination with an appropriate second nucleic acid molecule, under standard amplification conditions, generates an amplification product from M. paratuberculosis nucleic acid but does not generate an amplification product from nucleic acid of any of the organisms selected from the group consisting of Pseudomonas aeruginosa, Oryza sativa, Streptomyces sp., Streptomyces peucetius, Rhizobium sp., Mycobacterium tuberculosis, Caulobacter crescentus, Ralstonia solanacearum, Haloferax volcanii, Mycobacterium leprae, and Streptomyces coelicolor.

In another aspect of the invention, there is provided an isolated nucleic acid, wherein the nucleic acid comprises a nucleic acid molecule of 10 nucleotides to 4415 nucleotides, the molecule having at least 75% sequence identity to SEQ ID NO:23, or the complement of the molecule, wherein any molecule that is 10 to 30 nucleotides in length, in combination with an appropriate second nucleic acid molecule, under standard amplification conditions, generates an amplification product from M. paratuberculosis nucleic acid but does not generate an amplification product from nucleic acid of any of the organisms selected from the group consisting of Ralstonia solanacearum, Sinorhizobium meliloti, Homo sapiens, Mesorhizobium loti, Oryza sativa, Drosophila melanogaster, Rhizobium leguminosarum, Xylella fastidiosa, Deinococcus radiodurans, Achromobacter cycloclastes, Candida cylindracea, Streptomyces lavendulae, Streptococcus pneumoniae, Mycobacterium tuberculosis, Pseudomonas aeruginosa, Sus scrofa, Mycobacterium leprae, Streptomyces coelicolor, Pseudomonas sp., Thauera aromatica, Brucella melitensis, Streptomyces noursei, Rhizobium meliloti, Synechococcus elongates, Rhodobacter capsulatus, Agrobacterium tumefaciens, Mycobacterium smegmatis, Drosophila virilis, Mus musculus, Leishmania major, Botrytis cinerea, Caulobacter crescentus, Rhodobacter sphaeroides, Spermatozopsis similes, Giardia intestinalis, Triticum aestivum, Bovine herpesvirus, Streptomyces sp., Streptomyces peucetius, Rhizobium sp., and Haloferax volcanii.

Generally, the invention provides an isolated nucleic acid, wherein the nucleic acid comprises a nucleic acid molecule of at least 10 nucleotides, the molecule having at least 75% sequence identity to a sequence selected from the group consisting of SEQ ID NOs:1–23, or the complement of the molecule, wherein any molecule that is 10 to 30 nucleotides in length, in combination with an appropriate second nucleic acid molecule, under standard amplification conditions, generates an amplification product from M. paratuberculosis nucleic acid but does not generate an amplification product from nucleic acid of any of the organisms selected from the group consisting of Ralstonia solanacearum, Sinorhizobium meliloti, Homo sapiens, Mesorhizobium loti, Oryza sativa, Drosophila melanogaster, Rhizobium leguminosarum, Xylella fastidiosa, Deinococcus radiodurans, Achromobacter cycloclastes, Candida cylindracea, Streptomyces lavendulae, Streptococcus pneumoniae, Mycobacterium tuberculosis, Pseudomonas aeruginosa, Sus scrofa, Mycobacterium leprae, Streptomyces coelicolor, Pseudomonas sp., Thauera aromatica, Brucella melitensis, Streptomyces noursei, Rhizobium meliloti, Synechococcus elongates, Rhodobacter capsulatus, Agrobacterium tumefaciens, Mycobacterium smegmatis, Drosophila virilis, Mus musculus, Leishmania major, Botrytis cinerea, Caulobacter crescentus, Rhodobacter sphaeroides, Spermatozopsis similes, Giardia intestinalis, Triticum aestivum, Bovine herpesvirus, Streptomyces sp., Streptomyces peucetius, Rhizobium sp., Haloferax volcanii, Streptomyces viridochromogenes, Felis catus, Xanthomonas campestris, Thermotoga maritime, Thermotoga neapolitana, Frankia alni, Halobacterium NRC-1, Glycine max, Leishmania tarentolae, Neisseria meningitides, Escherichia coli, Caenorhabditis elegans, Leishmania mexicana, Zea mays, Ictalurid herpesvirus, Rattus norvegicus, Arabidopsis thaliana, Pseudomonasfluorescens, Pantoea agglomerans, Erwinia uredovora, Pantoea ananatis, Streptomyces hygroscopicus, Rickettsia typhi, Pseudomonas cruciviae, Xanthomonas albilineans, Halobacterium salinarium, Micronzonospora griseorubida, Pseudomonas paucimobilis, Streptomyces lividans, Pyrobaculum aerophilum, Sinorhizobium meliloti, Mesorhizobium loti, Bacillus halodurans, Trypanosoma rangeli, Trypanosoma minasense, Trypanosoma leeuwenhoeki, and Brassica napus.

In another aspect, the invention provides for vectors comprising a nucleic acid of the invention. Host cells comprising such a vector are further provided by the invention.

In yet another aspect, the invention provides for isolated polypeptides encoded by the nucleic acids of the invention. For example, the nucleic acid molecule having the sequence of SEQ ID NO:1 can encode a polypeptide having an amino acid sequence of SEQ ID NO:24; the nucleic acid molecule having the sequence of SEQ ID NO:2 can encode a polypeptide having an amino acid sequence of SEQ ID NO:25; the nucleic acid molecule having the sequence of SEQ ID NO:3 can encode a polypeptide having an amino acid sequence of SEQ ID NO:26; the nucleic acid molecule having the sequence of SEQ ID NO:4 can encode a polypeptide having an amino acid sequence of SEQ ID NO:27; the nucleic acid molecule having the sequence of SEQ ID NO:5 can encode a polypeptide having an amino acid sequence of SEQ ID NO:28; the nucleic acid molecule having the sequence of SEQ ID NO:6 can encode a polypeptide having an amino acid sequence of SEQ ID NO:29; the nucleic acid molecule having the sequence of SEQ ID NO:7 can encode a polypeptide having an amino acid sequence of SEQ ID NO:30; the nucleic acid molecule having the sequence of SEQ ID NO:8 can encode a polypeptide having an amino acid sequence of SEQ ID NO:31; the nucleic acid molecule having the sequence of SEQ ID NO:9 can encode a polypeptide having an amino acid sequence of SEQ ID NO:32; the nucleic acid molecule having the sequence of SEQ ID NO:10 can encode a polypeptide having an amino acid sequence of SEQ ID NO:33; the nucleic acid molecule having the sequence of SEQ ID NO:11 can encode a polypeptide having an amino acid sequence of SEQ ID NO:34; the nucleic acid molecule having the sequence of SEQ ID NO:12 can encode a polypeptide having an amino acid sequence of SEQ ID NO:35; the nucleic acid molecule having the sequence of SEQ ID NO:13 can encode a polypeptide having an amino acid sequence of SEQ ID NO:36; the nucleic acid molecule having the sequence of SEQ ID NO:14 can encode a polypeptide having an amino acid sequence of SEQ ID NO:37; the nucleic acid molecule having the sequence of SEQ ID NO:15 can encode a polypeptide having an amino acid sequence of SEQ ID NO:38; the nucleic acid molecule having the sequence of SEQ ID NO:16 can encode a polypeptide having an amino acid sequence of SEQ ID NO:39; the nucleic acid molecule having the sequence of SEQ ID NO:17 can encode a polypeptide having an amino acid sequence of SEQ ID NO:40; the nucleic acid molecule having the sequence of SEQ ID NO:18 can encode a polypeptide having an amino acid sequence of SEQ ID NO:41; the nucleic acid molecule having the sequence of SEQ ID NO:19 can encode a polypeptide having an amino acid sequence of SEQ ID NO:42; the nucleic acid molecule having the sequence of SEQ ID NO:20 can encode a polypeptide having an amino acid sequence of SEQ ID NO:43; the nucleic acid molecule having the sequence of SEQ ID NO:21 can encode a polypeptide having an amino acid sequence of SEQ ID NO:44; and the nucleic acid molecule having the sequence of SEQ ID NO:22 can encode a polypeptide having an amino acid sequence of SEQ ID NO:45.

In another aspect, the invention provides articles of manufacture that include one or more polypeptides of the invention. In still another aspect of the invention, there are provided antibodies that have specific binding affinity for a polypeptide of the invention.

In another aspect, the invention provides for methods for detecting the presence or absence of *M. paratuberculosis* in a biological sample. Such methods include contacting the biological sample with one or more of the nucleic acids of the invention (e.g., SEQ ID NOs:1–23) under standard amplification conditions, wherein an amplification product is produced if *M. paratuberculosis* nucleic acid is present in the biological sample; and detecting the presence or absence of the amplification product. Generally, the presence of the amplification product indicates the presence of *M. paratuberculosis* in the biological sample, and the absence of the amplification product indicates the absence of *M. paratuberculosis* in the biological sample. Representative animals from which the biological sample can be derived include a cow, a sheep, a goat, a rabbit, a deer, an antelope, or a bison. Representative biological samples include a fecal sample and a milk sample. Further, representative nucleic acids that can be used in the above-described methods include those having the sequence of SEQ ID NO:46–101.

In another aspect, the invention provides methods for detecting the presence or absence of *M. paratuberculosis* in a biological sample. Such methods include contacting the biological sample with one or more of the nucleic acids of the invention (e.g., SEQ ID NOs:1–23) under hybridization conditions, wherein a hybridization complex is produced if *M. paratuberculosis* nucleic acid molecules are present in the biological sample; and detecting the presence or absence of the hybridization complex. Generally, the presence of the hybridization complex indicates the presence of *M. paratuberculosis* in the biological sample, and the absence of the hybridization complex indicates the absence of *M. paratuberculosis* in the biological sample. Typically, nucleic acids present in the biological sample are electrophoretically separated. Such electrophoretically separated nucleic acids can be attached to a solid support. Representative solid supports include nylon membranes and nitrocellulose membranes. Further, one or more nucleic acids can be labeled. Representative biological samples include a fecal sample, a milk sample, and a blood sample.

In another aspect, the invention provides methods for detecting the presence or absence of *M. paratuberculosis* in a biological sample. Such methods include contacting the biological sample with a polypeptide of the invention (e.g., SEQ ID NOs:24–45), wherein a polypeptide-antibody complex is produced if an antibody having specific binding affinity for the polypeptide is present in the sample; and detecting the presence or absence of the polypeptide-antibody complex. Typically, the presence of the polypeptide-antibody complex indicates the presence of *M. paratuberculosis* in the biological sample, and the absence of the polypeptide-antibody complex indicates the absence of *M. paratuberculosis* in the biological sample. Polypeptides used in the above-described method can be attached to a solid support. Further, representative biological samples include a blood sample and a milk sample.

In yet another aspect, the invention provides for methods for detecting the presence or absence of *M. paratuberculosis* in a biological sample. Such methods include contacting the biological sample with an antibody of the invention (e.g., an antibody having specific binding affinity for a polypeptide having an amino acid sequence of SEQ ID NOs:24–45), wherein an antibody-polypeptide complex is produced if a polypeptide is present in the biological sample for which the antibody has specific binding affinity, and detecting the presence or absence of the antibody-polypeptide complex. Generally, the presence of the antibody-polypeptide complex indicates the presence of *M. paratuberculosis* in the biological sample, and the absence of the antibody-polypeptide complex indicates the absence of *M. paratuberculosis* in the biological sample. Antibodies used in the above-described methods can be bound to a solid support. Representative biological samples that can be used in the above-described methods include a blood sample and a milk sample.

In still another aspect of the invention, there are provided methods of preventing infection by *M. paratuberculosis* in an animal. Such methods include administering a compound to the animal, wherein the compound comprises a polypeptide of the invention (e.g., SEQ ID NOs:24–45). Alternatively, such methods include administering a compound to the animal, wherein the compound comprises a nucleic acid of the invention (e.g., a nucleic acid comprising a nucleic acid molecule having at least 75% sequence identity to SEQ ID NOs:1–23). Typically, the compound immunizes the animal against *M. paratuberculosis*.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

FIG. 2 shows the sequences of *M. paratuberculosis*-specific nucleic acid molecules (SEQ ID NOS:1–23).

FIG. 3 shows the polypeptide sequences (SEQ ID NOs: 24–45) encoded by *M. paratuberculosis*-specific nucleic acids. An * indicates a stop codon.

FIG. 4 shows representative nucleic acid molecules having 75%, 80%, 85%, 90%, 95%, and 99% sequence identity to SEQ ID NO:1 (SEQ ID NOs:102–107, respectively).

Like reference symbols in the various drawings indicate like elements.

DETAILED DESCRIPTION

Figure 1:
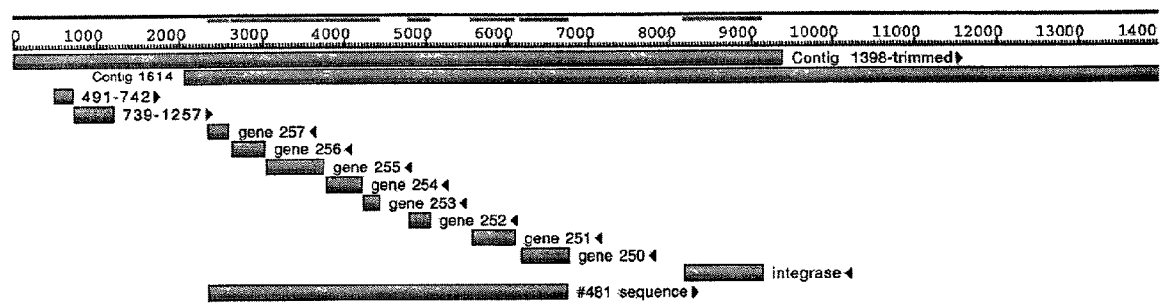
FIG. 1 is a sequence alignment schematic showing positions of predicted coding sequences relative to assembled contig fragments. Alignments of contig 1614 and a trimmed fragment of the 94-kb contig 1398 are shown along with each predicted coding sequence listed in Table 4. Note that the core region of genes 250 to 257 is well separated from neighboring coding regions. The integrase gene upstream of gene 250 is also designated gene 249.

The close genetic relationship between M. paratuberculosis and M. avium has made difficult the identification of nucleic acids and polypeptides specific to M. paratuberculosis that can be used with high sensitivity and specificity to detect M. paratuberculosis. The present invention provides nucleic acid molecules that are unique to M. paratuberculosis. The invention also provides the M. paratuberculosis-specific polypeptides encoded by the nucleic acid molecules of the invention, and antibodies having specific binding affinity for the M. paratuberculosis-specific polypeptides. The nucleic acid molecules, polypeptides, and antibodies of the invention can be used in methods of the invention to detect M. paratuberculosis in a sample. The invention additionally provides methods of preventing a M. paratuberculosis infection in an animal.

Isolated M. paratuberculosis-specific Nucleic Acid Molecules

The present invention is based, in part, on the identification of nucleic acid molecules that are unique to M. paratuberculosis. These nucleic acid molecules are herein referred to as "M. paratuberculosis-specific" nucleic acid molecules. Particular nucleic acid molecules of the invention include the sequences shown in SEQ ID NOs:1–23. As used herein, the term "nucleic acid molecule" can include DNA molecules and RNA molecules and analogs of the DNA or RNA molecule generated using nucleotide analogs. A nucleic acid molecule of the invention can be single-stranded or double-stranded, and the strandedness will depend upon its intended use.

The invention further encompasses nucleic acid molecules that differ from the nucleotide sequence of SEQ ID NOs:1–23. Nucleic acid molecules of the invention include molecules that are at least 10 nucleotides in length and that have at least 75% sequence identity (e.g., at least 80%, 85%, 90%, 95%, or 99% sequence identity) to any of SEQ ID NOs:1–23. The full-length sizes of each of the novel M. paratuberculosis-specific nucleic acid molecules having the sequences shown in SEQ ID NOs:1–23 are indicated in Table 1. Nucleic acid molecules that differ in sequence from the nucleic acid sequences shown in SEQ ID NOs:1–23 can be generated by standard techniques, such as site-directed mutagenesis or PCR-mediated mutagenesis. In addition, nucleotide changes can be introduced randomly along all or part of the M. paratuberculosis-specific nucleic acid molecule, such as by saturation mutagenesis. Alternatively, nucleotide changes can be introduced into a sequence by chemically synthesizing a nucleic acid molecule having such changes.

TABLE 1

Sizes of M. paratuberculosis-specific nucleic acid molecules and polypeptides

| Gene | Nucleic Acid (bp) | SEQ ID NO: | Polypeptide (amino acids) | SEQ ID NO: |
|---|---|---|---|---|
| 10 | 969 | 1 | 322 | 24 |
| 11 | 576 | 2 | 191 | 25 |
| 38 | 522 | 3 | 173 | 26 |
| 56 | 582 | 4 | 193 | 27 |
| 57 | 311 | 5 | 103 | 28 |
| 128 | 576 | 6 | 191 | 29 |
| 135 | 474 | 7 | 157 | 30 |
| 159 | 558 | 8 | 185 | 31 |
| 217 | 321 | 9 | 106 | 32 |
| 218 | 2508 | 10 | 835 | 33 |
| 219 | 264 | 11 | 87 | 34 |
| 228 | 1110 | 12 | 369 | 35 |
| 240 | 672 | 13 | 223 | 36 |
| 241 | 372 | 14 | 123 | 37 |
| 250 | 600 | 15 | 199 | 38 |
| 251 | 540 | 16 | 179 | 39 |
| 252 | 291 | 17 | 96 | 40 |
| 253 | 225 | 18 | 74 | 41 |
| 254 | 441 | 19 | 146 | 42 |
| 255 | 726 | 20 | 241 | 43 |
| 256 | 426 | 21 | 141 | 44 |
| 257 | 279 | 22 | 87 | 45 |

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It will be appreciated that a single sequence can align differently with other sequences and hence, can have different percent sequence identity values over each aligned region. It is noted that the percent identity value is usually rounded to the nearest integer. For example, 78.1%, 78.2%, 78.3%, and 78.4% are rounded down to 78%, while 78.5%, 78.6%, 78.7%, 78.8%, and 78.9% are rounded up to 79%. It is also noted that the length of the aligned region is always an integer.

The alignment of two or more sequences to determine percent sequence identity is performed using the algorithm described by Altschul et al. (1997, Nucleic Acids Res., 25:3389–3402) as incorporated into BLAST (basic local alignment search tool) programs, available at ncbi.nlm.nih.gov on the World Wide Web. BLAST searches can be performed to determine percent sequence identity between a M. paratuberculosis-specific nucleic acid molecule of the invention and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence of the invention and another sequence, the default parameters of the respective programs are used. Sequence analysis of the M. paratuberculosis-specific nucleic acid sequences as performed herein used BLAST version 2.2.2 (updated on Dec. 14, 2001).

The sequences of representative nucleic acids of the invention having 75%, 80%, 85%, 90%, 95%, and 99% sequence identity to SEQ ID NO:1 are shown in FIG. 4 (SEQ ID NOs:102–107, respectively). Such sequences can be generated using a computer or by hand. The nucleic acid sequences shown in SEQ ID NOs:102–107 were generated by hand by randomly changing 25 nucleotides out of every 100 nucleotides of SEQ ID NO:1, 2 out of every 10, 15 out of every 100, 1 out of every 10, 5 out of every 100, or 1 nucleotide out of every 100 nucleotides of SEQ ID NO:1, respectively. By "changing," it is meant that the nucleotide at a particular position is replaced randomly with one of the other three nucleotides. It is apparent to those of ordinary skill in the art that any nucleic acid molecule within the scope of the invention can be generated using the same method described herein (i.e., by similarly changing nucleotides within the sequence of SEQ ID NOs:1–23).

Nucleic acid molecules of the invention between about 10 and about 30 nucleotides in length will, in combination with an appropriate second nucleic acid molecule (e.g., an oligonucleotide primer) and under standard amplification conditions, generate an amplification product in the presence of *M. paratuberculosis* nucleic acid but will not generate an amplification product in the presence of nucleic acid from an organism other than *M. paratuberculosis*. As used herein, "standard amplification conditions" refer to the basic components of an amplification reaction mix, and cycling conditions that include multiple cycles of denaturing the template nucleic acid, annealing the oligonucleotide primers to the template nucleic acid, and extension of the primers by the polymerase to produce an amplification product (see, for example, U.S. Pat. Nos. 4,683,195; 4,683,202; 4,800,159; and 4,965,188. The basic components of an amplification reaction mix generally include, for example, about 10–25 nmole of each of the four deoxynucleoside triphosphates, (e.g., dATP, dCTP, dTTP, and dGTP, or analogs thereof), 10–100 pmol of primers, template nucleic acid, and a polymerase enzyme. The reaction components are generally suspended in a buffered aqueous solution having a pH of between about 7 and about 9. The aqueous buffer can further include one or more co-factors (e.g., $Mg^{2+}$, $K^+$) required by the polymerase. Additional components such as DMSO are optional. Template nucleic acid is typically denatured at a temperature of at least about 90° C., and extension from primers is typically performed at a temperature of at least about 72° C.

The annealing temperature can be used to control the specificity of amplification. The temperature at which primers anneal to template nucleic acid must be below the Tm of each of the primers, but high enough to avoid non-specific annealing of primers to the template nucleic acid. The Tm is the temperature at which half of the DNA duplexes have separated into single strands, and can be predicted for an oligonucleotide primer using the formula provided in section 11.46 of Sambrook et al. (1989, *Molecular Cloning: A Laboratory Manual*, 2nd Ed., Cold Spring Harbor Laboratory Press, Cold Spring Harbor, N.Y.). Non-specific amplification products are detected as bands on a gel that are not the size expected for the correct amplification product. The annealing temperature used in amplification reactions described herein to demonstrate that the claimed nucleic acid molecules are *M. paratuberculosis*-specific was 55° C. and 60° C. for nucleic acids isolated from bacteria or from a biological sample, respectively. It can be appreciated by those of skill in the art that appropriate positive and negative controls should be performed with every set of amplification reactions to avoid uncertainties related to contamination and/or non-specific annealing of oligonucleotide primers and extension therefrom.

An appropriate second nucleic acid molecule is generally an oligonucleotide primer that can act in combination with a nucleic acid molecule of the invention, specifically for example a 10 to 30 nucleotide-long nucleic acid molecule of the invention, under appropriate amplification conditions to generate an amplification product in the presence of *M. paratuberculosis* nucleic acid. In order for a second nucleic acid molecule to act in combination with a nucleic acid molecule of the invention to generate an amplification product, the two molecules must anneal to opposite strands of the template nucleic acid, and should be an appropriate distance from one another such that the polymerase can effectively polymerize across the region and such that the amplification product can be readily detected using, for example, electrophoresis. Oligonucleotide primers can be designed using, for example, a computer program such as OLIGO (Molecular Biology Insights Inc., Cascade, Colo.) to assist in designing primers that have similar melting temperatures. Typically, oligonucleotide primers can be 10 to 50 nucleotides in length (e.g., 12, 14, 16, 18, 20, 22, 24, 26, 28, 30, 32, 34, 36, 38, 40, 42, 44, 46, 48, or 50 nucleotides in length). Representative pairs of oligonucleotide primers that were used to amplify each of the *M. paratuberculosis*-specific nucleic acid molecules of the invention are shown in Tables 3 and 6 (SEQ ID NOs:46–101). Alternatively, the nucleic acid molecules having the sequences shown in SEQ ID NOs:1–23 can be used to design a pair of oligonucleotide primers. Oligonucleotides of the invention can be obtained by restriction enzyme digestion of *M. paratuberculosis*-specific nucleic acid molecules or can be prepared by standard chemical synthesis and other known techniques.

As used herein, an organism other than *M. paratuberculosis* refers to any organism that is not *M. paratuberculosis*. Generally, only relevant organisms are used in amplification reactions to examine the specificity of a 10 to 30 nucleotide-long nucleic acid molecule of the invention. Particularly relevant organisms include, without limitation, *Ralstonia solanacearum, Sinorhizobium meliloti, Homo sapiens, Mesorhizobium loti, Oryza sativa, Drosophila melanogaster, Rhizobium leguminosarum, Xylella fastidiosa, Deinococcus radiodurans, Achromobacter cycloclastes, Candida cylindracea, Streptomyces lavendulae, Streptococcus pneumoniae, Mycobacterium tuberculosis, Pseudomonas aeruginosa, Sus scrofa, Mycobacterium leprae, Streptomyces coelicolor, Pseudomonas* sp. (e.g., strain CA-10), *Thauera aromatica, Brucella melitensis, Streptomyces noursei, Rhizobium meliloti, Synechococcus elongates, Rhodobacter capsulatus, Agrobacterium tumefaciens, Mycobacterium smegmatis, Drosophila virilis, Mus musculus, Leishmania major, Botrytis cinerea, Caulobacter crescentus, Rhodobacter sphaeroides, Spermatozopsis similes, Giardia intestinalis, Triticum aestivum, Bovine herpesvirus, Streptomyces* sp. (e.g., strain MA-6548), *Streptomyces peucetius, Rhizobium* sp. (e.g., strain NGR-234), *Haloferax volcanii, Streptomyces viridochromogenes, Felis catus, Xanthomonas campestris, Thermotoga maritime, Thermotoga neapolitana, Frankia alni, Halobacterium* NRC-1 (ATCC Accession No. 700922), *Glycine max, Leishmania tarentolae, Neisseria meningitides, Escherichia coli, Caenorhabditis elegans, Leishmania mexicana, Zea mays, Ictalurid herpesvirus, Rattus norvegicus, Arabidopsis thaliana, Pseudomonas fluorescens, Pantoea agglomerans, Erwinia uredovora, Pantoea ananatis, Streptomyces hygroscopicus, Rickettsia typhi, Pseudomonas cruciviae, Xanthomonas albilineans, Halobacterium salinarium, Micromonospora griseorubida, Pseudomonas paucimobilis, Streptomyces lividans, Pyrobaculum aerophilum, Sinorhizobium meliloti, Mesorhizobium loti, Bacillus halodurans, Trypanosoma rangeli, Trypanosoma minasense, Trypanosoma leeuwenhoeki,* and *Brassica napus*. A 10 to 30 nucleotide-long nucleic acid molecule of the invention in combination with an appropriate second oligonucleotide primer will not generate an amplification product from nucleic acid of one or more of these other organisms.

As used herein, an "isolated" nucleic acid molecule is a nucleic acid molecule that is separated from other nucleic acid molecules that are usually associated with the isolated nucleic acid molecule. Thus, an "isolated" nucleic acid molecule includes, without limitation, a nucleic acid molecule that is free of sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA, or genomic library) or a portion of a gel (e.g., agarose, or polyacrylamine) containing restriction-digested genomic DNA is not to be considered an isolated nucleic acid.

Isolated nucleic acid molecules of the invention can be obtained using techniques routine in the art. For example, isolated nucleic acids within the scope of the invention can be obtained using any method including, without limitation, recombinant nucleic acid technology, and/or the polymerase chain reaction (PCR). General PCR techniques are described, for example in *PCR Primer: A Laboratory Manual,* Dieffenbach & Dveksler, Eds., Cold Spring Harbor Laboratory Press, 1995. Recombinant nucleic acid techniques include, for example, restriction enzyme digestion and ligation, which can be used to isolate a nucleic acid molecule of the invention. Isolated nucleic acids of the invention also can be chemically synthesized, either as a single nucleic acid molecule or as a series of oligonucleotides. In addition, isolated nucleic acid molecules of the invention also can be obtained by mutagenesis. For example, and isolated nucleic acid that shares identity with an art known ECE sequence can be mutated using common molecular cloning techniques (e.g., site-directed mutagenesis). Possible mutations include, without limitation, deletions, insertions, substitutions, and combinations thereof.

Vectors containing *M. paratuberculosis*-specific nucleic acid molecules also are provided by the invention. Vectors, including expression vectors, suitable for use in the present invention are commercially available and/or produced by recombinant DNA technology methods routine in the art. A vector containing a *M. paratuberculosis*-specific nucleic acid molecule can have elements necessary for expression operably linked to such a *M. paratuberculosis*-specific nucleic acid, and further can include sequences such as those encoding a selectable marker (e.g., an antibiotic resistance gene), and/or those that can be used in purification of a *M. paratuberculosis*-specific polypeptide (e.g., 6×His tag).

Elements necessary for expression include nucleic acid sequences that direct and regulate expression of nucleic acid coding sequences. One example of an element necessary for expression is a promoter sequence, for example, a *M. paratuberculosis*-specific promoter (e.g., from the same coding sequence being expressed or from a different coding sequence) or a non-*M. paratuberculosis*-specific promoter. Elements necessary for expression also can include introns, enhancer sequences, response elements, or inducible elements that modulate expression of a *M. paratuberculosis*-specific nucleic acid. Elements necessary for expression can be of bacterial, yeast, insect, mammalian, or viral origin and vectors can contain a combination of elements from different origins. Elements necessary for expression are described, for example, in Goeddel, 1990, *Gene Expression Technology: Methods in Enzymology,* 185, Academic Press, San Diego, Calif. As used herein, operably linked means that a promoter and/or other regulatory element(s) are positioned in a vector relative to a *M. paratuberculosis*-specific nucleic acid in such a way as to direct or regulate expression of the *M. paratuberculosis*-specific nucleic acid. Many methods for introducing nucleic acids into cells, both in vivo and in vitro, are well known to those skilled in the art and include, without limitation, calcium phosphate precipitation, electroporation, heat shock, lipofection, microinjection, and viral-mediated nucleic acid transfer.

Another aspect of the invention pertains to host cells into which a vector of the invention, e.g., an expression vector, or an isolated nucleic acid molecule of the invention has been introduced. The term "host cell" refers not only to the particular cell but also to the progeny or potential progeny of such a cell. A host cell can be any prokaryotic or eukaryotic cell. For example, *M. paratuberculosis*-specific nucleic acids can be expressed in bacterial cells such as *E. coli,* or in insect cells, yeast or mammalian cells (such as Chinese hamster ovary cells (CHO) or COS cells). Other suitable host cells are known to those skilled in the art.

Vectors containing nucleic acid molecules unique to *M. paratuberculosis* were deposited with the American Type Culture Collection (ATCC), 10801 University Boulevard Manassas, Va. 20110, on Apr. 3, 2002, and assigned Accession Numbers PTA-4199, and PTA-4200. Each deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

Purified *M. paratuberculosis* Polypeptides

One aspect of the invention pertains to purified *M. paratuberculosis*-specific polypeptides, as well as polypeptide fragments. A "*M. paratuberculosis*-specific polypeptide" refers to a polypeptide encoded by a nucleic acid molecule that is unique to *M. paratuberculosis* (e.g., *M. paratuberculosis*-specific nucleic acid molecules, for example, those having the sequence shown in SEQ ID NOs:1–23). Predicted amino acid sequences encoded by novel *M. paratuberculosis*-specific nucleic acids of the invention are shown in SEQ ID NOs:24–45.

The term "purified" polypeptide as used herein refers to a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the proteins and naturally occurring molecules with which it is naturally associated. Since a polypeptide that is chemically synthesized is, by nature, separated from the components that naturally accompany it, a synthetic polypeptide is "purified."

*M. paratuberculosis*-specific polypeptides can be purified from natural sources (e.g., a biological sample) by known methods such as DEAE ion exchange, gel filtration, and hydroxyapatite chromatography. A purified *M. paratuberculosis*-specific polypeptide also can be obtained by expressing a *M. paratuberculosis*-specific nucleic acid in an expression vector, for example. In addition, a purified *M. paratuberculosis*-specific polypeptide can be obtained by chemical synthesis. The extent of purity of a *M. paratuberculosis*-specific polypeptide can be measured using any appropriate method, e.g., column chromatography, polyacrylamide gel electrophoresis, or HPLC analysis.

In addition to naturally-occurring *M. paratuberculosis*-specific polypeptides, the skilled artisan will further appreciate that changes can be introduced into a nucleic acid molecule (e.g., those having the sequence shown in SEQ ID NOs:1–23) as discussed herein, thereby leading to changes in the amino acid sequence of the encoded polypeptide. For example, changes can be introduced into *M. paratuberculosis*-specific nucleic acid coding sequences leading to conservative and/or non-conservative amino acid substitutions at one or more amino acid residues. A "conservative amino acid substitution" is one in which one amino acid residue is replaced with a different amino acid residue having a similar side chain. Similarity between amino acid residues has been assessed in the art. For example, Dayhoff et al. (1978, in *Atlas of Protein Sequence and Structure*, Vol. 5, Suppl. 3, pp 345–352) provides frequency tables for amino acid substitutions that can be employed as a measure of amino acid similarity. A non-conservative substitution is one in which an amino acid residue is replaced with an amino acid residue that does not have a similar side chain.

The invention also provides for chimeric or fusion polypeptides. As used herein, a "chimeric" or "fusion" polypeptide includes a *M. paratuberculosis*-specific polypeptide operatively linked to a heterologous polypeptide. 4) A heterologous polypeptide can be at either the N-terminus or C-terminus of the *M. paratuberculosis*-specific polypeptide. Within a chimeric or fusion polypeptide, the term "operatively linked" is intended to indicate that the two polypeptides are encoded in-frame relative to one another. In a fusion polypeptide, the heterologous polypeptide generally has a desired property such as the ability to purify the fusion polypeptide (e.g., by affinity purification). A chimeric or fusion polypeptide of the invention can be produced by standard recombinant DNA techniques, and can use commercially available vectors.

A polypeptide commonly used in a fusion polypeptide for purification is glutathione S-transferase (GST), although numerous other polypeptides are available and can be used. In addition, a proteolytic cleavage site can be introduced at the junction between a *M. paratuberculosis*-specific polypeptide and a non-*M. paratuberculosis*-specific polypeptide to enable separation of the two polypeptides subsequent to purification of the fusion polypeptide. Enzymes that cleave such proteolytic sites include Factor Xa, thrombin, or enterokinase. Representative expression vectors encoding a heterologous polypeptide that can be used in affinity purification of a *M. paratuberculosis* polypeptide include pGEX (Pharmacia Biotech Inc; Smith & Johnson, 1988, *Gene*, 67:31–40), pMAL (New England Biolabs, Beverly, Mass.) and pRIT5 (Pharmacia, Piscataway, N.J.).

Anti-*M. paratuberculosis*-specific Antibodies

Another aspect of the invention relates to anti-*M. paratuberculosis*-specific antibodies. The term "anti-*M. paratuberculosis*-specific antibodies" as used herein refers to immunoglobulin molecules and immunologically active portions of immunoglobulin molecules that have specific binding affinity for a *M. paratuberculosis*-specific polypeptide. The invention provides polyclonal and monoclonal antibodies that have specific binding affinity for *M. paratuberculosis*-specific polypeptides. The sequences of numerous *M. paratuberculosis*-specific polypeptides that can be used to generate anti-*M. paratuberculosis*-specific antibodies are disclosed herein (e.g., SEQ ID NOs:24–45). Examples of immunologically active portions of immunoglobulin molecules include F(ab) and F(ab')$_2$ fragments, which can be generated by treating an immunoglobulin molecule with an enzyme such as pepsin. As used herein, an antibody that has "specific binding affinity" for a *M. paratuberculosis*-specific polypeptide is an antibody that binds a *M. paratuberculosis*-specific polypeptide but does not bind a non-*M. paratuberculosis*-specific polypeptides. A non-*M. paratuberculosis*-specific polypeptide as used herein refers to a polypeptide that may or may not be found in *M. paratuberculosis*, but is found in at least one other organism besides *M. paratuberculosis*.

A purified *M. paratuberculosis*-specific polypeptide or a fragment thereof can be used as an immunogen to generate polyclonal or monoclonal antibodies that have specific binding affinity for *M. paratuberculosis*-specific polypeptides. Such antibodies can be generated using standard techniques as described herein. Full-length *M. paratuberculosis*-specific polypeptides (see Table 1) or, alternatively, antigenic fragments of *M. paratuberculosis*-specific polypeptides can be used as immunogens. An antigenic fragment of a *M. paratuberculosis*-specific polypeptide usually includes at least 8 (e.g., 10, 15, 20, or 30) amino acid residues of a *M. paratuberculosis*-specific polypeptide (e.g., having the sequence shown in SEQ ID NOs:23–45), and encompasses an epitope of a *M. paratuberculosis*-specific polypeptide such that an antibody (e.g., polyclonal or monoclonal) raised against the antigenic fragment has specific binding affinity for a *M. paratuberculosis*-specific polypeptide.

Antibodies are typically prepared by first immunizing a suitable animal (e.g., a rabbit, a goat, a mouse or another mammal) with an immunogenic preparation. An appropriate immunogenic preparation can contain, for example, a recombinantly expressed or chemically synthesized *M. paratuberculosis*-specific polypeptide, of a fragment thereof. The preparation can further include an adjuvant, such as Freund's complete or incomplete adjuvant, or similar immunostimulatory agent. Immunization of a suitable animal with an immunogenic *M. paratuberculosis*-specific polypeptide preparation induces a polyclonal anti-*M. paratuberculosis*-specific antibody response.

The titer of the anti-*M. paratuberculosis*-specific antibody in the immunized animal can be monitored over time by standard techniques, such as with an enzyme-linked immunosorbent assay (ELISA) using immobilized *M. paratuberculosis*-specific polypeptides. If desired, the antibody molecules directed against *M. paratuberculosis*-specific polypeptides can be isolated from the animal (e.g., from the blood) and further purified by well-known techniques such as protein A chromatography to obtain the IgG fraction.

At an appropriate time after immunization, e.g., when the anti-*M. paratuberculosis*-specific antibody titers are highest, antibody-producing cells can be obtained from the animal and used to prepare monoclonal antibodies by standard techniques, such as the hybridoma technique originally described by Kohler & Milstein (1975, *Nature*, 256:495–497), the human B cell hybridoma technique (Kozbor et al., 1983, *Immunol. Today*, 4:72), or the EBV-hybridoma technique (Cole et al., 1985, *Monoclonal Antibodies and Cancer Therapy*, Alan R. Liss, Inc., pp. 77–96). The technology for producing various monoclonal antibody hybridomas is well known (see, generally, *Current Protocols* in *Immunology*, 1994, Coligan et al. (Eds.), John Wiley & Sons, Inc., New York, N.Y.). Briefly, an immortal cell line (e.g., a myeloma cell line) is fused to lymphocytes (e.g., splenocytes) from an animal immunized with an immunogenic *M. paratuberculosis*-specific polypeptide as described above, and the culture supernatants of the resulting hybridoma cells are screened to identify a hybridoma producing a monoclonal antibody that has specific binding affinity for the *M. paratuberculosis*-specific polypeptide.

Any of the well-known protocols used for fusing lymphocytes and immortalized cell lines can be applied for the purpose of generating an anti-*M. paratuberculosis*-specific monoclonal antibody (see, e.g., *Current Protocols in Immunology,* supra; Galfre et al., 1977, *Nature,* 266:55052; R. H. Kenneth, in *Monoclonal Antibodies: A New Dimension In Biological Analyses,* Plenum Publishing Corp., New York, N.Y., 1980; and Lemer, 1981, *Yale J. Biol. Med.,* 54:387–402). Moreover, the ordinary skilled worker will appreciate that there are many variations of such methods that also would be useful. Typically, the immortal cell line is derived from the same species as the lymphocytes. For example, murine hybridomas can be made by fusing lymphocytes from a mouse immunized with an immunogenic preparation with an immortalized mouse cell line, e.g., a myeloma cell line that is sensitive to culture medium containing hypoxanthine, aminopterin and thymidine ("HAT medium"). Any of a number of ATCC-available myeloma cell lines can be used as a fusion partner according to standard techniques, e.g., the P3-NS1/1-Ag4–1, P3-x63-Ag8.653 or Sp2/O-Ag14 myeloma lines. Typically, HAT-sensitive mouse myeloma cells are fused to mouse splenocytes using polyethylene glycol (PEG). Hybridoma cells resulting from the fusion are then selected using HAT medium. Hybridoma cells producing a monoclonal antibody are detected by screening the hybridoma culture supernatants for antibodies that bind *M. paratuberculosis*-specific polypeptides, e.g., using a standard ELISA assay.

As an alternative to preparing monoclonal antibody-secreting hybridomas, an anti-*M. paratuberculosis*-specific monoclonal antibody can be identified and isolated by screening a recombinant combinatorial immunoglobulin library (e.g., an antibody phage display library) with *M. paratuberculosis*-specific polypeptides. Immunoglobulin library members that have specific binding affinity for *M. paratuberculosis*-specific polypeptides can be isolated from such libraries. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display libraries can be found in, for example, U.S. Pat. No. 5,223,409; PCT Publication No. WO 92/20791; PCT Publication No. WO 93/01288; Hay et al., 1992, *Hum. Antibod. Hybridomas,* 3:81–85; Griffiths et al., 1993, *EMBO J.,* 12:725–734; and references therein.

Additionally, recombinant anti-*M. paratuberculosis*-specific antibodies, such as chimeric and humanized monoclonal antibodies, comprising both human and non-human portions, are within the scope of the invention. Such chimeric and humanized monoclonal antibodies can be produced by recombinant DNA techniques known in the art, for example using methods described in PCT Publication No. WO 87/02671; European Patent (EP) Application 184,187; U.S. Pat. No. 4,816,567; Better et al., 1988, *Science,* 240: 1041–1043; Shaw et al., 1988, *J. Natl. Cancer Inst.,* 80:1553–1559); U.S. Pat. No. 5,225,539; Verhoeyan et al., 1988, *Science,* 239:1534; Beidler et al., 1988, *J. Immunol.,* 141:4053–4060; and references therein.

An anti-*M. paratuberculosis*-specific antibody (e.g., a monoclonal antibody) can be used to isolate *M. paratuberculosis*-specific polypeptides by standard techniques, such as affinity chromatography or immunoprecipitation. An anti-*M. paratuberculosis*-specific antibody can facilitate the purification of natural *M. paratuberculosis*-specific polypeptides from cells and of recombinantly-produced *M. paratuberculosis*-specific polypeptides expressed in host cells. Moreover, an anti-*M. paratuberculosis*-specific antibody can be used to detect *M. paratuberculosis*-specific polypeptides (e.g., in a cellular lysate or cell supernatant) in order to evaluate the presence or absence of the *M. paratuberculosis*-specific polypeptides. Anti-*M. paratuberculosis*-specific antibodies can be used diagnostically to detect *M. paratuberculosis*-specific polypeptides, and hence, *M. paratuberculosis*, in a biological sample, e.g., to determine the infection status of an animal, or to determine the efficacy of a given treatment regimen.

Methods of Detecting *M. paratuberculosis*

The *M. paratuberculosis*-specific nucleic acid molecules and polypeptides, and the anti-*M. paratuberculosis*-specific antibodies described herein can be used in diagnostic assays for the detection of *M. paratuberculosis*. Diagnostic assays for determining the presence or absence of *M. paratuberculosis* are performed using a biological sample (e.g., fecal, blood, milk) to determine whether an animal has been exposed to or is infected with *M. paratuberculosis*. An exemplary method for detecting the presence or absence of *M. paratuberculosis* in a biological sample involves obtaining a biological sample from an animal and contacting the biological sample with an appropriate agent capable of detecting *M. paratuberculosis*-specific nucleic acids or polypeptides, or anti-*M. paratuberculosis*-specific antibodies.

The term "biological sample" is intended to include cells and biological fluids obtained from an animal. In one embodiment, a biological sample contains polypeptides from the animal. Alternatively, the biological sample can contain nucleic acid molecules from the animal, or the biological sample can contain antibodies from the animal. It should be understood that any biological sample in which *M. paratuberculosis*-specific nucleic acids or polypeptides, or anti-*M. paratuberculosis*-specific antibodies may be present can be utilized in the methods described herein.

In one embodiment, an agent for detecting the presence or absence of *M. paratuberculosis* in a biological sample is an isolated *M. paratuberculosis*-specific nucleic acid molecule of the invention. The presence of *M. paratuberculosis*-specific nucleic acids in a sample indicates the presence of *M. paratuberculosis* in the sample. Methods for detecting nucleic acids include, for example, PCR and nucleic acid hybridizations (e.g., Southern blot, Northern blot, or in situ hybridizations). Specifically, an agent can be one or more oligonucleotides (e.g., oligonucleotide primers) capable of amplifying *M. paratuberculosis*-specific nucleic acids using PCR. PCR methods generally include the steps of collecting a biological sample from an animal, isolating nucleic acid (e.g., DNA, RNA, or both) from the sample, and contacting the nucleic acid with one or more oligonucleotide primers that hybridize(s) with specificity to *M. paratuberculosis*-specific nucleic acid under conditions such that amplification of the *M. paratuberculosis*-specific nucleic acid occurs if *M. paratuberculosis* is present. In the presence of *M. paratuberculosis*, an amplification product corresponding to the *M. paratuberculosis*-specific nucleic acid is produced. Conditions for amplification of a nucleic acid and detection of an amplification product are known to those of skill in the art (see, e.g., *PCR Primer: A Laboratory Manual*, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188). Modifications to the original PCR also have been developed. For example, anchor PCR, RACE PCR, or ligation chain reaction (LCR) are additional PCR methods known in the art (see, e.g., Landegran et al., 1988, *Science*, 241:1077–1080; and Nakazawaet al., 1994, *Proc. Natl. Acad. Sci. USA*, 91:360–364).

Alternatively, an agent for detecting *M. paratuberculosis*-specific nucleic acids can be a labeled oligonucleotide probe capable of hybridizing to *M. paratuberculosis*-specific nucleic acids on a Southern blot. An oligonucleotide probe can be, for example, a *M. paratuberculosis*-specific nucleic acid molecule such as a nucleic acid molecule having the sequence shown in SEQ ID NO:1–22, or a fragment thereof. In the presence of *M. paratuberculosis*, a hybridization complex is produced between *M. paratuberculosis* nucleic acid and the oligonucleotide probe. Hybridization between nucleic acid molecules is discussed in detail in Sambrook et al. (1989, *Molecular Cloning: A Laboratory Manual, 2$^{nd}$ Ed.*, Cold Spring Harbor Laboratory Press, Cold Spring Harbor, N.Y.; Sections 7.37–7.57, 9.47–9.57, 11.7–11.8, and 11.45–11.57).

For oligonucleotide probes less than about 100 nucleotides, Sambrook et al. discloses suitable Southern blot conditions in Sections 11.45–11.46. The Tm between a sequence that is less than 100 nucleotides in length and a second sequence can be calculated using the formula provided in Section 11.46. Sambrook et al. additionally discloses prehybridization and hybridization conditions for a Southern blot that uses oligonucleotide probes greater than about 100 nucleotides (see Sections 9.47–9.52). Hybridizations with an oligonucleotide greater than 100 nucleotides generally are performed 15–25° C. below the Tm. The Tm between a sequence greater than 100 nucleotides in length and a second sequence can be calculated using the formula provided in Sections 9.50–9.51 of Sambrook et al. Additionally, Sambrook et al. recommends the conditions indicated in Section 9.54 for washing a Southern blot that has been probed with an oligonucleotide greater than about 100 nucleotides.

The conditions under which membranes containing nucleic acids are prehybridized and hybridized, as well as the conditions under which membranes containing nucleic acids are washed to remove excess and non-specifically bound probe can play a significant role in the stringency of the hybridization. Such hybridizations can be performed, where appropriate, under moderate or high stringency conditions. Such conditions are described, for example, in Sambrook et al. section 11.45–11.46. For example, washing conditions can be made more stringent by decreasing the salt concentration in the wash solutions and/or by increasing the temperature at which the washes are performed. In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium.

It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids, for example, from *M. paratuberculosis* and at least one organism other than *M. paratuberculosis*, under identical hybridization, washing, and exposure conditions. Preferably, the target nucleic acids (e.g., nucleic acids from *M. paratuberculosis* and at least one organism other than *M. paratuberculosis*) are on the same membrane. Representative Southern blot conditions are described in Example 3.

A nucleic acid molecule is deemed to hybridize to *M. paratuberculosis* nucleic acids but not to nucleic acids from an organism other than *M. paratuberculosis* if hybridization to nucleic acid from *M. paratuberculosis* is at least 5-fold (e.g., at least 6-fold, 7-fold, 8-fold, 9-fold, 10-fold, 20-fold, 50-fold, or 100-fold) greater than hybridization to nucleic acid from an organism other than *M. paratuberculosis*. The amount of hybridization can be quantitated directly on a membrane or from an autoradiograph using, for example, a PhosphorImager or a Densitometer (Molecular Dynamics, Sunnyvale, Calif.). It can be appreciated that useful primers and probes of the invention include primers and probes that anneal and hybridize, respectively, to nucleic acids of organisms other than *M. paratuberculosis* provided that such nucleic acids are not typically present in the relevant test animals. For example, the fact that a particular primer or probe anneals or hybridizes, respectively, to human nucleic acid does not diminish the value of that primer or probe for detecting the presence or absence of *M. paratuberculosis* in ruminants, since ruminants typically are not contaminated with human nucleic acid.

In addition, anti-*M. paratuberculosis*-specific antibodies provided by the invention can be used as agents to detect the presence or absence of *M. paratuberculosis*-specific polypeptides in a biological sample. The presence of *M. paratuberculosis*-specific polypeptides is an indication of the presence of *M. paratuberculosis* in the sample. Techniques for detecting *M. paratuberculosis*-specific polypeptides include enzyme linked immunosorbent assays (ELISAs), Western blots, immunoprecipitations and immunofluorescence. An antibody of the invention can be polyclonal or monoclonal, and usually is detectably labeled. An antibody having specific binding affinity for a *M. paratuberculosis*-specific polypeptide can be generated using methods described herein. The antibody can be attached to a solid support such as a microtiter plate using methods known in the art (see, for example, Leahy et al., 1992, *BioTechniques*, 13:738–743). In the presence of *M. paratuberculosis*, an antibody-polypeptide complex is formed.

In addition, *M. paratuberculosis*-specific polypeptides of the invention can be used as an agent to detect the presence or absence of anti-*M. paratuberculosis*-specific antibodies in a biological sample. The presence of anti-*M. paratuberculosis*-specific antibodies in a sample indicates that the animal from which the sample was obtained mounted an immune response toward *M. paratuberculosis*. Given the etiology of *M. paratuberculosis* in its host animals, an animal that has detectable levels of anti-*M. paratuberculosis*-specific antibodies is likely infected with *M. paratuberculosis*. Alternatively, an animal that is positive for anti-*M. paratuberculosis*-specific antibodies may have resisted infection following a previous exposure to *M. paratuberculosis*, or may possess maternally-transmitted anti-*M. paratuberculosis*-specific antibodies. Techniques for detecting anti-*M. paratuberculosis*-specific antibodies in a biological sample include ELISAs, Western blots, immunoprecipitations, and immunofluorescence. A *M. paratuberculosis*-specific polypeptide can be attached to a solid support such as a microtiter plate by known methods (Leahy et al., supra). In the presence of *M. paratuberculosis*, a polypeptide-antibody complex is formed.

Detection of an amplification product, a hybridization complex, an antibody-polypeptide complex, or a polypeptide-antibody complex is usually accomplished by detectably labeling the respective agent. The term "labeled" with regard to an agent (e.g., an oligonucleotide, a polypeptide, or an antibody) is intended to encompass direct labeling of the agent by coupling (i.e., physically linking) a detectable substance to the agent, as well as indirect labeling of the agent by reactivity with another reagent that is directly labeled with a detectable substance. Detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H. Examples of indirect labeling include using a fluorescently labeled secondary antibody to detect an appropriate agent (e.g., a primary antibody), or end-labeling an agent with biotin such that it can be detected with fluorescently labeled streptavidin.

In another embodiment, the methods further involve obtaining a biological sample from an animal known to be infected with *M. paratuberculosis* (positive control) and a non-infected (negative control) animal, contacting the control samples with an agent capable of detecting *M. paratuberculosis*-specific nucleic acids or polypeptides, or anti-*M. paratuberculosis*-specific antibodies, such that the presence or absence of *M. paratuberculosis*-specific nucleic acids or polypeptides, or anti-*M. paratuberculosis*-specific antibodies in the samples is determined. The presence or absence of *M. paratuberculosis*-specific nucleic acids or polypeptides, or anti-*M. paratuberculosis*-specific antibodies in the control samples should correlate with the presence and absence of *M. paratuberculosis* in the positive and negative control samples, respectively.

Methods of Preventing a *M. paratuberculosis* Infection

In one aspect, the invention provides methods for preventing a disease or condition associated with infection by *M. paratuberculosis* (e.g., Johne's disease) in an animal by administering a compound to the animal that immunizes the animal against *M. paratuberculosis* infection. Animals at risk for *M. paratuberculosis* infection can be administered the compound prior to the manifestation of symptoms that are characteristic of a *M. paratuberculosis* infection, such that a *M. paratuberculosis* infection is prevented or delayed in its progression.

In one embodiment, a compound that immunizes an animal can be a *M. paratuberculosis*-specific polypeptide. The sequences of *M. paratuberculosis*-specific polypeptides are disclosed herein (e.g., SEQ ID NOs:24–45) and can be produced using methods described herein. An *M. paratuberculosis*-specific polypeptide can be a fusion polypeptide, for example a *M. paratuberculosis*-specific polypeptide-immunoglobulin fusion polypeptide in which all or part of a *M. paratuberculosis*-specific polypeptide is fused to sequences derived from a member of the immunoglobulin family. An *M. paratuberculosis*-specific polypeptide or fusion polypeptide of the invention can be used as an immunogen to elicit anti-*M. paratuberculosis*-specific antibodies in an animal, thereby immunizing the animal.

In another embodiment, a compound that immunizes an animal can be a *M. paratuberculosis*-specific nucleic acid molecule. A *M. paratuberculosis*-specific nucleic acid molecule used to immunize an animal can include one of the *M. paratuberculosis*-specific nucleic acid molecules having the sequence shown in SEQ ID NOs:1–23. *M. paratuberculosis*-specific nucleic acid coding sequences (e.g., full-length or otherwise) can be introduced into an appropriate expression vector such that a *M. paratuberculosis*-specific polypeptide or fusion polypeptide is produced in the animal upon appropriate expression of the expression vector. Expression of the *M. paratuberculosis*-specific nucleic acid molecule and production of a *M. paratuberculosis*-specific polypeptide in an animal thereby elicits an immune response in the animal and thereby immunizes the animal.

Compounds that can be used in immunogenic compositions of the invention (e.g., *M. paratuberculosis*-specific nucleic acid molecules or *M. paratuberculosis*-specific polypeptides) can be incorporated into pharmaceutical compositions suitable for administration. Such compositions typically comprise the nucleic acid molecule or polypeptide, and a pharmaceutically acceptable carrier. As used herein, "pharmaceutically acceptable carrier" is intended to include any and all solvents, dispersion media, coatings, antibacterial and anti-fungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., ingestion or inhalation), transdermal (topical), transmucosal, and rectal administration. Solutions or suspensions used for parenteral, intradermnal, or subcutaneous application can include the following components: a sterile diluent such as water for injection, saline solution (e.g., phosphate buffered saline (PBS)), fixed oils, a polyol (for example, glycerol, propylene glycol, and liquid polyetheylene glycol, and the like), glycerine, or other synthetic solvents; antibacterial and antifungal agents such as parabens, chlorobutanol, phenol, ascorbic acid, thimerosal, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol or sorbitol, and sodium chloride in the composition. Prolonged administration of the injectable compositions can be brought about by including an agent that delays absorption. Such agents include, for example, aluminum monostearate and gelatin. The parenteral preparation can be enclosed in ampoules, disposable syringes or multiple dose vials made of glass or plastic.

Oral compositions generally include an inert diluent or an edible carrier. Oral compositions can be liquid, or can be enclosed in gelatin capsules or compressed into tablets. Pharmaceutically compatible binding agents, and/or adjuvant materials can be included as part of an oral composition. Tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Transmucosal administration can be accomplished through the use of nasal sprays or suppositories. For transdermal administration, the active compounds are formulated into ointments, salves, gels, or creams as generally known in the art.

It is especially advantageous to formulate oral or parenteral compositions in dosage unit form for ease of administration and uniformity of dosage. Dosage unit form as used herein refers to physically discrete units suited as unitary dosages for an animal to be treated; each unit containing a predetermined quantity of active compound calculated to produce the desired therapeutic effect in association with the required pharmaceutical carrier. The dosage unit forms of the invention are dependent upon the amount of a compound necessary to immunize the animal. The amount of a compound necessary to immunize an animal can be formulated in a single dose, or can be formulated in multiple dosage units. Immunization of an animal may require a one-time dose, or may require repeated doses.

For polypeptide vaccines, the dose typically is from about 0.1 mg/kg to about 100 mg/kg of body weight (generally, about 0.5 mg/kg to about 5 mg/kg). Modifications such as lipidation (Cruikshank et al., 1997, *J. Acquired Immune Deficiency Syndromes and Human Retrovirology,* 14:193) can be used to stabilize polypeptides and to enhance uptake and tissue penetration. For nucleic acid vaccines, the dose administered will depend on the level of expression of the expression vector. Preferably, the amount of vector that produces an amount of a *M. paratuberculosis*-specific polypeptide from about 0.1 mg/kg to about 100 mg/kg of body weight is administered to an animal.

Articles of Manufacture of the Invention

The invention encompasses articles of manufacture (e.g., kits) for detecting the presence of *M. paratuberculosis*-specific nucleic acids or polypeptides, or anti-*M. paratuberculosis*-specific antibodies in a biological sample (a test sample). Such kits can be used to determine if an animal has been exposed to, or is infected with, *M. paratuberculosis*. For example, a kit of the invention can include an agent capable of detecting *M. paratuberculosis*-specific nucleic acids or polypeptides, or anti-*M. paratuberculosis*-specific antibodies in a biological sample (e.g., a *M. paratuberculosis*-specific oligonucleotide, an anti-*M. paratuberculosis*-specific antibody, or a *M. paratuberculosis*-specific polypeptide, respectively).

For antibody-based kits to detect *M. paratuberculosis*-specific polypeptides, the kit can include, for example, a first antibody (e.g., attached to a solid support) that has specific binding affinity for a *M. paratuberculosis*-specific polypeptide and, optionally, a second antibody which binds to *M. paratuberculosis*-specific polypeptides or to the first antibody and is detectably labeled. For oligonucleotide-based kits to detect *M. paratuberculosis*-specific nucleic acids, the kit may comprise, for example, one or more oligonucleotides. For example, a kit of the invention can include a detectably labeled oligonucleotide probe that hybridizes to a *M. paratuberculosis*-specific nucleic acid molecule or a pair of oligonucleotide primers for amplifying a *M. paratuberculosis*-specific nucleic acid molecule. Such oligonucleotides provided in a kit of the invention can be detectably labeled or, alternatively, the components necessary for detectably labeling an oligonucleotide can be provided in the kit. Polypeptide-based kits for detecting anti-*M. paratuberculosis*-specific antibodies in a biological sample can contain a *M. paratuberculosis*-specific polypeptide as disclosed herein (e.g., attached to a solid support) and, optionally, an antibody which binds to *M. paratuberculosis*-specific polypeptides or to an anti-*M. paratuberculosis*-specific antibody and is detectably labeled.

Kits can include additional reagents (e.g., buffers, cofactors, or enzymes) as well as reagents for detecting the agent (e.g., labels or other detection molecules), as well as instructions for using such agents and reagents to detect the presence or absence of *M. paratuberculosis*-specific nucleic acids or polypeptides, or anti-*M. paratuberculosis*-specific antibodies. The kit can also contain a control sample or a series of control samples that can be assayed and compared to the biological sample. Each component of the kit is usually enclosed within an individual container and all of the various containers are within a single package.

The invention also encompasses articles of manufacture (e.g., vaccines) for preventing *M. paratuberculosis* infection in an animal. Articles of manufacture of the invention can include pharmaceutical compositions containing either a *M. paratuberculosis*-specific nucleic acid molecule or a *M. paratuberculosis*-specific polypeptide. Such nucleic acid molecules or polypeptides are formulated for administration as described herein, and are packaged appropriately for the intended route of administration. Pharmaceutical compositions of the invention further can include instructions for administration.

The invention will be further described in the following examples, which do not limit the scope of the invention described in the claims.

EXAMPLES

Example 1

Mycobacterial Strains

Mycobacteria used in this study are listed in Table 2. All mycobacteria were cultured in Middlebrook 7H9 media with 0.05% Tween 80 and oleic acid albumin dextrose complex (Becton Dickinson Microbiology, Sparks, Md.). Cultures containing *M. paratuberculosis* isolates were supplemented with 2 mg/L ferric mycobactin J (Allied Monitor Inc., Fayette, Mo.). All growth flasks were incubated at 37° C. without shaking.

TABLE 2

Mycobacterial strains used

| Isolate[a] | Source[b] | Origin | Additional Information |
|---|---|---|---|
| *M. avium* subsp. *paratuberculosis* | | | |
| ATCC 19698 | ATCC | Bovine | Isolated from ileum in 1974; type strain |
| 1434 | NADC | Ovine | |
| 1045 | NADC | Bovine | Isolated from a Holstein lymph node in 1984 |
| 1112 | NADC | Bovine | Isolated from an Angus lymph node in 1984 |
| 1018 | NADC | Bovine | Isolated from a Holstein lymph node in 1983 |
| KAY | NADC | Bovine | Isolated from a Holstein ileum in 1993 |
| K-10 | NADC | Bovine | Isolated from a Wisconsin dairy herd in 1990 |
| 1010 | NADC | Bovine | |
| 1113 | NADC | Bovine | |
| *M. avium* subsp. *avium* | | | |
| 236 | NADC | Bovine | |
| WP21 CP (Sep. 5, 2001) | NADC | Avian | Mycobactin J independent, isolated from a wood pigeon |
| 6004 CP (Oct. 16, 2001) | NADC | Chicken | ATCC 35719; TMC 801 |
| 1015 | UMN | Deer | |
| 1161 | UMN | Avian | |
| 1282 | UMN | Human | |
| 1285 | UMN | Human | |
| *M. phlei* | NADC | | |
| *M. smegmatis* | NADC | | |
| *M. intracellulare* | NADC | Porcine | TMC 1472, 35773; *M. avium-M. intracellulare-M. scrofulaceum* complex 6 |
| *M. fortuitum* | NADC | | |
| *M. bovis* | | | |
| BCG Pasteur (Aug. 11, 2001) | ATCC | | ATCC 35734; TMC 1011 |
| 95 1398 (1998–1999) | NADC | Deer | Isolated from a Colorado feedlot |
| *M. tuberculosis* TB 14323 | | Human | |

[a]Dates of isolation (month/day/year) are in parentheses;
[b]ATCC, American Type Culture Collection; NADC, National Animal Disease Center: UMN, University of Minnesota

Example 2

Annotation of *M. paratuberculosis* Contigs Greater than 10 kb

The sequencing and assembly strategies used herein for *M. paratuberculosis* were as described for *Pasteurella multocida* (see May et al., 2001, *Proc. Natl. Acad. Sci. USA*, 98:3460–5). For these studies, assembled *M. paratuberculosis* contig fragments greater than 10 kb were chosen. Predicted coding sequences were identified using ARTEMIS software and TB-parse, a program used to identify coding sequences in the *M. tuberculosis* genome (Cole et al., 1998, *Nature*, 393:537–44). The results were compared and verified manually in ARTEMIS. A putative ribosome-binding site (RBS) was also evaluated for each coding sequence. The presence of an AG-rich sequence approximately 30-bp upstream of the start codon was scored as a putative RBS sequence. Similarities were identified with BLASTP analysis by using GenBank and a local database constructed by the Computational Biology Center at the University of Minnesota (see, for example, cbc.umn.edu on the World Wide Web).

ARTEMIS and ACT are finded by the Wellcome Trust's Beowulf Genomics initiative and are available free on the internet at http://www.sanger.ac.uk/Software/. Sequence alignments between *M. paratuberculosis* and *M. avium* were compared and visualized with ACT software. *M. avium* is being sequenced by The Institute for Genomic Research (TIGR; http://www.tigr.org/cgi-bin/BlastSearch/blast.cgi?organism=*m__avium*). Sequence alignments to produce figures or schematic illustrations were performed with AssemblyLIGN™ software (Accelrys, Princeton, N.J.).

The nucleotide sequence of each *M. paratuberculosis* gene described in this study was deposited in the GenBank/EMBL Nucleotide Sequence Data Library under separate accession numbers AF445420 through AF445446.

Example 3

DNA Hybridizations

Genomic DNA was extracted from several species of mycobacteria using a modified method from that described by Whipple et al. (Whipple et al., 1987, *J. Clin. Microbial.*, 25:1511–15). Briefly, one liter of Middlebrook 7H9 cultured mycobacteria was incubated at 37° C. until an $OD_{540}$ of between 0.50 and 0.56 was reached. D-Cycloserine was added to the media at a final concentration of 0.5 mg/ml and incubated an additional 24 h. Mycobacteria were harvested by centrifuigation at 8,000 rpm for 15 min and the pellet was resuspended in 11 ml of Qiagen buffer B1 containing 1 mg/ml Qiagen RNase A. Lipase was added (450,000 Units, Sigma Catalog No L4384) to digest mycobacterial cell wall lipids. Following incubation for 2 h at 37° C., 20 mg of lysozyme was added and incubation proceeded for an additional 3 h at 37° C. 500 µl of Qiagen proteinase K (20 mg/ml) was added and incubated for 1.5 h at 37° C. Qiagen buffer B2 (4 ml) was added and the slurry mixed and incubated 16 h at 50° C. The remaining cellular debris was removed by centrifugation at 10,000 rpm for 20 min. The supernatant was poured over a pre-equilibrated Qiagen 500/G genomic tip. The loaded column was washed and processed according to the instructions of the manufacturer. PstI restricted DNA fragments were separated on a 1% agarose gel. DNA-containing gels were depurinated, denatured, and neutralized as described by Sambrook et al. (1989, *Molecular Cloning: A Laboratory Manual,* Second Ed., Cold Spring Harbor Laboratory Press, Cold Spring Harbor, N.Y.). DNA was transferred by capillary action to BrightStar-Plus membranes (Ambion, Austin, Tex.) and probes were labeled using [α-$^{32}$P]dCTP (ICN, Cost Mesa, Calif.) by random priming. Hybridization was performed in a AUTOBLOT hybridization oven (Bellco Biotechnology, Vineland, N.J.) at 45° C. for 16 h in ExpressHyb hybridization solution (Clontech, Palo Alto, Calif.). Probed blots were washed sequentially with solutions increasing in stringency as follows: 2 washes at room temp in 2×SSC, 0.1% SDS; 2 washes at room temp in 0.2×SSC, 0.1% SDS; and 2 washes at room temp in 0.16×SSC, 0.1% SDS. Detection was by autoradiography at room temp using BioMax MR film (Kodak, Rochester, N.Y.) with a Kodak intensifying screen for less than 16 hours.

Example 4

PCR Amplification

Oligonucleotide primers listed in Table 3 were designed using the *M. paratuberculosis*-specific nucleic acid sequences identified herein. PCR amplification of *M. paratuberculosis*-specific nucleic acid molecules was performed as follows. A PCR master mix was generated that contained (each in final concentration) 1× AmpliTaq Gold buffer (erkin-Elmer), 5% dimethylsufoxide (DMSO, Sigma), 20 mM each nucleotide (Roche Biochemicals), 10 ng genomic DNA, and 1 Unit of AmpliTaq Gold DNA polymerase (Perkin-Elmer). Primers were added to individual PCR tubes containing 25 µl of master mix. The PCR reaction conditions were as follows: a 5 min denaturing step at 94° C., followed by 35 cycles of: 94° C. for 45 sec, 55° C. for 1 min, and 72° C. for 2 min. At the end of 35 cycles, there was a 7 min incubation at 72° C. and a hold at 4° C. High fidelity Pwo polymerase (Boehringer Ingelheim Pharmaceutical Inc., Ridgefield, Conn.) was used in amplifications to generate probes used in Southern hybridization experiments. All other amplifications used Taq DNA polymerase (Roche Molecular Biochemicals, Indianapolis, Ind.).

TABLE 3

PCR primers used

| Gene | Primer 1 | SEQ NO NO: | Primer 2 | SEQ ID NO: |
|---|---|---|---|---|
| 10 | CGGCGGATCAGCATCTAC | 46 | CACCTCATCGTGGCCAGGTT | 47 |
| 11 | ACCGAACACGAGTGGAGCA | 48 | CAGACTCTGACCGACGTCAT | 49 |
| 38 | GCATTTCGGCTCCCACGGTG | 50 | TACGTCGGTTCGGCGCGCAT | 51 |
| 56 | ATGAACACTTCTTCCTCTCTA | 52 | CATATCGCGGTGATCCTGAC | 53 |
| 57 | ATGGCCACCAACGACGACCA | 54 | CGCGGCCGTCGGGCCGGCTG | 55 |
| 135 | GCAGGCGTTTGCGTTCTTG | 56 | CGAGGTCCGAAATAGCGTAG | 57 |
| 159 | ATGCGTTTCGCCCTCCCGAC | 58 | TCACGCCTTGATTTCGTCCT | 59 |
| 217 | TGGCCGAACGCGGACTGTTC | 60 | TAGGAATCCGCGTCGACGAT | 61 |
| 218 | CAAGGTTCGTGACGGTATCG | 62 | TGACCCCAGCAGGTATGGC | 63 |
| 219 | CATCTACTGAGCGCCGTTTG | 64 | CACGCCGCCACCCCGTCCCG | 65 |
| 228 | GCAAGGTGGGCTTTGAAG | 66 | TGCGTGGGAGGATAAGGC | 67 |
| 240 | TTGGCACTGGCGTTTATG | 68 | ACATCGGGAACACAGGTCTC | 69 |
| 241 | ATCCTCCGGTTTGGCGGGAA | 70 | ACAGAGGTCGATCGGGTCG | 71 |
| 250 | CAGTCGGCCGGCGAAACGCC | 72 | CGCGGCGAAATCGAACGC | 73 |
| 251 | CACGTGCTGTCCCCATCGGC | 74 | CTACGTCTTCGTGACCAAAG | 75 |
| 252 | TGACCACCGACAACCCCACG | 76 | CATGAGGGCTGTCCCTCTCC | 77 |
| 253 | TTGACCGCGTTGACGGCGTT | 78 | CAGCGGTCCGCGCTCTTCGC | 79 |
| 254 | TGGGCAGCCCGGTGTCCCG | 80 | CACGCGCTCCTTTCAGCCTT | 81 |

TABLE 3-continued

| | PCR primers used | | | |
|---|---|---|---|---|
| Gene | Primer 1 | SEQ NO NO: | Primer 2 | SEQ ID NO: |
| 255 | CAGTCACCCCGCGGCCGGTA | 82 | TCTACTGACCCGCAGATCGAA | 83 |
| 256 | TGGCCGTCAAGGACCAGAAC | 84 | CATGACCCTGCCGGCGTCCC | 85 |
| 257 | TGGCATTGGATCGCGTCGGA | 86 | TCAAACCCGGCGAGTTCTTC | 87 |

[a]Primers are shown in the 5' to 3' directions

Primers used to amplify the #7 sequence for a probe in Southern hybridizations were 5'-ATC AGG CTG ACG GGA TTG CCC-3' (SEQ ID NO:88) and 5'-TCA ACG AGT GCA CGG GAA CC-3' (SEQ ID NO:89).

Example 5

Twenty-seven M. paratuberculosis Predicted Coding Sequences are not Present in M. avium Sequencing the complete genome of M. paratuberculosis K-10, a field isolate recovered from a cow with clinical Johne's disease, is currently underway. See, for example, cbc.umn.edu/ResearchProjects/AGAC/Mptb/Mptbhome-.html on the World Wide Web. The genome size is estimated to be >5 Mb based on assembled sequence data, and by July, 2001, 2.65 Mb were contained in contig fragments greater than 10 kb. Those contigs that are above 10 kb were annotated using ARTEMIS and represent 48% of the total genome. The average size of the annotated contigs is 25 kb with one contig over 70 kb. Each gene within the annotated contig set was also checked manually and confirmed by TB-parse. These contigs were aligned with M. avium sequence data generated at TIGR. TIGR has 612 contigs that total 5,867,714 bp in the Jul. 8, 2001 data set.

M. avium and M. paratuberculosis display a high degree of similarity at the nucleotide level as well as local gene order conservation. An analysis of an 11-kb region surrounding the origin of replication for each of these genomes shows 98% sequence identity at the nucleotide level. The sequence similarity between orthologs in M. paratuberculosis and M. avium was greater than between M. paratuberculosis and other mycobacterial species. A more global comparison shows that these strong nucleotide identities are present throughout both genomes. Despite this strong genetic similarity, a total of 27 genes from the annotated M. paratuberculosis contigs were identified that did not align with the unfinished M. avium genome by computerized alignments. Of these, three contained weak similarity to proteins in other mycobacterial species or proteins in GenBank. This left 24 genes that have no significant similarity to any known proteins. Since only about half of the M. paratuberculosis genome was used in these analyses, a complete genome analysis may reveal an estimated 50 unique M. paratuberculosis genes.

Some M. paratuberculosis sequences that did not align with M. avium sequences, either in silico or experimentally, contain similarity to other mycobacterial species. One such sequence, designated #7, was tested by PCR and Southern hybridization with two M. avium isolates and two M. paratuberculosis strains. An amplified PCR fragment was produced only with M. paratuberculosis genomic DNA as template. Likewise, DNA hybridization on Southern blots detected only M. paratuberculosis sequences, not M. avium. However, BLASTP analysis of the #7 sequence revealed strong similarity to hypothetical proteins in the M. tuberculosis genome.

Example 6

PCR Analysis

PCR amplification was performed on several mycobacterial species, strains and isolates to experimentally determine the specificity for 26 of the 27 sequences (Table 4). Gene 128 was not included in these analyses because it had the lowest expect value (highest similarity to a sequence in GenBank) of the 27 sequences by BLASTP analysis. These data show that primers designed from all 26 M. paratuberculosis-specific genes from isolate K-10 could produce an amplified product in all 10 M. paratuberculosis strains or isolates tested. In addition, despite an absence of any homologous sequences in public databases, PCR products of the correct size were obtained for five genes using template from other mycobacterial species. Following this analysis a core group of 21 genes remained that are present only in M. paratuberculosis (Table 4).

TABLE 4

PCR analysis of M. paratuberculosis predicted coding sequences

| Strain | Gene Number | | | | | | | | | | | | | | |
|---|---|---|---|---|---|---|---|---|---|---|---|---|---|---|---|
| | 56 | 57 | 159 | 217 | 218 | 228 | 240 | 250 | 251 | 252 | 253 | 254 | 255 | 256 | 257 |
| M. paratuberculosis | | | | | | | | | | | | | | | |
| ATCC19698 | + | + | + | + | + | + | + | + | + | + | + | + | + | + | + |
| 1434 | + | + | + | + | + | + | + | + | + | + | + | + | + | + | |
| 1045 | + | + | + | + | + | + | + | + | + | + | + | + | + | + | |
| 1112 | + | + | + | + | + | + | + | + | + | + | + | + | + | + | |
| 1018 | + | + | + | + | + | + | + | + | + | + | + | + | + | + | |
| Kay | + | + | + | + | + | + | + | + | + | + | + | + | + | + | |

TABLE 4-continued

PCR analysis of M. paratuberculosis predicted coding sequences

| K-10 | + | + | + | + | + | + | + | + | + | + | + | + | + | + | + |
| 1010 | + | + | + | + | + | + | + | + | + | + | + | + | + | + | + |
| 1113 | + | + | + | + | + | + | + | + | + | + | + | + | + | + | + |
| M avium | | | | | | | | | | | | | | | |
| #236 | − | − | − | − | − | − | − | − | − | − | − | − | − | − | − |
| WP21 | − | − | − | − | − | − | − | − | − | − | − | − | − | − | − |
| TMC801 | − | − | − | − | − | − | − | − | − | − | − | − | − | − | − |
| 1015 | − | − | − | − | − | − | − | − | − | − | − | − | − | − | − |
| 1161 | − | − | − | − | − | − | − | − | − | − | − | − | − | − | − |
| 1282 | − | − | − | − | − | − | − | − | − | − | − | − | − | − | − |
| 1285 | − | − | − | − | − | − | − | − | − | − | − | − | − | − | − |
| M. phlei | − | − | − | − | − | − | − | − | − | − | − | − | − | − | − |
| M. smegmatis | − | − | − | − | − | − | − | − | − | − | − | − | − | − | − |
| M. intracellulare | − | − | − | − | − | − | − | − | − | − | − | − | − | − | − |
| M. fortuitum | − | − | − | − | − | − | − | − | − | − | − | − | − | − | − |
| M. bovis BCG | − | − | − | − | − | − | − | − | − | − | − | − | − | − | − |
| M. bovis 95-1398 | − | − | − | − | − | − | − | − | − | − | − | − | − | − | − |
| M. tuberculosis | − | − | − | − | − | − | − | − | − | − | − | − | − | − | − |

| | Gene Number | | | | | | | | | |
|---|---|---|---|---|---|---|---|---|---|---|
| Strain | 10 | 11 | 38 | 48 | 49 | 50 | 93 | 134 | 135 | 219 | 241 |
| M. paratuberculosis | | | | | | | | | | | |
| ATCC19698 | + | + | + | + | + | + | + | + | + | + | + |
| 1434 | + | + | + | + | + | + | + | + | + | + | + |
| 1045 | + | + | + | + | + | + | + | + | + | + | + |
| 1112 | + | + | + | + | + | + | + | + | + | + | + |
| 1018 | + | + | + | + | + | + | + | + | + | + | + |
| Kay | + | + | + | + | + | + | + | + | + | + | + |
| K-10 | + | + | + | + | + | + | + | + | + | + | + |
| 1010 | + | + | + | + | + | + | + | + | + | + | + |
| 1113 | + | + | + | + | + | + | + | + | + | + | + |
| M. avium | | | | | | | | | | | |
| #236 | − | − | − | − | − | − | + | + | − | − | − |
| WP21 | − | − | − | + | + | + | + | + | − | − | − |
| TMC8O1 | − | − | − | + | + | + | + | + | − | − | − |
| 1015 | − | − | − | + | + | + | + | + | − | − | − |
| 1161 | − | − | − | + | + | + | + | + | − | − | − |
| 1282 | − | − | − | − | − | − | + | + | − | − | − |
| 1285 | − | − | − | − | − | − | + | + | − | − | − |
| M. phlei | − | − | − | − | − | − | − | + | − | − | − |
| M. smegmatis | − | − | − | − | − | − | − | − | − | − | − |
| M. intracellulare | − | − | − | + | + | + | + | − | − | − | − |
| M. fortuitum | − | − | − | − | − | − | − | − | − | − | − |
| M. bovis BCG | − | − | − | − | + | − | − | − | − | − | − |
| M. bovis 95-1398 | − | − | − | − | + | − | − | − | − | − | − |
| M. tuberculosis | − | − | − | + | − | − | − | − | − | − | − |

"+" indicates that an amplification product of the correct size was detected by ethidium bromide staining.
"−" indicates that no amplification product was detected by ethidium bromide staining.

Example 7

Sequence Analysis of an M. paratuberculosis-Specific Eight Gene Cluster

Eight genes were present on contig fragment 1614. These eight genes are arranged in tandem, span a total of 4.4 kb at the end of the 1614 contig (FIG. 1), and are present only in M. paratuberculosis (Table 4). 1408-bp upstream of gene 250 is an integrase gene that contains similarity to other mycobacteriophage integrases. This 4.4-kb segment (designated #481 (SEQ ID NO:23)) contains genes 250–257 and is located at the end of the 46-kb contig 1614. The sequences represented by #481 were found to align with the 94-kb contig 1398 present in a different contig assembly data set (FIG. 1). The #481 sequence aligned near the center of the 94-kb contig, essentially at position 35 to 45 kb. A trimmed portion of the 1398 contig is shown in the alignment in FIG. 1. The results of this analysis further extended the region of M. paratuberculosis-specific nucleic acid sequence to a 9.4-kb region, which does not align with M. avium sequence in silico.

A TBLASTX analysis was performed on the 9.4-kb sequence (designated contig 1398-trimmed in FIG. 1). The results of these analyses revealed that, while no sequences aligned with M. avium, the ends of contig 1398-trimmed align with sequences in M. tuberculosis. This leaves a core sequence of eight ORFs within the #481 sequence that are present only in M. paratuberculosis. This core sequence is flanked by 1408 bp of non-coding sequence downstream and 1092-bp of non-coding sequence upstream (FIG. 1). Therefore, this novel core sequence is well separated from other predicted open reading frames.

Example 8

Southern Hybridization Analysis Shows that the #481 Sequence is Specific to *M. paratuberculosis*

To confirm experimentally that #481 is present only in *M. paratuberculosis*, three arbitrarily chosen genes of the #481 sequence (251, 253, and 255) were radiolabeled and used as probes in DNA hybridization with several mycobacterial species including *M. fortuitum, M. bovis, M. intracellulare, M. avium,* and *M. paratuberculosis*. Following Southern blotting, only a *M. paratuberculosis* fragment greater than 9.5 kb was detected by each of the three probes.

Example 9

Characteristics of *M. paratuberculosis*-specific Polypeptides

The characteristics of *M. paratuberculosis*-specific polypeptides shown in Table 5 were obtained using MacVector sequence analysis software (Oxford Molecular).

TABLE 5

Characteristics of *M. paratuberculosis*-specific polypeptides

| Gene | pI | MW (Da) |
| --- | --- | --- |
| 10 | 5.29 | 36,380 |
| 11 | 5.12 | 21,826 |
| 38 | 9.51 | 18,730 |
| 56 | 9.32 | 21,116 |
| 57 | 3.90 | 10,417 |
| 128 | 9.96 | 20,772 |
| 135 | 11.58 | 17,018 |
| 159 | 11.47 | 20,655 |
| 217 | 10.49 | 11,567 |
| 218 | 11.05 | 91,530 |
| 219 | 12.05 | 10,004 |
| 228 | 12.30 | 40,817 |
| 240 | 9.14 | 24,949 |
| 241 | 9.17 | 13,509 |
| 250 | 4.40 | 21,434 |
| 251 | 5.54 | 19,500 |
| 252 | 3.87 | 9,687 |
| 253 | 11.50 | 7,881 |
| 254 | 8.38 | 16,262 |
| 255 | 7.36 | 25,851 |
| 256 | 7.17 | 15,120 |
| 257 | 5.48 | 9,358 |

Example 10

Expression of *M. paratuberculosis* Genes in *E. coli*

To confirm coding predictions of novel *M. paratuberculosis* genes and assess their immunogenicity, coding sequences were amplified from the genome by PCR and cloned into the pMAL-c2 *E. coli* expression plasmid. These proteins were expressed as a fusion with *E. coli* maltose binding protein (MBP) to enable affinity purification on an amylase resin column. An immunoblot was probed with a monoclonal antibody that binds MBP, which identified each fusion protein. A duplicate immunoblot was probed with polyclonal sera from a rabbit immunized with a heat-killed preparation of *M. paratuberculosis*. Only the fusion protein containing the *M. paratuberculosis* specific polypeptide produced from gene 253 was detected by the rabbit sera, indicating that the polypeptide encoded by gene 253 was produced by *M. paratuberculosis*. The MBP protein was not detected by the polyclonal sera.

Example 11

The psp-1 Gene Product is Recognized by Sera From Cattle With Johne's Disease

The polypeptide produced from gene 253 was termed psp-1 (paratuberculosis-specific protein). To determine if psp-1 is recognized during infection of cattle, the purified MBP/psp-1 fusion was evaluated further by immunoblot with sera from cattle with overt signs of Johne's disease. Sera from all three Johne's cows examined recognized the MBP/psp-1 fusion protein but did not recognize MBP alone. Another *M. paratuberculosis*-MBP fusion protein using gene 251 was also evaluated in this experiment, but the fusion protein produced therefrom was only weakly detected.

Immunoblot analysis of psp-1 was further expanded to include additional sera from Johne's cattles as well as control cattle housed at NADC and a local Iowa diary herd. The polypeptide designated psp-1 was not detected by sera from 7 control cows, but was detected by 14 of 16 Johne's cows tested.

Example 12

Expression of *M. paratuberculosis* Coding Sequences

Coding sequences within *M. paratuberculosis*-specific DNA fragments are cloned into *E. coli* expression vectors (e.g., containing a sequence encoding a 6×His tag). Heterologously expressed mycobacterial proteins are affinity purified from *E. coli* lysates by a polyhistidine tag. These purified proteins are then evaluated serologically with a panel of sera from infected and control cows to determine if the protein is recognized by sera from infected animals.

Specifically, each open reading frame identified as unique to *M. paratuberculosis* is amplified from genomic DNA, cloned into the pCRT7 expression vector (Invitrogen), and transformed into *E. coli* DH5-α. Each of the constructs are verified by DNA sequence analysis. The level of expression of the gene of interest is evaluated by loading the recombinant *E. coli* lysates onto SDS-PAGE gels and staining them in Coomassie blue. Expressed proteins are purified from *E. coli* lysates using the vector-encoded polyhistidine tag that has affinity for metal ions. Column purification using TALON metal resin (Clontech) is used. The fusion alone is used as a negative control. Comparisons of the reactivity of a collection of cattle antisera with the fusion proteins are conducted using a slot-blotting device (BioRad). Lysates of recombinant *E. coli* are loaded onto preparative 12% (w/v) polyacrylamide gels and transferred to nitrocellulose. After blocking, these filters are placed into the slot-blot device. Individual cattle antisera, each diluted 1:200, is added to independent slots. The rest of the procedure is carried out using standard immunoblot protocols. Protein G-peroxidase diluted 1:25,000 or anti-bovine IgG-peroxidase diluted 1:20,000 are used for detection of bound antibody.

Example 13

Production of Monoclonal and Polyclonal Antibodies Against *M. paratuberculosis*-specific Polypeptides All expressed and purified *M. paratuberculosis*-specific polypeptides are used to immunize both BALB/c mice and New Zealand white rabbits. Standard immunization regimens are used in each instance. TiterMax or Freund's incomplete serve as the adjuvant. Splenic lymphocytes from the immunized mice are hybridized with myeloma cells for the production of monoclonal antibodies. ELISA is the method used to assay secreting hybridomas for reactivity to purified antigens. Hybridomas in positive wells are cloned and expanded using standard methods. Rabbit antisera is collected following boost injections of isolated polypeptide until a sufficient titer is obtained.

Example 14

ELISA Assays

Improvement in the specificity of the ELISA test for detection of animals with Johne's disease has always been a major goal. The only test commercially available in the US is a direct test that uses a protoplasmic antigen preparation (Dubash et al., 1995, *J. Vet. Diag. Invest.*, 7:347–51; Collins & Sockett, 1993, *J. Am. Vet. Med. Assoc.*, 203:1456–63). Efforts to amplify antigen/antibody reactions focus on the use of an indirect biotin/avidin system. The purified M. paratuberculosis-specific polypeptide to be evaluated is diluted in PBS and added to 96-well microtiter plates. Plates with bound polypeptide are blocked in PBS containing 1% gelatin and then washed three times with PBS containing 0.05% Tween. Test cattle sera is diluted 1:400 in PBS, added to individual wells, and processed as a standard ELISA. Mouse anti-bovine IgM or mouse anti-bovine IgG is the second antibody in these assays. Results show that the use of a biotinylated second antibody followed by streptavidin/ alkaline phosphatase and enzyme detection enhances test sensitivity 8 to 16-fold (based on antibody titers) as compared to the standard direct ELISA.

The method described herein using a *M. paratuberculosis*-specific polypeptide is compared to the commercially-available direct ELISA by determining antibody titers of sera from clinically affected animals. Sera selected for these evaluations will include samples from both clinical and subclinical animals at NADC and from a nearby diary herd (State Center, Iowa) shown to have Johne's disease. For all evaluations, it is necessary to include samples from known negative animals to assess specificity. In addition, because of potential cross-reactivity that may be encountered with other bacteria, especially other mycobacteria, sera from animals known to be naturally or experimentally infected with other mycobacterial, particularly *M. avium*, are included. These controls determine whether the ELISA test detects only *M. paratuberculosis*-infected cattle.

Example 15

Use of Antibodies Against *M. paratuberculosis*-specific Polypeptides in Immunohistochemical Diagnosis of Infected Bovine Tissues Histopathologic analysis of tissues from infected animals is a rapid method of detecting *M. paratuberculosis*. Biopsy tissue or tissue samples taken at necropsy are stained for acid-fastness to determine the presence of *M. paratuberculosis*. However, this method is non-specific and does not distinguish among mycobacterial species. Therefore, bovine tissues from *M. paratuberculosis*-, *M. bovis*-, *M. avium*-infected and uninfected animals are tested by histopathologic analysis using high-titer antibodies directed at *M. paratuberculosis*-specific polypeptides. Briefly, samples from the ileum and mesenteric lymph node of cows are fixed in buffered formalin, processed routinely, and embedded in paraffin wax. 6 µm cut sections are stained with hematoxylin and eosin or Ziehl-Neelsen by conventional methods. Replicate unstained sections will be prepared for immunohistochemistry. Sections that are immunostained are deparaffinized, rehydrated and blocked using routine methods (Stabel et al., 1996, *J. Vet. Diagn. Invest.*, 8:469–73). Blocked sections are incubated with *M. paratuberculosis*-specific antibodies developed in the above-described studies. Depending on the nature of the primary antibody, either goat anti-rabbit biotinylated antibody or goat anti-mouse biotinylated antibody is added followed by washing instreptavidin-alkaline phosphatase solution. The tissue is stained with chromogen, and Histomark Red. Results are visualized under a bright-field microscope. Staining intensities are quantitatively compared among the different infected and uninfected tissues.

Example 16

Detection of *M. paratuberculosis* by PCR Amplification

Detection of *M. paratuberculosis* using oligonucleotide primers complementary to *M. paratuberculosis*-specific genes 93, 135, 218, 228, 240, and 251 or oligonucleotide primers complementary to IS900 nucleic acid sequences was examined by PCR. IS900 primer sequences were as follows: 5'-AAT CAA CTC CAG CAG CGC GGC CTC G-3' (SEQ ID NO:108) and 5'-CCG CTA ATT GAG AGA TGC GAT TGG-3' (SEQ ID NO:109). Fourteen fecal samples were processed from cattle in various stages of shedding. The bacterial load being shed by each animal was determined by culture on 7H10 slants.

To detect *M. paratuberculosis* by amplification of nucleic acids from a biological sample, a PCR master mix was generated similar to that described in Example 4 with the addition to the master mix of 10 mM MgCl. The PCR reaction conditions for amplification of nucleic acids from a biological sample were as follows: a 10 min denaturing step at 94° C., followed by 50 cycles of: 94° C. for 59 sec, 60° C. for 30 sec, and 72° C. for 1 min. At the end of 50 cycles, there was a 10 min incubation at 72° C. followed by a hold at 4° C.

Results of the PCR assays are as follows. Seven cattle identified as shedding heavily were all positive for *M. paratuberculosis* nucleic acid using either IS900 or MP228 primers. Out of 5 cattle identified as medium shedders, primers directed toward IS900 detected *M. paratuberculosis* nucleic acid in 1 animal, while primers directed toward MP228 detected *M. paratuberculosis*-specific nucleic acid in 2 animals. Out of 2 cattle identified as low shedders, primers directed toward IS900 detected *M. paratuberculosis* nucleic acid in 1 animal, while MP228 primers didn't detect *M. paratuberculosis*-specific nucleic acid in any animal. In titrations of *M. paratuberculosis* genomic DNA (isolate K-10), IS900 nucleic acids were detectable in 1 fg of nucleic acid, while each of the *M. paratuberculosis*-specific nucleic acids were detectable in 10 fg of nucleic acid.

TABLE 6

Primers used in PCR amplifications

| Primer Name | Primer sequence | SEQ ID NO: | Gene |
|---|---|---|---|
| MP93F | 5'-TTGCTGCGGGAAGGTTGCC-3' | 90 | 93 |
| MP93B | 5'-CGAGAACGAGATGTGCGTCAG-3' | 91 | |
| MP135F | 5'-GCAGGCGTTTGCGTTCTTG-3' | 92 | 135 |
| MP135B | 5'-CGAGGTCCGAAATAGCGTAGG-3' | 93 | |
| MP218F | 5'-CCAAGGTTCGTGACGGTATCG-3' | 94 | 218 |
| MP218B | 5'-TGACCCCAGCAGGTATGGC-3' | 95 | |
| MP228F | 5'-GCAAGGTGGGCTTTGAAG-3' | 96 | 228 |
| MP228B | 5'-TGCGTGGGAGGATAAGGC-3' | 97 | |
| MP240F | 5'-TTGGCACTGGCGTTTATG-3' | 98 | 240 |
| MP240B | 5'-ACATCGGGAACACAGGTCTC-3' | 99 | |
| MP251F | 5'-ATGCCTACGGTTCGGTGC-3' | 100 | 251 |
| MLP251B | 5'-AAGACAGCGTCAGCCAGC-3' | 101 | |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method for detecting the presence or absence of *M. paratuberculosis* in a biological sample, comprising the steps of:
contacting said biological sample with an isolated nucleic acid under standard amplification conditions, wherein said nucleic acid comprises a nucleic acid molecule, wherein said nucleic acid molecule is at least 19 nucleotides in length, wherein said nucleic acid molecule has at least 75% sequence identity to an aligned portion of SEQ ID NO:23 or the complement of SEQ ID NO:23, wherein an amplification product is produced if *M. paratuberculosis* nucleic acid is present in said biological sample; and
detecting the presence or absence of said amplification product,
wherein the presence of said amplification product indicates the presence of *M. paratuberculosis* in the biological sample, and wherein the absence of said amplification product indicates the absence of *M. paratuberculosis* in the biological sample.

2. The method of claim 1, wherein said biological sample is obtained from a cow, a sheep, a goat, a rabbit, a deer, an antelope, or a bison.

3. The method of claim 1, wherein said biological sample is a fecal sample, a blood sample, or a milk sample.

4. The method of claim 1, wherein said nucleic acid comprises a nucleic acid sequence selected from the group consisting of SEQ ID NOs:72–87, 100, and 101.

5. The method of claim 1, wherein said detecting comprises electrophoretically separating said amplification product.

6. The method of claim 1, wherein said nucleic acid is labeled.

7. The method of claim 1, wherein said nucleic acid molecule has 75% sequence identity to SEQ ID NO:23.

8. The method of claim 1, wherein said nucleic acid molecule has 80% sequence identity to SEQ ID NO:23.

9. The method of claim 1, wherein said nucleic acid molecule has 85% sequence identity to SEQ ID NO:23.

10. The method of claim 1, wherein said nucleic acid molecule has 90% sequence identity to SEQ ID NO:23.

11. The method of claim 1, wherein said nucleic acid molecule has 95% sequence identity to SEQ ID NO:23.

12. The method of claim 1, wherein said nucleic acid molecule has 99% sequence identity to SEQ ID NO:23.

13. The method of claim 1, wherein said nucleic acid molecule comprises gene 250 (SEQ ID NO:15).

14. The method of claim 1, wherein said nucleic acid molecule comprises gene 251 (SEQ ID NO:16).

15. The method of claim 1, wherein said nucleic acid molecule comprises gene 252 (SEQ ID NO:17).

16. The method of claim 1, wherein said nucleic acid molecule comprises gene 253 (SEQ ID NO:18).

17. The method of claim 1, wherein said nucleic acid molecule comprises gene 254 (SEQ ID NO:19).

18. The method of claim 1, wherein said nucleic acid molecule comprises gene 255 (SEQ ID NO:20).

19. The method of claim 1, wherein said nucleic acid molecule comprises gene 256 (SEQ ID NO:21).

20. The method of claim 1, wherein said nucleic acid molecule comprises gene 257 (SEQ ID NO:22).

21. The method of claim 1, wherein any of said molecules that are 19 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *M. phlei*, *M. smegmatis*, *M. intracellulare*, *M. fortuitum*, *M. bovis*, and *M. tuberculosis*.

22. A method for detecting the presence or absence of *M. paratuberculosis* in a biological sample, comprising the steps of:
contacting said biological sample with an isolated nucleic acid under hybridization conditions, wherein said nucleic acid comprises a nucleic acid molecule, wherein said nucleic acid molecule is at least 19 nucleotides in length, wherein said nucleic acid molecule has at least 75% sequence identity to an aligned portion of SEQ ID NO:23 or the complement of SEQ ID NO:23, wherein a hybridization complex is produced if *M. paratuberculosis* nucleic acid is present in said biological sample; and
detecting the presence or absence of said hybridization complex,
wherein the presence of said hybridization complex indicates the presence of *M. paratuberculosis* in said biological sample, and wherein the absence of said hybridization complex indicates the absence of *M. paratuberculosis* in said biological sample.

23. The method of claim 22, wherein nucleic acids present in said biological sample are electrophoretically separated.

24. The method of claim 23, wherein said electrophoretically separated nucleic acids are attached to a solid support.

25. The method of claim 24, wherein said solid support is a nylon membrane or a nitrocellulose membrane.

26. The method of claim 22, wherein said nucleic acid is labeled.

27. The method of claim 22, wherein said biological sample is selected from the group consisting of a fecal sample, a milk sample, and a blood sample.

28. The method of claim 22, wherein said biological sample is obtained from a cow, a sheep, a goat, a rabbit, a deer, an antelope, or a bison.

29. The method of claim 22, wherein said nucleic acid molecule has 75% sequence identity to SEQ ID NO:23.

30. The method of claim 22, wherein said nucleic acid molecule has 80% sequence identity to SEQ ID NO:23.

31. The method of claim 22, wherein said nucleic acid molecule has 85% sequence identity to SEQ ID NO:23.

32. The method of claim 22, wherein said nucleic acid molecule has 90% sequence identity to SEQ ID NO:23.

33. The method of claim 22, wherein said nucleic acid molecule has 95% sequence identity to SEQ ID NO:23.

34. The method of claim 22, wherein said nucleic acid molecule has 99% sequence identity to SEQ ID NO:23.

35. The method of claim 22, wherein said nucleic acid molecule comprises gene 250 (SEQ ID NO:15).

36. The method of claim 22, wherein said nucleic acid molecule comprises gene 251 (SEQ ID NO:16).

37. The method of claim 22, wherein said nucleic acid molecule comprises gene 252 (SEQ ID NO:17).

38. The method of claim 22, wherein said nucleic acid molecule comprises gene 253 (SEQ ID NO:18).

39. The method of claim 22, wherein said nucleic acid molecule comprises gene 254 (SEQ ID NO:19).

40. The method of claim 22, wherein said nucleic acid molecule comprises gene 255 (SEQ ID NO:20).

41. The method of claim 22, wherein said nucleic acid molecule comprises gene 256 (SEQ ID NO:21).

42. The method of claim 22, wherein said nucleic acid molecule comprises gene 257 (SEQ ID NO:22).

43. The method of claim 22, wherein any of said molecules that are 19 to 30 nucleotides in length, in combination with an appropriate second nucleic acid molecule, under standard amplification conditions, generates an amplification product from *M. paratuberculosis* nucleic acid but does not generate an amplification product from nucleic acid of any of the organisms selected from the group consisting of *M. phlei, M. smegmatis, M. intracellulare, M. fortuitum, M. bovis,* and *M. tuberculosis*.

* * * * *

UNITED STATES PATENT AND TRADEMARK OFFICE
CERTIFICATE OF CORRECTION

PATENT NO. : 7,074,559 B2  Page 1 of 1
APPLICATION NO. : 10/137113
DATED : July 11, 2006
INVENTOR(S) : Vivek Kapur et al.

It is certified that error appears in the above-identified patent and that said Letters Patent is hereby corrected as shown below:

Title Page, (75) Inventors, Ling-Ling Li, please delete "Moundsview" and insert --Mounds View--therefor;

Title Page, (73) Assignees, please delete "Refents" and insert --Regents--therefor;

Title Page, (73) Assignees, please delete "Unites" and insert --United--therefor.

Signed and Sealed this

Fourteenth Day of November, 2006

JON W. DUDAS
*Director of the United States Patent and Trademark Office*

SEQUENCE LISTING

<160> NUMBER OF SEQ ID NOS: 109

<210> SEQ ID NO 1
<211> LENGTH: 969
<212> TYPE: DNA
<213> ORGANISM: Mycobacterium paratuberculosis

<400> SEQUENCE: 1

```
gtgcgcccgc acaccggcgg acggcggatc agcatctact ggacgtggag ctatccgtgg      60
gaatcgcagc gcgacattca gaccctggac aaccgcttct ccaccatgac cgaagtgcgc     120
agggcggcct ggccccgata cgaggggccc gactgggacg acgcccactt tctgcagggc     180
atcgccggca ccttggagct tttccaccgc tcgacgcttg cgttccagga gctggccggc     240
gaagcaaccg gtcagcaggt ggcggtgttc cagcgcgtcg accaggccgg ctaccggctg     300
gtgatcgacg agcggatatt ggccgacacc gacaccctga tggtgttcgg gctggaccat     360
ctcgccgggg aagacgaggc cgagcccggg gagatctcgg ccatccgtgc ctggctggaa     420
cgcgagggca cctgcctgct gctggccccg caccacgacg tcggcggcac cgacgacatg     480
gcccagcggc aggtcgaata cctgcaccac ggggatccgc tcgtgccgcg gcaacaacgg     540
tttttccgcct acacccgctc gctgatgaag gggctcgacg ttcccgtccg caacaggtgg     600
ggcctgcatc cggcccgggt ggccgcgacc ggtcagatgg caccgctgac ctgctttcgc     660
gacctggacg cgcccgggct gctggacgat gtcacgacgc tgaactttca cccgcatctg     720
ccgcactacg agctcaccgc cccggaaagc gacgggctac gggtgctggc cacccaacgc     780
```

-continued

```
gtcgacccgg cccggcccca tcccttracc gaggcgggca acagcgaatt caacgcgttg      840
atctggatgc cgccgcacgc cgaacgagcc ggtgacatcg tgctcgtcga ctcgaccaac      900
ttcacgacgc tgttcggcgg gtccgacagc ctcagaaact tctggcacaa cctggccacg      960
atgaggtga                                                              969
```

<210> SEQ ID NO 2
<211> LENGTH: 576
<212> TYPE: DNA
<213> ORGANISM: Mycobacterium paratuberculosis

<400> SEQUENCE: 2

```
atggtggcaa ccgaacacga gtggagcaaa cccgcggccc tggccattcc cagggagggc       60
tacttcgagc tcgaacgcgg tcgttacggg ccgctgtatc cccgcacccc ggcctgctac      120
ggcttttcca tcatcgccaa ggtcaaggag ggccgcgagg aagccgtccg cgcctacggc      180
aaacagatcg aagaggccat caaggccgat ccgcacgtgc ttgccgcgct gcggctgcac      240
tacctgcgct ggttgctctt cgacgtcgga tcgggactgc acttccagta ccagggcatc      300
ttcgacacgg acttcgacaa gtacaccgag gacgcggtgc agctgttcag tcagaccggg      360
atcaccaccg tcttcacgaa cctcgagggg tttcccgaag actggcggga gaacccggac      420
gccttcgtca gttcgtgcg tgagcaccag tgcccgagct ttctggagta cggggagtat      480
ccctacgtca ccgccgacga gatcaaaaag gcgtacggct caagccgcct cccagaccat      540
gctggatcag atgcaatgac gtcggtcaga gtctga                                576
```

<210> SEQ ID NO 3
<211> LENGTH: 522
<212> TYPE: DNA
<213> ORGANISM: Mycobacterium paratuberculosis

<400> SEQUENCE: 3

```
atggtggtaa gcatttcggc tcccacggtg ccgataccccc aggcgatgac gttcagcggt      60
ctgcggtcag acatcggaca gaagccgacg cgtgggcagc accgtcaacg ggacgccgcg      120
atcttcgaac tgccagttcg gcccatgaga gatgtaggtc atttcgactt cctcccggcg      180
cttcgcttcg gtgtccgacc accggatgtc gacgaccagg tcgctggcct cgtaggtcgc      240
gtgcagatcc gaccagtgcg gatcgacacc ggtggccatg acctcgaggg gactgacatc      300
gtgcgtcgac agcgtcgcca tccaactgcg gtcgcggacg gcggggagt tgcttgggat      360 gcgcacccgc accgcgtcgc gcgctcctgt cccgaggcgc tccacggatg ctccggtgta      420
ggcgaacggg cgcagggcgg gatgcaaatc gaggaccgaa gcaaggtcat ctgcgccgac      480
gccaaacccg aggctgcttt gatgcgcgcc gaaccgacgt ag                         522
```

<210> SEQ ID NO 4
<211> LENGTH: 582
<212> TYPE: DNA
<213> ORGANISM: Mycobacterium paratuberculosis

<400> SEQUENCE: 4

```
atgaacactt cttcctctct acctgtcgac accctggacg tcaccgcacc accggatgcc       60
actgaggttt acgctgggc agcgcaccca gacggtctgg ccgcccgtgc attcgaagca      120
gcggtgcgtg actgcgccgg ctaccgggtc cgggtgcgcg gtgcgcaacg ctccaacgtc      180
acctgccgcc gctgggtggc catcgaagcc gcacccggcg ccgacgagca agcgttggag      240
```

```
cccgaagcgg tgcggcagct ggcgccgcag atgagcgtca cgcctaccac gcgccggaca    300
gctgagatgc tcgacgacgc cgccttcgat gcgatcgtcg cggtgttcag tcaacgggcc    360
cgatgcgaga tgcaaacgct gtcgggaggc aagtgcccac gggctgcgcg ctggcgcatt    420
gatttgcacg ggtgcgaaca ggccattgtg tgcgggcagc acaagaaagc gtggctgcag    480
gaggccctag ccaacctctg cgcgggcatt caacctcgct gcgcccactg cggaagagtg    540
ttcaacagct ccaagacgc ggtcaggatc accgcgatat ga                       582

<210> SEQ ID NO 5
<211> LENGTH: 311
<212> TYPE: DNA
<213> ORGANISM: Mycobacterium paratuberculosis

<400> SEQUENCE: 5
atggccacca acgacgacca agacgacggg aagccaccca ttaccgcggc cgctggcggt     60
gatgagaccg cgatcggggc ggccgctgat gaaaccgagc tcgtcgcgcc gctcaccgtg    120
cccgcgtccg agttggcctg gtcccacgag gacagcgacg ctggtgatta ctcgtggggc    180
cgggctgcgg aacgcgccag catcatcgtg ctcgcctgtg cggcggtcgc tgtcgtgatc    240
ggtttgctga cctggctcgc cttgcaccta cacgaccagg ccaagccgac agccggcccg    300
acggccgcgc g                                                         311

<210> SEQ ID NO 6
<211> LENGTH: 576
<212> TYPE: DNA
<213> ORGANISM: Mycobacterium paratuberculosis

<400> SEQUENCE: 6
atgagcgcca gggatctcat caacatcggg gtcttcggcg ctctctacat cgccactgtg     60
ttcgcgatca acgtgttcgc tttcatcaat ccgctcgtca tgttggtcgc cctggcggtc    120
agcatgatcg ccggcggcgt gccgttcatg ttgttcctca cccgggtgcg acatgcgggc    180
atggtgacgg tgtttgcgat tatcacggcc ggactgctcg cactgaccgg gcaccccccg    240
atctgcttcg tgatcacagt tgcgtgcgcg ttggtggccg aagtcgtcct gtggctggga    300
cgctatcgct cccgcaccat gggtgtactg gcgtacgcaa tctacgcggc gtggtacatc    360
gggccgctgc tgcccatctt ctacgctcgc gatgaatatt tctccagtcc cggcatggca    420
cagatgggtc gcgctacct cgaagagatg gaacggttgt tgtcgccagc cgtgctaatc    480
gcattcgacc tgtccacggt ggtattcggg ctgatcggcg gactgctcgg agtaaggttg    540
ctgcgcaagc attttcagag ggccggccta gcttga                             576

<210> SEQ ID NO 7
<211> LENGTH: 474
<212> TYPE: DNA
<213> ORGANISM: Mycobacterium paratuberculosis

<400> SEQUENCE: 7
atggcgggga tgccggagga ggtcgctgcg cttctgcgcg gtttcccacg catcggcgcg     60
cgcgagcagg cgtttgcgtt cttgaccgtt gacactggcg ggtttccaca tgcggcgttg    120
ctgtcgcgct gcgagctcga gcctgggcgg gaccccaaa cactgatggc cgccatagct    180
agccgacaga cccgcgccaa cttgcggcgt agcggcaccg cgggctgct cgcaatcaat    240 ggcactagtt gccaccacct caagctgcga gtggtcgcct cgctcgtcgg tcgcggaata    300
ctcggatgtg tgtttgccgt gaccgaacat aagcgcgatg acatgggaat acccttgcag    360
```

-continued

```
cctacgctat tcggacctc ggccgagatc tcggtgcttg aggactggcc gcgtagtcgg    420
gccatgttcg accgtctcgc agcgctgcgc agcgcagcgc gggaggtcct atga         474
```

<210> SEQ ID NO 8
<211> LENGTH: 558
<212> TYPE: DNA
<213> ORGANISM: Mycobacterium paratuberculosis
<400> SEQUENCE: 8

```
atgcgtttcg ccctcccgac gcgcatcctg cactggctga tggcgccgat ggtcatcggg    60
cagctgctca tcggggtggt catgatcacg tcgttgacct actatccgct gctgctggcc   120
atccaccggc cgttgggcgc cttgatcctg cgtttgcgg tggtgcgcct ggcgaaccgg    180
ttcacccacc ggctgccgcc cttccttgcc acgatgggcc ccgtcgaacg ccgcgtcgcg   240
acatggtcgg agtacctgct ctatgccctg ctgctagccc agcccttgat cgggtgggcg   300
atgctgtcgg cggcgcggtt cccggtcgtc ttggtgggac ccgtgcatct gcccggcatc   360
gcaccgcaca acgtcgacgt ctatgcgcg ctgcgccaag cccacaacgt cggcgccttc    420
ctgcttttcc tgaccttcac ggcccacgtc tgcgcggtcc tctttcatac gctcggcctg   480
cgcgaccggc tcctcgatcg catggcgctg tgcccacca gcccgtcgc ctcgcggcag     540 gacgaaatca aggcgtga                                                  558
```

<210> SEQ ID NO 9
<211> LENGTH: 321
<212> TYPE: DNA
<213> ORGANISM: Mycobacterium paratuberculosis
<400> SEQUENCE: 9

```
ctgcgcaggc tgatggccga acgcggactg ttcaacacga cagcgttgcg gccactgctg    60
gccgaacgcg gggtgcagct gtcggccagc caggtctacc ggctcgtgac cgagaaaccg   120
gaacggttga gcctgcccac cctggtggca ctggtggaca ttttgaggtg tgcgatggac   180
gagttgatcg agatcgtgcc cgccacagct gcctcggcga agaaggccgc gggcgcaccg   240 agcgcagca aaccggtcag gacgcgggaa cttggtggcc accgccccgt ccgggccaag    300
atcgtcgacg cggattccta g                                              321
```

<210> SEQ ID NO 10
<211> LENGTH: 2508
<212> TYPE: DNA
<213> ORGANISM: Mycobacterium paratuberculosis
<400> SEQUENCE: 10

```
atgcgcggaa accgcagcga gttcgtgacg gtgatcgtca ctgcagtggg cgcgatcgag    60
ccgcacctga gccacgacga tgtccgcacc gcgatcgagg ggatgggcct gtcggccgcg   120
cagttgcaga ggctgtctag aacgctgcgg cgcgacggta gcgtgctcac cgggcccggc   180
ggcagcgact gcgccgccga catcgagcag ctgatcctgt gtctgcgcca actcggcgcc   240
atgcgtgttc gagcgccgcg gtgtgcccag tgcggccgca acgattccga aacctactcg   300
cgcaagctca agaagcgcat ctgccagccc tgttcgatgc agggttggca gccggctgtc   360
ggtgaatgcc cgggctgcgg cgcggtggac aagttgatct accggccgcg gcacggcgat   420
ggcctgttgt gtcggaggtg caagcccgaa cccgacgtcg atcacgccgc caagttcgt    480 gacggtatcg cgcaactgcg gaccgggctt tcggccaccg agattgaccg ggtggcgtcg   540
```

-continued

```
gtgttcggca cggcggtcgc gcagcgcgag cttaactgga tcttgcagga cacccccgga    600
gtgtttcgcg gtgagatcgc ccaccgctcg gcggtctcgg tgcggctcgc cgaactactt    660
gtcgctgccg gtgccgacaa tgtgcgcctt ccgcagtgcc cgttgtgttt gcgcaccgtg    720
aagctcggca gccagattga cgggttgcgc tgctgccata cctgctgggg tcaccacttc    780
agccgcggca cctgcgctcg ttgcggttgc cagcgtcacc ttatcaatta tcacggtgcc    840
ggcgagcgcc tctgtcaccg ttgtttcgag catgatccgg tcaatcatga gccgtgtaca    900
cggtgcggtc gtgtggactt catcaaccac catgacggcc aagcgaagct ctgccggcgc    960
tgctacccgg cacccaccgc ggtctgcagc tcgtgcggac gtactcgccc atgcacccgc   1020
acccggacgg gaaagccgat ctgcggcacc tgctcggcca aacagcgccc accccaaccc   1080
tgttcggtat gcggcaacat ccgctccgtg cacacccgga ctgacgccgg tgagccggtg   1140
tgtaacccgt gcgcacgaag tcgggaaccg tgcgcgcggt gcggcaaaac gctgggggtc   1200
tcggcgcggc ttgccggggt cgggccgctg tgctcggcct gcctgcaacg tgaacccgcc   1260
tatttcaccg actgtgtgca atgcggcgcc catggacgga cgtaccaccg tgggctgtgc   1320
ccggcctgcg cctgtcccgg tgagctccgc gaattgttcg ccaagaacgg cgaattgagc   1380
ggcgccgcca gccgcatcgt cgaggcgttg ctgcaatgtg acgccatgcc ggtgctgcga   1440
tgggtcagac gcatgcgatc gaacagtgaa ctgcccgcgc agctcgccga actcggcgac   1500
accctcagcc accacgacct cgatgacctc ccggccagca aatccgtgga atggcttcgc   1560
aacatcctgg tgaccgccga gggtctgcca gaccgcgacc cctatctgca ccgcaccgag   1620
cagtacatcg ccgcccggct ggccaccatc agcaaccgcg acgatcgcgc ggccgtccgc   1680
gcattcaccg aatggaatca tttgcgtaaa ctccgggccc gcgccgacaa aggaccactc   1740
aaacgcaacc acggcctcgc cgcccagatc atggccgccg ccatcaccga cttcgtctcc   1800
gaactcaacg cgcacggact ggccttggcc tcatgccagc aggcgttcgt cgacgactgg   1860
ttggtgcgca accccactcg ccgccagatc caccaattcc tcgcctgggc ggtccaccgt   1920
ggctacgccc acgacgtcgc ggctcccgta ccgcaaaccc gccgcacccg ccacaccctg   1980
cccggcgacg acgaacgatg gcgcctgatc caatacctga tcgaacaccc cgacttggag   2040
acgcgcgatc gggtcgccgg gctgctcgtg ctgctctaca gccaacccgc cgcccgcctg   2100
gtcaccctca aggttgccga cgtcaccatc accgacgacg cggtccaact caccctcggc   2160
gccgtcccgc tcaccgtgcc cagccccgtc gaccgcctgc tcgccgatct cgtacagcag   2220
cgccgcggat acgccgcggt caccgtgggc accaatccat ggctgtttcc cggaggacgc   2280
tccggtgggc acctgtccgc caaccaagtg ggctgcggc tcaaacgaat tggcatctcc    2340
ccccggatcg cccgcaacac cgcgctgatc gacctcgccg gcgaactgcc cgctgtcgtg   2400
ctcgccaaac tcctcggctt cagcatcaaa cgcgccgtca cctggagcga agaagccggc   2460
aacactcgcc cccgctacgc cgccgaggtc gcccgccgca actcgtga                2508
```

<210> SEQ ID NO 11
<211> LENGTH: 264
<212> TYPE: DNA
<213> ORGANISM: Mycobacterium paratuberculosis

<400> SEQUENCE: 11

```
gtgtcaacat ctactgagcg ccgtttgcgc ttacaggtcg ccgttcacga gagctgggcg     60
cgcaccgaaa accgttccgc gcgaacgcat aacgcccgta aggcggcatg ggaccgcttc    120
gaaaagcagg tcgatcccga gggcaagcta ccccccgccc tgcgcgccaa gatggccgag    180
```

-continued aacgcccgcg cggcccactt caagaagatg gcgttgaagt ccgtcgagtc ccggcgccgt 240
cgccgggacg gggtggcggc gtga 264

<210> SEQ ID NO 12
<211> LENGTH: 1110
<212> TYPE: DNA
<213> ORGANISM: Mycobacterium paratuberculosis

<400> SEQUENCE: 12
gtgccatacg ccgaatcgcc caggacccgc accgggggtg tgttcaccct cgagcaggct 60
cagcccgacg acggcctcgt ggttgtccgc gccgctggcc ttggtcaacg cgcaatcggt 120
gatgattccg gtgtcgggct cgacggcaag gtgggctttg aagccgtcct ggcggcggtg 180
caccgtcttg tgagcgtgcc gcgtgtcggc atcgacggtg gagatcacgc gatccccact 240
gacctgctgc gcgatgcgcc agtgcccgtc ggtgccatca gagccctcga ccggttcaac 300
gtcttgaccg gcgatcaacg ccaacaacgc caccgcctca gcagcccgcg gcgcgagttc 360
ctggtcaggc agatagccca gcacccggtg agcatcaccg accaaaccat ccaccagccg 420
atcccgagcg gccttatcct cccacgcaat cgcgggtttc cccggatcgt cgtaatcatg 480
ggcgctgcag tgggcttcga tcaccgctgc agcgccaggg acttcgcggc gcactcgtcg 540
gatcgcggcg atcaactgcg tcacggtgtc ctgcgtggcc accgcatcgt cgagcaccgt 600
ggaatccaag gcccgccgtg tcttgcccgc caacaccccg gtctcggcca ccaccgtctt 660
gaccgcctcg aagatccggt tggccgatc cgaagccgcc aaccgacgcc gccaatacgt 720
caacgtcgtc gaatgaaacg cgcccgccgt gatcggcaac ccgcacgctg ctttccagcg 780
cagatcgaaa gtcaccgcat ccacggtctc gttatccgaa aaaccgtgca gggcctgcaa 840
ggtgatcacc gaggccatca cctcagccgg cacgctgggc cggccccgct gcgacgggaa 900
caagtccgcg aacatctcct cgggaaacaa ctggctgcgg tgcgccgcca ggaacgcaaa 960
catgctgtcg gccttcagaa gatgcccggc aaccgactcc gcatccaaca actcacgctg 1020
atcatcagag cgaccctgca cccaacaatc atccccaaaa ccccaggaca actcgtcccg 1080
ccacgcggaa ttaattcagc aggctcctag 1110

<210> SEQ ID NO 13
<211> LENGTH: 672
<212> TYPE: DNA
<213> ORGANISM: Mycobacterium paratuberculosis

<400> SEQUENCE: 13
ttggtcattg cgctagctgc cttgtggagc atccgtttgg cctggcacat cccgttcgag 60
cgagcagcag tgttggcact ggcgtttatg tgtgcccagt tggtcctggc gctcgggccg 120
gtggacgggt ggctgagccc attgctccac gacatgacgg gcgtgtggaa cctcgaagac 180
ctcatcggcc atctgctcta cgtgtacggc ttgttctcga tcatgtatct ggtcgctgac 240
cactgcgaca tgacgccggg tcagctcagg tggttcgttc ggaaccggtt ggaactgccg 300
tcggtcgtga tctgcgccgt catgatcgcg gtcttcgtcg caggcgacat cggcgagacc 360
tgtgttcccg atgttgtggc cacagaacac acgccctggc tccgcgtcta ctggttcgta 420
atgatcgcgg ctcttgcgta catcattgtc tctaccggtc gaatcctgtt gatcctgagg 480
cagcacccac gctcgaggca tgccgccacg gcctatctcg tagcgctcgg tatcactggc 540
gcgtgctgcg tggttttcat catcggaatc ccttggctgc aatggcttct cgtgcggtgc 600

```
gaggtagtcg gctatgcggt ggccgcctcg tactcctggc gtaacaaagt ggcttacttt      660
cgtggacgct ag                                                          672

<210> SEQ ID NO 14
<211> LENGTH: 372
<212> TYPE: DNA
<213> ORGANISM: Mycobacterium paratuberculosis

<400> SEQUENCE: 14
ttgcacgaaa tcctccggtt tggcgggaaa accgacgaat tgatcggttt tgcccgcgct       60
ttgtcggttc agactgctac cctgccgggc atgtcttcgc attcgcctgt gtcggccgcc      120
gccctggcca gccgattgcg gatgatcatg ggcgaccgca agctgtcccg tacccgtctt      180
tctcacgaga caggtatcag ccgcccgagc ctttctagca agctcgatgg caaggtcgag      240
ttcacctaca gtgagctact tacgatcgcc caggcggtcg atgttccgct ggacaagctg      300
ctcgccggag acgacgatga gcggcccttc cgcctgagtg acttgagacc tcgacccgat      360
cgacctctgt ga                                                          372

<210> SEQ ID NO 15
<211> LENGTH: 600
<212> TYPE: DNA
<213> ORGANISM: Mycobacterium paratuberculosis

<400> SEQUENCE: 15
atggttgcgg cgcaaggctc ctcgatgcta accgctgccg atttcgccgc gcaatgggcc       60
gatgttcccc cgtgggaacc gccggacgaa ccaccgcagc gaaacggcca acgacagcag      120
caggcaagcg ccgagccgac cacgtgggag gcgttcgatc tcggacccta cctgcgcggc      180
gaaatcgaac gcccacatcc cggtatcggc atatcacgct ccgacgggca gcggtcgctc      240
taccctggtc gcgagcacgc catagtcggt gaaaccgaaa gcgtaaaaac ctggttcgcg      300
ttgggctgcg ccgccgcaga actcaacgcc ggcaacgacg tcgtgtatat ccactacgaa      360
gaacccgacg cgacgagcac cgtcgagaag ctgtgcttgc ttggggtcga ccccgcggtg      420
atcaaggccc ggtttcggtt cgtcgctccc agccgccccg tccgtgagga gtggctgaac      480
gcactacttg acccttcacc gacgctggtc atccacgacg gcgtcaacga agcgatggcg      540
ctgcacggcg acgagatcaa ggccgtcgag ggcgccgcgg gcgtttcgcc ggccgactga      600

<210> SEQ ID NO 16
<211> LENGTH: 540
<212> TYPE: DNA
<213> ORGANISM: Mycobacterium paratuberculosis

<400> SEQUENCE: 16
atggtgcgcg acggcagccg ccgcgatgcc tacggttcgg tgcataaggg caacgcgctc       60 gacgggctc ggttcgtgct cgagaactcg gcgccgttcg gccggcggct gcgcggcgtc      120
tcctacgtct tcgtgaccaa agaccgcccc gggcatctac gggccaacgg gcgcgcaacg      180
aagtcgcccg gcaagacgtt catgggaact ctggtcgtcg atgactcgca ggcgttcggt      240
cctgacttca cgatgcggtt cttcgcgccc agggacgacg acgtgcctga gagcgatccg      300
aacgccgagc tggctgacgc tgtctttcgc gtcgttgctg cggctcccga ccacgctgtt      360
gggtcgatgc ggctgttgtt cgctgagtta cgcaacgtcg acatccagtt ccgtgacgac      420
gatgtgcgcg acgtcgtcga tgaccttgtg gtgtcaggcc gtctcgtaga gatatcaggc      480
aagcgtggcg ccaaggggtt cagggccgtt gtggaggacg ccgatgggga cagcacgtga      540
```

<210> SEQ ID NO 17
<211> LENGTH: 291
<212> TYPE: DNA
<213> ORGANISM: Mycobacterium paratuberculosis

<400> SEQUENCE: 17

| | | | | | |
|---|---|---|---|---|---|
| atgaccaccg | acaaccccac | gccctctgat | gaccaggcac | tggccgccct | ctacgccaca | 60 |
| gcactcggcg | tgctcctggc | cggcctcgtc | aacgacggac | gcctcacgac | cgagatcgag | 120 |
| cgcatcatcg | ccgccggcga | gaaagtcacc | gccggcgtcc | tcggcttcct | gaccgcagca | 180 |
| gccgccaacg | cctacgaata | cgagcacggc | agccgagaag | ccgccatcga | cgcagtcacc | 240 |
| gcagacctgg | ccaccgtgct | gctcgccgcc | ggagagggac | agccctcatg | a | 291 |

<210> SEQ ID NO 18
<211> LENGTH: 225
<212> TYPE: DNA
<213> ORGANISM: Mycobacterium paratuberculosis

<400> SEQUENCE: 18

| | | | | | |
|---|---|---|---|---|---|
| ttgaccgcgt | tgacggcgtt | gcgcgacgtc | ctggcggcgg | cgatcgatga | atgcgggtcg | 60 |
| aaacgtgatt | tggccgcgtt | gttgcggcag | ttcaccgctg | tcctggcgca | gatcgaggcg | 120 |
| gcgcgggtac | ggccaccgca | acgtcggatt | gccgatgaga | ttgcgcccg | gcggacagct | 180 |
| cggcaggccg | cggccgctgc | cgatgcgaag | agcgcggacc | gctga | | 225 |

<210> SEQ ID NO 19
<211> LENGTH: 441
<212> TYPE: DNA
<213> ORGANISM: Mycobacterium paratuberculosis

<400> SEQUENCE: 19

| | | | | | |
|---|---|---|---|---|---|
| atgagcgacg | agttacgcca | gcgctacaag | gtgattttcg | atgcagtccg | ggtgagcgaa | 60 |
| atcgagatca | ccccggatct | tgcgcggtgc | ctcgtgcact | ggctcggtga | ttacatccgg | 120 |
| ctcaagcagc | agcctgggca | gcccggtgtc | cggaggggt | tagttgcggc | gcagacggcg | 180 |
| cttgccgagg | cgtacgccgc | ggttactcac | tcgcctcgaa | gcgagcggga | tcgcccgatc | 240 |
| ggggctggat | tcgtattctc | agcccatgac | gcgtgggtgg | gcactgcgga | agccgctgag | 300 |
| atgctcggga | tcaaggcggg | cagcgtcggt | tggctttgcc | gggagagtca | tcttgagcac | 360 |
| cggaaagttg | gccggcagta | catgatttcg | accgcatcga | tcgaggacta | caaacgccgc | 420 |
| aaggctgaaa | ggagcgcgtg | a | | | | 441 |

<210> SEQ ID NO 20
<211> LENGTH: 726
<212> TYPE: DNA
<213> ORGANISM: Mycobacterium paratuberculosis

<400> SEQUENCE: 20

| | | | | | |
|---|---|---|---|---|---|
| atggtcaacg | tgccgcgtgc | ggaacttgcg | cggctggtgg | gggtttcgcc | ggacgtcgac | 60 |
| gatctaacgt | tgcagcaggc | catcgattcc | aagtcgcgc | agaatgaggc | cgaaaagcac | 120 |
| gctcacgcgg | tgtctgcggc | cgagcagcgg | gcccgcgcgg | atgaccggcg | aatcgtcatc | 180 |
| gctgcctaca | cgaaggccg | gattccgcag | agccgcatcg | acttctggtg | cgaagcaatg | 240 |
| caacgagacc | gcgccggcaa | cagggctatc | ctcgcggctt | tggcgccggg | actggccccg | 300 |
| cctgaaaagc | tcccctactga | cccgcagatc | gaacatgtcc | acgcgaaagt | ccttgctcgg | 360 |

```
atgggcatcc ggccgccggc atctgctccc acatcgcaga ctgtcgctgc gtcatcgcca    420
ccgccgtcac caggcgtcga tgatttgggc ataccgatcc gccgttgcc gccacctgtg     480 cgcatcgtgc gcatcgtgca cggcaaagat ccggccacgt ggtccaaaga agagcgcgat    540
aacgcgctgc tgtacgggct cggccccgg ttcgccgcag cggcggcggc gcgtgggatc     600
ccacgcccac ccggaggctc cgggtactac cagccgaccg gcatcgagcc ctacgagccc    660
gtcgacctgg gtggcggtca gatcgagtgg cgcgccaagc ccgactaccg gccgcgggt    720 gactga                                                              726
```

<210> SEQ ID NO 21
<211> LENGTH: 426
<212> TYPE: DNA
<213> ORGANISM: Mycobacterium paratuberculosis

<400> SEQUENCE: 21

```
atggcatacc gaatgagtcc ccgcgtcgag atgctggccg tcaaggacca gaacgggatc    60
atttggcatc actaccaaag acctgtcggg ggtgcccgca accttggtcc gatcattgcg    120
tggattggcc ctgactaccg ggatcgctgg ctacgcatgg gcctcatcga ggagatcccc    180
gacgacgccg cggccgccct gtcacagccc ccgcccagcg atgcagtcgc cggccccaat    240
accgatctcg tcgacgagtg catcgccgcg ctcgaccgtt tcgatgtgcc agccgatgcc    300
ggcgccccga ccgcgcggaa agccctgcgc gacaggggc aagcctgggg caacgagacc     360
atcgctgctg ctgtccgcgc gcgcaaggcc cgtgccgcgc cgtccgggac gccggcaggg    420
tcatga                                                              426
```

<210> SEQ ID NO 22
<211> LENGTH: 279
<212> TYPE: DNA
<213> ORGANISM: Mycobacterium paratuberculosis
<220> FEATURE:
<221> NAME/KEY: misc_feature
<222> LOCATION: 236
<223> OTHER INFORMATION: n = A,T,C or G

<400> SEQUENCE: 22

```
atgagcacca cgacggtgcc agtcggcacg acacccgctg cgatcacagg gattccgccg    60
gacgtcgact cggtgcaagt cctcaactcc agcgaggggc tcggtgatgc cgccggcgtc    120
gacatcgtcg tcaacaactc cggaggctgt tcgctggacc cgcagacggg gatccggctc    180 aaaccggcg agttcttcgt gttctcgcta cgccagccac atgggggccc ggccgnttgc    240
cgctgtacgc ggtcgcggcc ggccctggtg gtcagttga                          279
```

<210> SEQ ID NO 23
<211> LENGTH: 4415
<212> TYPE: DNA
<213> ORGANISM: Mycobacterium paratuberculosis
<220> FEATURE:
<221> NAME/KEY: misc_feature
<222> LOCATION: 44
<223> OTHER INFORMATION: n = A,T,C or G

<400> SEQUENCE: 23

```
tcaactgacc accagggccg gccgcgaccg cgtacagcgg caancggccg ggcccccatg    60
tggctggcgt agcgagaaca cgaagaactc gccgggtttg agccggatcc ccgtctgcgg    120
gtccagcgaa cagcctccgg agttgttgac gacgatgtcg acgccggcgg catcaccgag    180
cccctcgctg gagttgagga cttgcaccga gtcgacgtcc ggcggaatcc ctgtgatcgc    240
```

```
agcgggtgtc gtgccgactg gcaccgtcgt ggtgctcatg accctgccgg cgtcccggac      300
ggcgcggcac gggccttgcg cgcgcggaca gcagcagcga tggtctcgtt gccccaggct      360
tgccccctgt cgcgcagggc tttccgcgcg gtcgggggcgc cggcatcggc tggcacatcg     420
aaacggtcga gcgcggcgat gcactcgtcg acgagatcgg tattgggggcc ggcgactgca    480
tcgctgggcg gggggctgtga cagggcggcc gcggcgtcgt cggggatctc ctcgatgagg    540
cccatgcgta gccagcgatc ccggtagtca gggccaatcc acgcaatgat cggaccaagg     600
ttgcgggcac ccccgacagg tctttggtag tgatgccaaa tgatcccgtt ctggtccttg      660
acggccagca tctcgacgcg gggactcatt cggtatgcca tgtcagtcac cccgcggccg     720
gtagtcgggg ttggcgcgcc actcgatctg accgccaccc aggtcgacgg gctcgtaggg    780
ctcgatgccg gtcggctggt agtacccgga gcctccgggt gggcgtggga tcccacgcgc     840
cgccgccgct gcggcgaacc ggggggccgag cccgtacagc agcgcgttat cgcgctcttc   900
tttggaccac gtggccggat ctttgccgtg cacgatgcgc acgatgcgca caggtggcgg    960
caacggcgcg atcggtatgc ccaaatcatc gacgcctggt gacggcggtg gcgatgacgc     1020
agcgacagtc tgcgatgtgg gagcagatgc cggcggccgg atgcccatcc gagcaaggac    1080
tttcgcgtgg acatgttcga tctgcgggtc agtagggagc ttttcaggcg gggccagtcc    1140
cggcgccaaa gccgcgagga tagccctgtt gccggcgcg tctcgttgca ttgcttcgca     1200
ccagaagtcg atgcggctct gcggaatccg gccttcgttg taggcagcga tgacgattcg     1260
ccggtcatcc gcgcgggccc gctgctcggc cgcagacacc gcgtgagcgt gcttttcggc    1320
ctcattctgc gcgagcttgg aatcgatggc ctgctgcaac gttagatcgt cgacgtccgg    1380
cgaaaccccc accagccgcg caagttccgc acgcggcacg ttgaccatgc ccatcacgcg    1440
ctccttcag ccttgcggcg tttgtagtcc tcgatcgatg cggtcgaaat catgtactgc     1500
cggccaactt tccggtgctc aagatgactc tcccggcaaa gccaaccgac gctgcccgcc    1560
ttgatcccga gcatctcagc ggcttccgca gtgcccaccc acgcgtcatg ggctgagaat    1620
acgaatccag ccccgatcgg gcgatcccgc tcgcttcgag gcgagtgagt aaccgcggcg    1680
tacgcctcgg caagcgccgt ctgcgccgca actaacccct ccgggacacc gggctgccca    1740
ggctgctgct tgagccggat gtaatcaccg agccagtgca cgaggcaccg cgcaagatcc    1800
ggggtgatct cgatttcgct cacccggact gcatcgaaaa tcaccttgta gcgctggcgt    1860
aactcgtcgc tcatcagcgg tccgcgctct tcgcatcggc agcggccgcg gcctgccgag     1920
ctgtccgccg ggccgcaatc tcatcggcaa tccgacgttg cggtggccgt acccgcgccg    1980
cctcgatctg cgccaggaca gcggtgaact gccgcaacaa cgcggccaaa tcacgtttcg    2040
acccgcattc atcgatcgcc gccgccagga cgtcgcgcaa cgccgtcaac gcggtcaacg    2100
catcaccgga cttcgccgcc ttagaaaccg aattacgcgg tgttacaacg tgactcgtag    2160
ttccagcatt acgcctgacc atcagtcaat catccccttg acgtgtggaa atctgccagg    2220
ggagagaaac aagcgacccg gcggcggtcg ccgaggggcc ccctcccctc aagaaaatcg    2280
gcgggtgggg tcgacgtgtg ctcctcgggc attacacgtc ggtgcttggg cgtgggtccg    2340
atcgcaggcg cgcaccgttg gtcggcggtg gctctgtgtt cttctcggcg tgggtcgttg    2400
tgtctggtgt cgcgggtgac cggtcgtggc cggtagctgt tcatgagggc tgtccctctc    2460
cggcggcgag cagcacggtg gccaggtctg cggtgactgc gtcgatggcg gcttctcggc    2520
tgccgtgctc gtattcgtag gcgttggcgg ctgctgcggt caggaagccg aggacgccgg    2580
```

-continued

```
cggtgacttt ctcgccggcg gcgatgatgc gctcgatctc ggtcgtgagg cgtccgtcgt   2640
tgacgaggcc ggccaggagc acgccgagtg ctgtggcgta gagggcggcc agtgcctggt   2700
catcagaggg cgtggggttg tcggtggtca tggtgtgcct ttcgggttgg ggtggatggg   2760
gtgttgcttt ctgggtcggc cgcgctgttg ggtgcggagc tggcccgcta cgacgccgtg   2820
cggccggtgt ctggcgggta gggcgttgaa ccatgcgcgg cagcggtcgg cggccggaca   2880
ccgcgaacac aggccgagga cctgggcgtg gcgctgctca acgacttcgg gggcctcgtt   2940
cggtgctgct tcgtcgaaca ggtgatgccg gccgcggcat ctggcacctg gcaacgacgg   3000
tgcagcggcc agcgcttcga ggaggtggtg cagcgcggtc atcgggtggc tcggttcaac   3060
ggggtcgtcc ctccgggatc gggttttctt gactgttttc cgactgcgtc ccgcgaccgc   3120
gtcctgcgtc ccccctacgg ggggtgggac gcagtcggac gcagtcgcag tccgcttgaa   3180
cgccactgcg tccggacgcg gtgggacgca gtcggacgca gtcacgtgct gtccccatcg   3240
gcgtcctcca caacggccct gaaccccttg gcgccacgct tgcctgatat ctctacgaga   3300
cggcctgaca ccacaaggtc atcgacgacg tcgcgcacat cgtcgtcacg gaactggatg   3360
tcgacgttgc gtaactcagc gaacaacagc cgcatcgacc caacagcgtg gtcgggagcc   3420
gcagcaacga cgcgaaagac agcgtcagcc agctcggcgt tcggatcgct ctcaggcacg   3480
tcgtcgtccc tgggcgcgaa gaaccgcatc gtgaagtcag gaccgaacgc ctgcgagtca   3540
tcgacgacca gagttcccat gaacgtcttg ccgggcgact tcgttgcgcg cccgttggcc   3600
cgtagatgcc cggggcggtc tttggtcacg aagacgtagg agacgccgcg cagccgccgg   3660
ccgaacggcg ccgagttctc gagcacgaac cgagccccgt cgagcgcgtt gcccttatgc   3720
accgaaccgt aggcatcgcg gcggctgccg tcgcgcacca tcgggaggtg gtcgcacgcc   3780
agcgtggccg cgccgacacg taggcatggc aggcatcagt cggccggcga aacgcccgcg   3840
gcgccctcga cggccttgat ctcgtcgccg tgcagcgcca tcgcttcgtt gacgccgtcg   3900
tggatgacca gcgtcggtga agggtcaagt agtgcgttca gccactcctc acggacgggg   3960
cggctgggag cgacgaaccg aaaccgggcc ttgatcaccg cggggtcgac cccaagcaag   4020
cacagcttct cgacggtgct cgtcgcgtcg ggttcttcgt agtggatata cacgacgtcg   4080
ttgccggcgt tgagttctgc ggcggcgcag cccaacgcga accaggtttt accgctttcg   4140
gtttcaccga ctatggcgtg ctcgcgacca gggtagagcg accgctgccc gtcggagcgt   4200
gatatgccga taccgggatg tgggcgttcg atttcgccgc gcaggtaggg tccgagatcg   4260
aacgcctccc acgtggtcgg ctcggcgctt gcctgctgct gtcgttggcc gtttcgctgc   4320
ggtggttcgt ccggcggttc ccacggggga acatcggccc attgcgcggc gaaatcggca   4380
gcggttagca tcgaggagcc ttgcgccgca accat                              4415
```

```

<210> SEQ ID NO 24
<211> LENGTH: 322
<212> TYPE: PRT
<213> ORGANISM: Mycobacterium paratuberculosis

<400> SEQUENCE: 24

Val Arg Pro His Thr Gly Gly Arg Arg Ile Ser Ile Tyr Trp Thr Trp
 1               5                  10                  15

Ser Tyr Pro Trp Glu Ser Gln Arg Asp Ile Gln Thr Leu Asp Asn Arg
            20                  25                  30

Phe Ser Thr Met Thr Glu Val Arg Arg Ala Ala Trp Pro Arg Tyr Glu
        35                  40                  45
```

```
Gly Pro Asp Trp Asp Asp Ala His Phe Leu Gln Gly Ile Ala Gly Thr
         50                  55                  60

Leu Glu Leu Phe His Arg Ser Thr Leu Ala Phe Gln Glu Leu Ala Gly
 65                  70                  75                  80

Glu Ala Thr Gly Gln Gln Val Ala Val Phe Gln Arg Val Asp Gln Ala
                 85                  90                  95

Gly Tyr Arg Leu Val Ile Asp Glu Arg Ile Leu Ala Asp Thr Asp Thr
                100                 105                 110

Leu Met Val Phe Gly Leu Asp His Leu Ala Gly Glu Asp Ala Glu
            115                 120                 125

Pro Gly Glu Ile Ser Ala Ile Arg Ala Trp Leu Glu Arg Glu Gly Thr
130                 135                 140

Cys Leu Leu Ala Pro His His Asp Val Gly Gly Thr Asp Asp Met
145                 150                 155                 160

Ala Gln Arg Gln Val Glu Tyr Leu His His Gly Asp Pro Leu Val Pro
                165                 170                 175

Arg Gln Gln Arg Phe Ser Ala Tyr Thr Arg Ser Leu Met Lys Gly Leu
                180                 185                 190

Asp Val Pro Val Arg Asn Arg Trp Gly Leu His Pro Ala Arg Val Ala
                195                 200                 205

Ala Thr Gly Gln Met Ala Pro Leu Thr Cys Phe Arg Asp Leu Asp Ala
210                 215                 220

Pro Gly Leu Leu Asp Asp Val Thr Thr Leu Asn Phe His Pro His Leu
225                 230                 235                 240

Pro His Tyr Glu Leu Thr Ala Pro Glu Ser Asp Gly Leu Arg Val Leu
                245                 250                 255

Ala Thr Gln Arg Val Asp Pro Ala Arg Pro His Pro Phe Thr Glu Ala
                260                 265                 270

Gly Asn Ser Glu Phe Asn Ala Leu Ile Trp Met Pro Pro His Ala Glu
                275                 280                 285

Arg Ala Gly Asp Ile Val Leu Val Asp Ser Thr Asn Phe Thr Thr Leu
                290                 295                 300

Phe Gly Gly Ser Asp Ser Leu Arg Asn Phe Trp His Asn Leu Ala Thr
305                 310                 315                 320

Met Arg

<210> SEQ ID NO 25
<211> LENGTH: 191
<212> TYPE: PRT
<213> ORGANISM: Mycobacterium paratuberculosis

<400> SEQUENCE: 25

Met Val Ala Thr Glu His Glu Trp Ser Lys Pro Ala Ala Leu Ala Ile
  1               5                  10                  15

Pro Arg Glu Gly Tyr Phe Glu Leu Glu Arg Gly Arg Tyr Gly Pro Leu
                 20                  25                  30

Tyr Pro Arg Thr Pro Ala Cys Tyr Gly Phe Ser Ile Ile Ala Lys Val
             35                  40                  45

Lys Glu Gly Arg Glu Glu Ala Val Arg Ala Tyr Gly Lys Gln Ile Glu
 50                  55                  60

Glu Ala Ile Lys Ala Asp Pro His Val Leu Ala Leu Arg Leu His
 65                  70                  75                  80

Tyr Leu Arg Trp Leu Leu Phe Asp Val Gly Ser Gly Leu His Phe Gln
                 85                  90                  95
```

```
Tyr Gln Gly Ile Phe Asp Thr Asp Phe Asp Lys Tyr Thr Glu Asp Ala
            100                 105                 110

Val Gln Leu Phe Ser Gln Thr Gly Ile Thr Thr Val Phe Thr Asn Leu
        115                 120                 125

Glu Gly Phe Pro Glu Asp Trp Arg Glu Asn Pro Asp Ala Phe Val Lys
    130                 135                 140

Phe Val Arg Glu His Gln Cys Pro Ser Phe Leu Glu Tyr Gly Glu Tyr
145                 150                 155                 160

Pro Tyr Val Thr Ala Asp Glu Ile Lys Lys Ala Tyr Gly Ser Ser Arg
                165                 170                 175

Leu Pro Asp His Ala Gly Ser Asp Ala Met Thr Ser Val Arg Val
            180                 185                 190
```

<210> SEQ ID NO 26
<211> LENGTH: 173
<212> TYPE: PRT
<213> ORGANISM: Mycobacterium paratuberculosis

<400> SEQUENCE: 26

```
Met Val Val Ser Ile Ser Ala Pro Thr Val Pro Ile Pro Gln Ala Met
1               5                   10                  15

Thr Phe Ser Gly Leu Arg Ser Asp Ile Gly Gln Lys Pro Thr Arg Gly
            20                  25                  30

Gln His Arg Gln Arg Asp Ala Ala Ile Phe Glu Leu Pro Val Arg Pro
        35                  40                  45

Met Arg Asp Val Gly His Phe Asp Phe Leu Pro Ala Leu Arg Phe Gly
    50                  55                  60

Val Arg Pro Pro Asp Val Asp Asp Gln Val Ala Gly Leu Val Gly Arg
65                  70                  75                  80

Val Gln Ile Arg Pro Val Arg Ile Asp Thr Gly Gly His Asp Leu Glu
                85                  90                  95

Gly Thr Asp Ile Val Arg Arg Gln Arg Arg His Pro Thr Ala Val Ala
            100                 105                 110

Asp Gly Gly Gly Val Ala Trp Asp Ala His Pro His Arg Val Ala Arg
        115                 120                 125

Ser Cys Pro Glu Ala Leu His Gly Cys Ser Gly Val Gly Glu Arg Ala
    130                 135                 140

Gln Gly Gly Met Gln Ile Glu Asp Arg Ser Lys Val Ile Cys Ala Asp
145                 150                 155                 160

Ala Lys Pro Glu Ala Ala Leu Met Arg Ala Glu Pro Thr
                165                 170
```

<210> SEQ ID NO 27
<211> LENGTH: 193
<212> TYPE: PRT
<213> ORGANISM: Mycobacterium paratuberculosis

<400> SEQUENCE: 27

```
Met Asn Thr Ser Ser Ser Leu Pro Val Asp Thr Leu Asp Val Thr Ala
1               5                   10                  15

Pro Pro Asp Ala Thr Glu Val Tyr Gly Trp Ala Ala His Pro Asp Gly
            20                  25                  30

Leu Ala Ala Arg Ala Phe Glu Ala Val Arg Asp Cys Ala Gly Tyr
        35                  40                  45

Arg Val Arg Val Arg Gly Ala Gln Arg Ser Asn Val Thr Cys Arg Arg
    50                  55                  60
```

```
Trp Val Ala Ile Glu Ala Ala Pro Gly Ala Asp Glu Gln Ala Leu Glu
 65                  70                  75                  80

Pro Glu Ala Val Arg Gln Leu Ala Pro Gln Met Ser Val Thr Pro Thr
                 85                  90                  95

Thr Arg Arg Thr Ala Glu Met Leu Asp Asp Ala Ala Phe Asp Ala Ile
            100                 105                 110

Val Ala Val Phe Ser Gln Arg Ala Arg Cys Glu Met Gln Thr Leu Ser
        115                 120                 125

Gly Gly Lys Cys Pro Arg Ala Ala Arg Trp Arg Ile Asp Leu His Gly
    130                 135                 140

Cys Glu Gln Ala Ile Val Cys Gly Gln His Lys Lys Ala Trp Leu Gln
145                 150                 155                 160

Glu Ala Leu Ala Asn Leu Trp Arg Gly Ile Gln Pro Arg Cys Ala His
                165                 170                 175

Cys Gly Arg Val Phe Asn Ser Phe Gln Asp Ala Val Arg Ile Thr Ala
            180                 185                 190

Ile

<210> SEQ ID NO 28
<211> LENGTH: 103
<212> TYPE: PRT
<213> ORGANISM: Mycobacterium paratuberculosis

<400> SEQUENCE: 28

Met Ala Thr Asn Asp Asp Gln Asp Asp Gly Lys Pro Pro Ile Thr Ala
  1               5                  10                  15

Ala Ala Gly Gly Asp Glu Thr Ala Ile Gly Ala Ala Ala Asp Glu Thr
                 20                  25                  30

Glu Leu Val Ala Pro Leu Thr Val Pro Ala Ser Glu Leu Ala Trp Ser
            35                  40                  45

His Glu Asp Ser Asp Ala Gly Asp Tyr Ser Trp Gly Arg Ala Ala Glu
         50                 55                  60

Arg Ala Ser Ile Ile Val Leu Ala Cys Ala Ala Val Ala Val Val Ile
 65                 70                  75                  80

Gly Leu Leu Thr Trp Leu Ala Leu His Leu His Asp Gln Ala Lys Pro
                85                  90                  95

Thr Ala Gly Pro Thr Ala Ala
            100

<210> SEQ ID NO 29
<211> LENGTH: 191
<212> TYPE: PRT
<213> ORGANISM: Mycobacterium paratuberculosis

<400> SEQUENCE: 29

Met Ser Ala Arg Asp Leu Ile Asn Ile Gly Val Phe Gly Ala Leu Tyr
  1               5                  10                  15

Ile Ala Thr Val Phe Ala Ile Asn Val Phe Ala Phe Ile Asn Pro Leu
                 20                  25                  30

Val Met Leu Val Ala Leu Ala Val Ser Met Ile Ala Gly Val Pro
            35                  40                  45

Phe Met Leu Phe Leu Thr Arg Val Arg His Ala Gly Met Val Thr Val
         50                  55                  60

Phe Ala Ile Ile Thr Ala Gly Leu Leu Ala Leu Thr Gly His Pro Pro
 65                 70                  75                  80

Ile Cys Phe Val Ile Thr Val Ala Cys Ala Leu Val Ala Glu Val Val
```

```
                        85                  90                  95
Leu Trp Leu Gly Arg Tyr Arg Ser Arg Thr Met Gly Val Leu Ala Tyr
            100                 105                 110

Ala Ile Tyr Ala Ala Trp Tyr Ile Gly Pro Leu Leu Pro Ile Phe Tyr
            115                 120                 125

Ala Arg Asp Glu Tyr Phe Ser Ser Pro Gly Met Ala Gln Met Gly Pro
            130                 135                 140

Arg Tyr Leu Glu Glu Met Glu Arg Leu Leu Ser Pro Ala Val Leu Ile
145                 150                 155                 160

Ala Phe Asp Leu Ser Thr Val Val Phe Gly Leu Ile Gly Gly Leu Leu
                165                 170                 175

Gly Val Arg Leu Leu Arg Lys His Phe Gln Arg Ala Gly Leu Ala
            180                 185                 190

<210> SEQ ID NO 30
<211> LENGTH: 157
<212> TYPE: PRT
<213> ORGANISM: Mycobacterium paratuberculosis

<400> SEQUENCE: 30

Met Ala Gly Met Pro Glu Val Ala Ala Leu Leu Arg Gly Phe Pro
1               5                   10                  15

Arg Ile Gly Ala Arg Glu Gln Ala Phe Ala Phe Leu Thr Val Asp Thr
            20                  25                  30

Gly Gly Phe Pro His Ala Ala Leu Leu Ser Arg Cys Glu Leu Glu Pro
            35                  40                  45

Gly Arg Asp Pro Gln Thr Leu Met Ala Ala Ile Ala Ser Arg Gln Thr
        50                  55                  60

Arg Ala Asn Leu Arg Arg Ser Gly Thr Ala Gly Leu Leu Ala Ile Asn
65                  70                  75                  80

Gly Thr Ser Cys His His Leu Lys Leu Arg Val Val Ala Ser Leu Val
                85                  90                  95

Gly Arg Gly Ile Leu Gly Cys Val Phe Ala Val Thr Glu His Lys Arg
            100                 105                 110

Asp Asp Met Gly Ile Pro Leu Gln Pro Thr Leu Phe Arg Thr Ser Ala
            115                 120                 125

Glu Ile Ser Val Leu Glu Asp Trp Pro Arg Ser Arg Ala Met Phe Asp
        130                 135                 140

Arg Leu Ala Ala Leu Arg Ser Ala Ala Arg Glu Val Leu
145                 150                 155

<210> SEQ ID NO 31
<211> LENGTH: 185
<212> TYPE: PRT
<213> ORGANISM: Mycobacterium paratuberculosis

<400> SEQUENCE: 31

Met Arg Phe Ala Leu Pro Thr Arg Ile Leu His Trp Leu Met Ala Pro
1               5                   10                  15

Met Val Ile Gly Gln Leu Leu Ile Gly Val Val Met Ile Thr Ser Leu
            20                  25                  30

Thr Tyr Tyr Pro Leu Leu Leu Ala Ile His Arg Pro Leu Gly Ala Leu
            35                  40                  45

Ile Leu Ala Phe Ala Val Val Arg Leu Ala Asn Arg Phe Thr His Arg
        50                  55                  60

Leu Pro Pro Phe Leu Ala Thr Met Gly Pro Val Glu Arg Arg Val Ala
```

```
                65                  70                  75                  80
Thr Trp Ser Glu Tyr Leu Leu Tyr Ala Leu Leu Ala Gln Pro Leu
                    85                  90                  95
Ile Gly Trp Ala Met Leu Ser Ala Ala Arg Phe Pro Val Val Leu Val
                100                 105                 110
Gly Pro Val His Leu Pro Gly Ile Ala Pro His Asn Val Asp Val Tyr
                115                 120                 125
Ala Ala Leu Arg Gln Ala His Asn Val Gly Ala Phe Leu Leu Phe Leu
            130                 135                 140
Thr Phe Thr Ala His Val Cys Ala Val Leu Phe His Thr Leu Gly Leu
145                 150                 155                 160
Arg Asp Arg Leu Leu Asp Arg Met Ala Leu Trp Pro Thr Lys Pro Val
                165                 170                 175
Ala Ser Arg Gln Asp Glu Ile Lys Ala
                180                 185

<210> SEQ ID NO 32
<211> LENGTH: 106
<212> TYPE: PRT
<213> ORGANISM: Mycobacterium paratuberculosis

<400> SEQUENCE: 32

Leu Arg Arg Leu Met Ala Glu Arg Gly Leu Phe Asn Thr Thr Ala Leu
1               5                   10                  15
Arg Pro Leu Leu Ala Glu Arg Gly Val Gln Leu Ser Ala Ser Gln Val
                20                  25                  30
Tyr Arg Leu Val Thr Glu Lys Pro Glu Arg Leu Ser Leu Pro Thr Leu
            35                  40                  45
Val Ala Leu Val Asp Ile Leu Arg Cys Ala Met Asp Glu Leu Ile Glu
        50                  55                  60
Ile Val Pro Ala Thr Ala Ala Ser Ala Lys Lys Ala Ala Gly Ala Pro
65                  70                  75                  80
Glu Arg Ser Lys Pro Val Arg Thr Arg Glu Leu Gly Gly His Arg Pro
                85                  90                  95
Val Arg Ala Lys Ile Val Asp Ala Asp Ser
                100                 105

<210> SEQ ID NO 33
<211> LENGTH: 835
<212> TYPE: PRT
<213> ORGANISM: Mycobacterium paratuberculosis

<400> SEQUENCE: 33

Met Arg Gly Asn Arg Ser Glu Phe Val Thr Val Ile Val Thr Ala Val
1               5                   10                  15
Gly Ala Ile Glu Pro His Leu Ser His Asp Asp Val Arg Thr Ala Ile
                20                  25                  30
Glu Gly Met Gly Leu Ser Ala Ala Gln Leu Gln Arg Leu Ser Arg Thr
            35                  40                  45
Leu Arg Arg Asp Gly Ser Val Leu Thr Gly Pro Gly Gly Ser Asp Cys
        50                  55                  60
Ala Ala Asp Ile Glu Gln Leu Ile Leu Cys Leu Arg Gln Leu Gly Ala
65                  70                  75                  80
Met Arg Val Arg Ala Pro Arg Cys Ala Gln Cys Gly Arg Asn Asp Ser
                85                  90                  95
Glu Thr Tyr Ser Arg Lys Leu Lys Lys Arg Ile Cys Arg Ala Cys Ser
```

```
              100                 105                 110
Met Gln Gly Trp Gln Pro Ala Val Gly Glu Cys Pro Gly Cys Gly Ala
            115                 120                 125

Val Asp Lys Leu Ile Tyr Arg Pro Arg His Gly Asp Gly Leu Leu Cys
130                 135                 140

Arg Arg Cys Lys Pro Glu Pro Asp Val Asp His Ala Ala Lys Val Arg
145                 150                 155                 160

Asp Gly Ile Ala Gln Leu Arg Thr Gly Leu Ser Ala Thr Glu Ile Asp
                165                 170                 175

Arg Val Ala Ser Val Phe Gly Thr Ala Val Ala Gln Arg Glu Leu Asn
            180                 185                 190

Trp Ile Leu Gln Asp Thr Pro Gly Val Phe Arg Gly Glu Ile Ala His
        195                 200                 205

Arg Ser Ala Val Ser Val Arg Leu Ala Glu Leu Leu Val Ala Ala Gly
    210                 215                 220

Ala Asp Asn Val Arg Leu Pro Gln Cys Pro Leu Cys Leu Arg Thr Val
225                 230                 235                 240

Lys Leu Gly Ser Gln Ile Asp Gly Leu Arg Cys Cys His Thr Cys Trp
                245                 250                 255

Gly His His Phe Ser Arg Gly Thr Cys Ala Arg Cys Gly Cys Gln Arg
            260                 265                 270

His Leu Ile Asn Tyr His Gly Ala Gly Glu Arg Leu Cys His Arg Cys
        275                 280                 285

Phe Glu His Asp Pro Val Asn His Glu Pro Cys Thr Arg Cys Gly Arg
    290                 295                 300

Val Asp Phe Ile Asn His His Asp Gly Gln Ala Lys Leu Cys Arg Arg
305                 310                 315                 320

Cys Tyr Pro Ala Pro Thr Ala Val Cys Ser Ser Cys Gly Arg Thr Arg
                325                 330                 335

Pro Cys Thr Arg Thr Arg Thr Gly Lys Pro Ile Cys Gly Thr Cys Ser
            340                 345                 350

Ala Lys Gln Arg Pro Pro Gln Pro Cys Ser Val Cys Gly Asn Ile Arg
        355                 360                 365

Ser Val His Thr Arg Thr Asp Ala Gly Glu Pro Val Cys Asn Pro Cys
    370                 375                 380

Ala Arg Ser Arg Glu Pro Cys Ala Arg Cys Gly Lys Thr Leu Gly Val
385                 390                 395                 400

Ser Ala Arg Leu Ala Gly Val Gly Pro Leu Cys Ser Ala Cys Leu Gln
                405                 410                 415

Arg Glu Pro Ala Tyr Phe Thr Asp Cys Val Gln Cys Gly Ala His Gly
            420                 425                 430

Arg Thr Tyr His Arg Gly Leu Cys Pro Ala Cys Ala Cys Pro Gly Glu
        435                 440                 445

Leu Arg Glu Leu Phe Ala Lys Asn Gly Glu Leu Ser Gly Ala Ala Ser
    450                 455                 460

Arg Ile Val Glu Ala Leu Leu Gln Cys Asp Ala Met Pro Val Leu Arg
465                 470                 475                 480

Trp Val Arg Arg Met Arg Ser Asn Ser Glu Leu Pro Ala Gln Leu Ala
                485                 490                 495

Glu Leu Gly Asp Thr Leu Ser His His Asp Leu Asp Asp Leu Pro Ala
            500                 505                 510

Ser Lys Ser Val Glu Trp Leu Arg Asn Ile Leu Val Thr Ala Glu Gly
        515                 520                 525
```

```
Leu Pro Asp Arg Asp Pro Tyr Leu His Arg Thr Glu Gln Tyr Ile Ala
        530                 535                 540

Ala Arg Leu Ala Thr Ile Ser Asn Arg Asp Asp Arg Ala Ala Val Arg
545                 550                 555                 560

Ala Phe Thr Glu Trp Asn His Leu Arg Lys Leu Arg Ala Arg Ala Asp
                565                 570                 575

Lys Gly Pro Leu Lys Arg Asn His Gly Leu Ala Ala Gln Ile Met Ala
            580                 585                 590

Ala Ala Ile Thr Asp Phe Val Ser Glu Leu Asn Ala His Gly Leu Ala
        595                 600                 605

Leu Ala Ser Cys Gln Gln Ala Phe Val Asp Asp Trp Leu Val Arg Asn
    610                 615                 620

Pro Thr Arg Arg Gln Ile His Gln Phe Leu Ala Trp Ala Val His Arg
625                 630                 635                 640

Gly Tyr Ala His Asp Val Ala Ala Pro Val Pro Gln Thr Arg Arg Thr
                645                 650                 655

Arg His Thr Leu Pro Gly Asp Asp Glu Arg Trp Arg Leu Ile Gln Tyr
            660                 665                 670

Leu Ile Glu His Pro Asp Leu Glu Thr Arg Asp Arg Val Ala Gly Leu
        675                 680                 685

Leu Val Leu Leu Tyr Ser Gln Pro Ala Ala Arg Leu Val Thr Leu Lys
    690                 695                 700

Val Ala Asp Val Thr Ile Thr Asp Asp Ala Val Gln Leu Thr Leu Gly
705                 710                 715                 720

Ala Val Pro Leu Thr Val Pro Ser Pro Val Asp Arg Leu Leu Ala Asp
                725                 730                 735

Leu Val Gln Gln Arg Arg Gly Tyr Ala Ala Val Thr Val Gly Thr Asn
            740                 745                 750

Pro Trp Leu Phe Pro Gly Gly Arg Ser Gly Gly His Leu Ser Ala Asn
        755                 760                 765

Gln Val Gly Leu Arg Leu Lys Arg Ile Gly Ile Ser Pro Arg Ile Ala
    770                 775                 780

Arg Asn Thr Ala Leu Ile Asp Leu Ala Gly Glu Leu Pro Ala Val Val
785                 790                 795                 800

Leu Ala Lys Leu Leu Gly Phe Ser Ile Lys Arg Ala Val Thr Trp Ser
                805                 810                 815

Glu Glu Ala Gly Asn Thr Arg Pro Arg Tyr Ala Ala Glu Val Ala Arg
            820                 825                 830

Arg Asn Ser
        835

<210> SEQ ID NO 34
<211> LENGTH: 87
<212> TYPE: PRT
<213> ORGANISM: Mycobacterium paratuberculosis

<400> SEQUENCE: 34

Val Ser Thr Ser Thr Glu Arg Arg Leu Arg Leu Gln Val Ala Val His
1               5                   10                  15

Glu Ser Trp Ala Arg Thr Glu Asn Arg Ser Ala Arg Thr His Asn Ala
            20                  25                  30

Arg Lys Ala Ala Trp Asp Arg Phe Glu Lys Gln Val Asp Pro Glu Gly
        35                  40                  45

Lys Leu Pro Pro Ala Leu Arg Ala Lys Met Ala Glu Asn Ala Arg Ala
```

```
                   50                  55                  60
Ala His Phe Lys Lys Met Ala Leu Lys Ser Val Glu Ser Arg Arg Arg
 65                  70                  75                  80

Arg Arg Asp Gly Val Ala Ala
                 85

<210> SEQ ID NO 35
<211> LENGTH: 369
<212> TYPE: PRT
<213> ORGANISM: Mycobacterium paratuberculosis

<400> SEQUENCE: 35

Val Pro Tyr Ala Glu Ser Pro Arg Thr Arg Thr Gly Val Phe Thr
  1               5                  10                  15

Leu Glu Gln Ala Gln Pro Asp Asp Gly Leu Val Val Arg Ala Ala
                 20                  25                  30

Gly Leu Gly Gln Arg Ala Ile Gly Asp Asp Ser Gly Val Gly Leu Asp
                 35                  40                  45

Gly Lys Val Gly Phe Glu Ala Val Leu Ala Ala Val His Arg Leu Val
 50                  55                  60

Ser Val Pro Arg Val Gly Ile Asp Gly Gly Asp His Ala Ile Pro Thr
 65                  70                  75                  80

Asp Leu Leu Arg Asp Ala Pro Val Pro Val Gly Ala Ile Arg Ala Leu
                 85                  90                  95

Asp Arg Phe Asn Val Leu Thr Gly Asp Gln Arg Gln Arg His Arg
                100                 105                 110

Leu Ser Ser Pro Arg Arg Glu Phe Leu Val Arg Gln Ile Ala Gln His
                115                 120                 125

Pro Val Ser Ile Thr Asp Gln Thr Ile His Gln Pro Ile Pro Ser Gly
                130                 135                 140

Leu Ile Leu Pro Arg Asn Arg Gly Phe Pro Arg Ile Val Val Ile Met
145                 150                 155                 160

Gly Ala Ala Val Gly Phe Asp His Arg Cys Ser Ala Arg Asp Phe Ala
                165                 170                 175

Ala His Ser Ser Asp Arg Gly Asp Gln Leu Arg His Gly Val Leu Arg
                180                 185                 190

Gly His Arg Ile Val Glu His Arg Gly Ile Gln Gly Pro Pro Cys Leu
                195                 200                 205

Ala Arg Gln His Pro Gly Leu Gly His His Arg Leu Asp Arg Leu Glu
                210                 215                 220

Asp Pro Val Gly Pro Ile Arg Ser Arg Gln Pro Thr Pro Ile Arg
225                 230                 235                 240

Gln Arg Arg Arg Met Lys Arg Ala Arg Asp Arg Gln Pro Ala Arg
                245                 250                 255

Cys Phe Pro Ala Gln Ile Glu Ser His Arg Ile His Gly Leu Val Ile
                260                 265                 270

Arg Lys Thr Val Gln Gly Leu Gln Gly Asp His Arg Gly His His Leu
                275                 280                 285

Ser Arg His Ala Gly Pro Ala Pro Leu Arg Arg Glu Gln Val Arg Glu
                290                 295                 300

His Leu Leu Gly Lys Gln Leu Ala Ala Val Arg Arg Gln Glu Arg Lys
305                 310                 315                 320

His Ala Val Gly Leu Gln Lys Met Pro Gly Asn Arg Leu Arg Ile Gln
                325                 330                 335
```

```
Gln Leu Thr Leu Ile Ile Arg Ala Thr Leu His Pro Thr Ile Ile Pro
                340                 345                 350

Lys Thr Pro Gly Gln Leu Val Pro Pro Arg Gly Ile Asn Ser Ala Gly
        355                 360                 365

Ser

<210> SEQ ID NO 36
<211> LENGTH: 223
<212> TYPE: PRT
<213> ORGANISM: Mycobacterium paratuberculosis

<400> SEQUENCE: 36

Leu Val Ile Ala Leu Ala Ala Leu Trp Ser Ile Arg Leu Ala Trp His
  1               5                  10                  15

Ile Pro Phe Glu Arg Ala Ala Val Ala Leu Ala Phe Met Cys Ala
             20                  25                  30

Gln Leu Val Leu Ala Leu Gly Pro Val Asp Gly Trp Leu Ser Pro Leu
         35                  40                  45

Leu His Asp Met Thr Gly Val Trp Asn Leu Glu Asp Leu Ile Gly His
     50                  55                  60

Leu Leu Tyr Val Tyr Gly Leu Phe Ser Ile Met Tyr Leu Val Ala Asp
 65                  70                  75                  80

His Cys Asp Met Thr Pro Gly Gln Leu Arg Trp Phe Val Arg Asn Arg
                 85                  90                  95

Leu Glu Leu Pro Ser Val Val Ile Cys Ala Val Met Ile Ala Val Phe
            100                 105                 110

Val Ala Gly Asp Ile Gly Glu Thr Cys Val Pro Asp Val Val Ala Thr
        115                 120                 125

Glu His Thr Pro Trp Leu Arg Val Tyr Trp Phe Val Met Ile Ala Ala
    130                 135                 140

Leu Ala Tyr Ile Ile Val Ser Thr Gly Arg Ile Leu Leu Ile Leu Arg
145                 150                 155                 160

Gln His Pro Arg Ser Arg His Ala Ala Thr Ala Tyr Leu Val Ala Leu
                165                 170                 175

Gly Ile Thr Gly Ala Cys Cys Val Val Phe Ile Ile Gly Ile Pro Trp
            180                 185                 190

Leu Gln Trp Leu Leu Val Arg Cys Glu Val Val Gly Tyr Ala Val Ala
        195                 200                 205

Ala Ser Tyr Ser Trp Arg Asn Lys Val Ala Tyr Phe Arg Gly Arg
    210                 215                 220

<210> SEQ ID NO 37
<211> LENGTH: 123
<212> TYPE: PRT
<213> ORGANISM: Mycobacterium paratuberculosis

<400> SEQUENCE: 37

Leu His Glu Ile Leu Arg Phe Gly Gly Lys Thr Asp Glu Leu Ile Gly
  1               5                  10                  15

Phe Ala Arg Ala Leu Ser Val Gln Thr Ala Thr Leu Pro Gly Met Ser
             20                  25                  30

Ser His Ser Pro Val Ser Ala Ala Ala Leu Ala Ser Arg Leu Arg Met
         35                  40                  45

Ile Met Gly Asp Arg Lys Leu Ser Arg Thr Arg Leu Ser His Glu Thr
     50                  55                  60

Gly Ile Ser Arg Pro Ser Leu Ser Ser Lys Leu Asp Gly Lys Val Glu
```

```
                65                   70                  75                  80
       Phe Thr Tyr Ser Glu Leu Leu Thr Ile Ala Gln Ala Val Asp Val Pro
                       85                  90                  95

Leu Asp Lys Leu Leu Ala Gly Asp Asp Glu Arg Pro Phe Arg Leu
                   100                 105                 110

Ser Asp Leu Arg Pro Arg Pro Asp Arg Pro Leu
               115                 120

<210> SEQ ID NO 38
<211> LENGTH: 199
<212> TYPE: PRT
<213> ORGANISM: Mycobacterium paratuberculosis

<400> SEQUENCE: 38

Met Val Ala Ala Gln Gly Ser Ser Met Leu Thr Ala Ala Asp Phe Ala
 1               5                  10                  15

Ala Gln Trp Ala Asp Val Pro Pro Trp Glu Pro Pro Asp Glu Pro Pro
                20                  25                  30

Gln Arg Asn Gly Gln Arg Gln Gln Ala Ser Ala Glu Pro Thr Thr
            35                  40                  45

Trp Glu Ala Phe Asp Leu Gly Pro Tyr Leu Arg Gly Glu Ile Glu Arg
    50                  55                  60

Pro His Pro Gly Ile Gly Ile Ser Arg Ser Asp Gly Gln Arg Ser Leu
65                  70                  75                  80

Tyr Pro Gly Arg Glu His Ala Ile Val Gly Glu Thr Glu Ser Gly Lys
                85                  90                  95

Thr Trp Phe Ala Leu Gly Cys Ala Ala Ala Glu Leu Asn Ala Gly Asn
                100                 105                 110

Asp Val Val Tyr Ile His Tyr Glu Pro Asp Ala Thr Ser Thr Val
            115                 120                 125

Glu Lys Leu Cys Leu Leu Gly Val Asp Pro Ala Val Ile Lys Ala Arg
        130                 135                 140

Phe Arg Phe Val Ala Pro Ser Arg Pro Val Arg Glu Glu Trp Leu Asn
145                 150                 155                 160

Ala Leu Leu Asp Pro Ser Pro Thr Leu Val Ile His Asp Gly Val Asn
                165                 170                 175

Glu Ala Met Ala Leu His Gly Asp Glu Ile Lys Ala Val Glu Gly Ala
            180                 185                 190

Ala Gly Val Ser Pro Ala Asp
        195

<210> SEQ ID NO 39
<211> LENGTH: 179
<212> TYPE: PRT
<213> ORGANISM: Mycobacterium paratuberculosis

<400> SEQUENCE: 39

Met Val Arg Asp Gly Ser Arg Arg Asp Ala Tyr Gly Ser Val His Lys
 1               5                  10                  15

Gly Asn Ala Leu Asp Gly Ala Arg Phe Val Leu Glu Asn Ser Ala Pro
                20                  25                  30

Phe Gly Arg Arg Leu Arg Gly Val Ser Tyr Val Phe Val Thr Lys Asp
            35                  40                  45

Arg Pro Gly His Leu Arg Ala Asn Gly Arg Ala Thr Lys Ser Pro Gly
        50                  55                  60

Lys Thr Phe Met Gly Thr Leu Val Val Asp Asp Ser Gln Ala Phe Gly
```

```
                65                  70                  75                  80
Pro Asp Phe Thr Met Arg Phe Ala Pro Arg Asp Asp Val Pro
                        85                  90                  95
Glu Ser Asp Pro Asn Ala Glu Leu Ala Asp Ala Val Phe Arg Val Val
                100                 105                 110
Ala Ala Ala Pro Asp His Ala Val Gly Ser Met Arg Leu Leu Phe Ala
            115                 120                 125
Glu Leu Arg Asn Val Asp Ile Gln Phe Arg Asp Asp Asp Val Arg Asp
        130                 135                 140
Val Val Asp Asp Leu Val Val Ser Gly Arg Leu Val Glu Ile Ser Gly
145                 150                 155                 160
Lys Arg Gly Ala Lys Gly Phe Arg Ala Val Val Glu Asp Ala Asp Gly
                165                 170                 175
Asp Ser Thr

<210> SEQ ID NO 40
<211> LENGTH: 96
<212> TYPE: PRT
<213> ORGANISM: Mycobacterium paratuberculosis

<400> SEQUENCE: 40

Met Thr Thr Asp Asn Pro Thr Pro Ser Asp Asp Gln Ala Leu Ala Ala
1               5                   10                  15
Leu Tyr Ala Thr Ala Leu Gly Val Leu Leu Ala Gly Leu Val Asn Asp
                20                  25                  30
Gly Arg Leu Thr Thr Glu Ile Glu Arg Ile Ile Ala Ala Gly Glu Lys
            35                  40                  45
Val Thr Ala Gly Val Leu Gly Phe Leu Thr Ala Ala Ala Asn Ala
        50                  55                  60
Tyr Glu Tyr Glu His Gly Ser Arg Glu Ala Ala Ile Asp Ala Val Thr
65                  70                  75                  80
Ala Asp Leu Ala Thr Val Leu Leu Ala Ala Gly Glu Gly Gln Pro Ser
                85                  90                  95

<210> SEQ ID NO 41
<211> LENGTH: 74
<212> TYPE: PRT
<213> ORGANISM: Mycobacterium paratuberculosis

<400> SEQUENCE: 41

Leu Thr Ala Leu Thr Ala Leu Arg Asp Val Leu Ala Ala Ala Ile Asp
1               5                   10                  15
Glu Cys Gly Ser Lys Arg Asp Leu Ala Ala Leu Leu Arg Gln Phe Thr
                20                  25                  30
Ala Val Leu Ala Gln Ile Glu Ala Ala Arg Val Arg Pro Pro Gln Arg
            35                  40                  45
Arg Ile Ala Asp Glu Ile Ala Ala Arg Arg Thr Ala Arg Gln Ala Ala
        50                  55                  60
Ala Ala Ala Asp Ala Lys Ser Ala Asp Arg
65                  70

<210> SEQ ID NO 42
<211> LENGTH: 146
<212> TYPE: PRT
<213> ORGANISM: Mycobacterium paratuberculosis

<400> SEQUENCE: 42
```

-continued

```
Met Ser Asp Glu Leu Arg Gln Arg Tyr Lys Val Ile Phe Asp Ala Val
 1               5                  10                  15

Arg Val Ser Glu Ile Glu Ile Thr Pro Asp Leu Ala Arg Cys Leu Val
                20                  25                  30

His Trp Leu Gly Asp Tyr Ile Arg Leu Lys Gln Gln Pro Gly Gln Pro
                35                  40                  45

Gly Val Pro Glu Gly Leu Val Ala Ala Gln Thr Ala Leu Ala Glu Ala
        50                  55                  60

Tyr Ala Ala Val Thr His Ser Pro Arg Ser Glu Arg Asp Arg Pro Ile
 65                  70                  75                  80

Gly Ala Gly Phe Val Phe Ser Ala His Asp Ala Trp Val Gly Thr Ala
                85                  90                  95

Glu Ala Ala Glu Met Leu Gly Ile Lys Ala Gly Ser Val Gly Trp Leu
                100                 105                 110

Cys Arg Glu Ser His Leu Glu His Arg Lys Val Gly Arg Gln Tyr Met
                115                 120                 125

Ile Ser Thr Ala Ser Ile Glu Asp Tyr Lys Arg Arg Lys Ala Glu Arg
        130                 135                 140

Ser Ala
145

<210> SEQ ID NO 43
<211> LENGTH: 241
<212> TYPE: PRT
<213> ORGANISM: Mycobacterium paratuberculosis

<400> SEQUENCE: 43

Met Val Asn Val Pro Arg Ala Glu Leu Ala Arg Leu Val Gly Val Ser
 1               5                  10                  15

Pro Asp Val Asp Asp Leu Thr Leu Gln Gln Ala Ile Asp Ser Lys Leu
                20                  25                  30

Ala Gln Asn Glu Ala Glu Lys His Ala His Ala Val Ser Ala Ala Glu
                35                  40                  45

Gln Arg Ala Arg Ala Asp Asp Arg Arg Ile Val Ile Ala Ala Tyr Asn
 50                  55                  60

Glu Gly Arg Ile Pro Gln Ser Arg Ile Asp Phe Trp Cys Glu Ala Met
 65                  70                  75                  80

Gln Arg Asp Arg Ala Gly Asn Arg Ala Ile Leu Ala Leu Ala Pro
                85                  90                  95

Gly Leu Ala Pro Pro Glu Lys Leu Pro Thr Asp Pro Gln Ile Glu His
                100                 105                 110

Val His Ala Lys Val Leu Ala Arg Met Gly Ile Arg Pro Pro Ala Ser
                115                 120                 125

Ala Pro Thr Ser Gln Thr Val Ala Ala Ser Ser Pro Pro Ser Pro
        130                 135                 140

Gly Val Asp Asp Leu Gly Ile Pro Ile Ala Pro Leu Pro Pro Pro Val
145                 150                 155                 160

Arg Ile Val Arg Ile Val His Gly Lys Asp Pro Ala Thr Trp Ser Lys
                165                 170                 175

Glu Glu Arg Asp Asn Ala Leu Leu Tyr Gly Leu Gly Pro Arg Phe Ala
                180                 185                 190

Ala Ala Ala Ala Ala Arg Gly Ile Pro Arg Pro Pro Gly Gly Ser Gly
                195                 200                 205

Tyr Tyr Gln Pro Thr Gly Ile Glu Pro Tyr Glu Pro Val Asp Leu Gly
        210                 215                 220
```

```
Gly Gly Gln Ile Glu Trp Arg Ala Lys Pro Asp Tyr Arg Pro Arg Gly
225                 230                 235                 240

Asp

<210> SEQ ID NO 44
<211> LENGTH: 141
<212> TYPE: PRT
<213> ORGANISM: Mycobacterium paratuberculosis

<400> SEQUENCE: 44

Met Ala Tyr Arg Met Ser Pro Arg Val Glu Met Leu Ala Val Lys Asp
 1               5                  10                  15

Gln Asn Gly Ile Ile Trp His His Tyr Gln Arg Pro Val Gly Gly Ala
            20                  25                  30

Arg Asn Leu Gly Pro Ile Ile Ala Trp Ile Gly Pro Asp Tyr Arg Asp
        35                  40                  45

Arg Trp Leu Arg Met Gly Leu Ile Glu Glu Ile Pro Asp Ala Ala
    50                  55                  60

Ala Ala Leu Ser Gln Pro Pro Ser Asp Ala Val Ala Gly Pro Asn
65                  70                  75                  80

Thr Asp Leu Val Asp Glu Cys Ile Ala Ala Leu Asp Arg Phe Asp Val
                85                  90                  95

Pro Ala Asp Ala Gly Ala Pro Thr Ala Arg Lys Ala Leu Arg Asp Arg
            100                 105                 110

Gly Gln Ala Trp Gly Asn Glu Thr Ile Ala Ala Val Arg Ala Arg
        115                 120                 125

Lys Ala Arg Ala Ala Pro Ser Gly Thr Pro Ala Gly Ser
    130                 135                 140

<210> SEQ ID NO 45
<211> LENGTH: 92
<212> TYPE: PRT
<213> ORGANISM: Mycobacterium paratuberculosis
<220> FEATURE:
<221> NAME/KEY: VARIANT
<222> LOCATION: 79
<223> OTHER INFORMATION: Xaa = Unknown

<400> SEQUENCE: 45

Met Ser Thr Thr Thr Val Pro Val Gly Thr Thr Pro Ala Ala Ile Thr
 1               5                  10                  15

Gly Ile Pro Pro Asp Val Asp Ser Val Gln Val Leu Asn Ser Ser Glu
            20                  25                  30

Gly Leu Gly Asp Ala Ala Gly Val Asp Ile Val Val Asn Asn Ser Gly
        35                  40                  45

Gly Cys Ser Leu Asp Pro Gln Thr Gly Ile Arg Leu Lys Pro Gly Glu
    50                  55                  60

Phe Phe Val Phe Ser Leu Arg Gln Pro His Gly Gly Pro Ala Xaa Cys
65                  70                  75                  80

Arg Cys Thr Arg Ser Arg Pro Ala Leu Val Val Ser
                85                  90

<210> SEQ ID NO 46
<211> LENGTH: 18
<212> TYPE: DNA
<213> ORGANISM: Artificial Sequence
<220> FEATURE:
<223> OTHER INFORMATION: Oligonucleotides
```

```
<400> SEQUENCE: 46
cggcggatca gcatctac                                            18

<210> SEQ ID NO 47
<211> LENGTH: 20
<212> TYPE: DNA
<213> ORGANISM: Artificial Sequence
<220> FEATURE:
<223> OTHER INFORMATION: Oligonucleotides

<400> SEQUENCE: 47
cacctcatcg tggccaggtt                                          20

<210> SEQ ID NO 48
<211> LENGTH: 19
<212> TYPE: DNA
<213> ORGANISM: Artificial Sequence
<220> FEATURE:
<223> OTHER INFORMATION: Oligonucleotides

<400> SEQUENCE: 48
accgaacacg agtggagca                                           19

<210> SEQ ID NO 49
<211> LENGTH: 20
<212> TYPE: DNA
<213> ORGANISM: Artificial Sequence
<220> FEATURE:
<223> OTHER INFORMATION: Oligonucleotides

<400> SEQUENCE: 49
cagactctga ccgacgtcat                                          20

<210> SEQ ID NO 50
<211> LENGTH: 20
<212> TYPE: DNA
<213> ORGANISM: Artificial Sequence
<220> FEATURE:
<223> OTHER INFORMATION: Oligonucleotides

<400> SEQUENCE: 50
gcatttcggc tcccacggtg                                          20

<210> SEQ ID NO 51
<211> LENGTH: 20
<212> TYPE: DNA
<213> ORGANISM: Artificial Sequence
<220> FEATURE:
<223> OTHER INFORMATION: Oligonucleotides

<400> SEQUENCE: 51
tacgtcggtt cggcgcgcat                                          20

<210> SEQ ID NO 52
<211> LENGTH: 21
<212> TYPE: DNA
<213> ORGANISM: Artificial Sequence
<220> FEATURE:
<223> OTHER INFORMATION: Oligonucleotides

<400> SEQUENCE: 52
atgaacactt cttcctctct a                                        21

<210> SEQ ID NO 53
<211> LENGTH: 20
```

```
<212> TYPE: DNA
<213> ORGANISM: Artificial Sequence
<220> FEATURE:
<223> OTHER INFORMATION: Oligonucleotides

<400> SEQUENCE: 53
catatcgcgg tgatcctgac                                              20

<210> SEQ ID NO 54
<211> LENGTH: 20
<212> TYPE: DNA
<213> ORGANISM: Artificial Sequence
<220> FEATURE:
<223> OTHER INFORMATION: Oligonucleotides

<400> SEQUENCE: 54
atggccacca acgacgacca                                              20

<210> SEQ ID NO 55
<211> LENGTH: 20
<212> TYPE: DNA
<213> ORGANISM: Artificial Sequence
<220> FEATURE:
<223> OTHER INFORMATION: Oligonucleotides

<400> SEQUENCE: 55
cgcggccgtc gggccggctg                                              20

<210> SEQ ID NO 56
<211> LENGTH: 19
<212> TYPE: DNA
<213> ORGANISM: Artificial Sequence
<220> FEATURE:
<223> OTHER INFORMATION: Oligonucleotides

<400> SEQUENCE: 56
gcaggcgttt gcgttcttg                                               19

<210> SEQ ID NO 57
<211> LENGTH: 20
<212> TYPE: DNA
<213> ORGANISM: Artificial Sequence
<220> FEATURE:
<223> OTHER INFORMATION: Oligonucleotides

<400> SEQUENCE: 57
cgaggtccga aatagcgtag                                              20

<210> SEQ ID NO 58
<211> LENGTH: 20
<212> TYPE: DNA
<213> ORGANISM: Artificial Sequence
<220> FEATURE:
<223> OTHER INFORMATION: Oligonucleotides

<400> SEQUENCE: 58
atgcgtttcg ccctcccgac                                              20

<210> SEQ ID NO 59
<211> LENGTH: 20
<212> TYPE: DNA
<213> ORGANISM: Artificial Sequence
<220> FEATURE:
<223> OTHER INFORMATION: Oligonucleotides

<400> SEQUENCE: 59
```
tcacgccttg atttcgtcct                                              20

<210> SEQ ID NO 60
<211> LENGTH: 20
<212> TYPE: DNA
<213> ORGANISM: Artificial Sequence
<220> FEATURE:
<223> OTHER INFORMATION: Oligonucleotides

<400> SEQUENCE: 60
tggccgaacg cggactgttc                                              20

<210> SEQ ID NO 61
<211> LENGTH: 20
<212> TYPE: DNA
<213> ORGANISM: Artificial Sequence
<220> FEATURE:
<223> OTHER INFORMATION: Oligonucleotides

<400> SEQUENCE: 61
taggaatccg cgtcgacgat                                              20

<210> SEQ ID NO 62
<211> LENGTH: 20
<212> TYPE: DNA
<213> ORGANISM: Artificial Sequence
<220> FEATURE:
<223> OTHER INFORMATION: Oligonucleotides

<400> SEQUENCE: 62
caaggttcgt gacggtatcg                                              20

<210> SEQ ID NO 63
<211> LENGTH: 19
<212> TYPE: DNA
<213> ORGANISM: Artificial Sequence
<220> FEATURE:
<223> OTHER INFORMATION: Oligonucleotides

<400> SEQUENCE: 63
tgaccccagc aggtatggc                                               19

<210> SEQ ID NO 64
<211> LENGTH: 20
<212> TYPE: DNA
<213> ORGANISM: Artificial Sequence
<220> FEATURE:
<223> OTHER INFORMATION: Oligonucleotides

<400> SEQUENCE: 64
catctactga gcgccgtttg                                              20

<210> SEQ ID NO 65
<211> LENGTH: 20
<212> TYPE: DNA
<213> ORGANISM: Artificial Sequence
<220> FEATURE:
<223> OTHER INFORMATION: Oligonucleotides

<400> SEQUENCE: 65
cacgccgcca ccccgtcccg                                              20

<210> SEQ ID NO 66
<211> LENGTH: 18
<212> TYPE: DNA
<213> ORGANISM: Artificial Sequence

```
<220> FEATURE:
<223> OTHER INFORMATION: Oligonucleotides

<400> SEQUENCE: 66
gcaaggtggg ctttgaag                                                 18

<210> SEQ ID NO 67
<211> LENGTH: 18
<212> TYPE: DNA
<213> ORGANISM: Artificial Sequence
<220> FEATURE:
<223> OTHER INFORMATION: Oligonucleotides

<400> SEQUENCE: 67
tgcgtgggag gataaggc                                                 18

<210> SEQ ID NO 68
<211> LENGTH: 18
<212> TYPE: DNA
<213> ORGANISM: Artificial Sequence
<220> FEATURE:
<223> OTHER INFORMATION: Oligonucleotides

<400> SEQUENCE: 68
ttggcactgg cgtttatg                                                 18

<210> SEQ ID NO 69
<211> LENGTH: 20
<212> TYPE: DNA
<213> ORGANISM: Artificial Sequence
<220> FEATURE:
<223> OTHER INFORMATION: Oligonucleotides

<400> SEQUENCE: 69
acatcgggaa cacaggtctc                                               20

<210> SEQ ID NO 70
<211> LENGTH: 20
<212> TYPE: DNA
<213> ORGANISM: Artificial Sequence
<220> FEATURE:
<223> OTHER INFORMATION: Oligonucleotides

<400> SEQUENCE: 70
atcctccggt ttggcgggaa                                               20

<210> SEQ ID NO 71
<211> LENGTH: 19
<212> TYPE: DNA
<213> ORGANISM: Artificial Sequence
<220> FEATURE:
<223> OTHER INFORMATION: Oligonucleotides

<400> SEQUENCE: 71
acagaggtcg atcgggtcg                                                19

<210> SEQ ID NO 72
<211> LENGTH: 20
<212> TYPE: DNA
<213> ORGANISM: Artificial Sequence
<220> FEATURE:
<223> OTHER INFORMATION: Oligonucleotides

<400> SEQUENCE: 72
cagtcggccg gcgaaacgcc                                               20
```

<210> SEQ ID NO 73
<211> LENGTH: 18
<212> TYPE: DNA
<213> ORGANISM: Artificial Sequence
<220> FEATURE:
<223> OTHER INFORMATION: Oligonucleotides

<400> SEQUENCE: 73
cgcggcgaaa tcgaacgc                                                 18

<210> SEQ ID NO 74
<211> LENGTH: 20
<212> TYPE: DNA
<213> ORGANISM: Artificial Sequence
<220> FEATURE:
<223> OTHER INFORMATION: Oligonucleotides

<400> SEQUENCE: 74
cacgtgctgt ccccatcggc                                               20

<210> SEQ ID NO 75
<211> LENGTH: 20
<212> TYPE: DNA
<213> ORGANISM: Artificial Sequence
<220> FEATURE:
<223> OTHER INFORMATION: Oligonucleotides

<400> SEQUENCE: 75
ctacgtcttc gtgaccaaag                                               20

<210> SEQ ID NO 76
<211> LENGTH: 20
<212> TYPE: DNA
<213> ORGANISM: Artificial Sequence
<220> FEATURE:
<223> OTHER INFORMATION: Oligonucleotides

<400> SEQUENCE: 76
tgaccaccga caaccccacg                                               20

<210> SEQ ID NO 77
<211> LENGTH: 20
<212> TYPE: DNA
<213> ORGANISM: Artificial Sequence
<220> FEATURE:
<223> OTHER INFORMATION: Oligonucleotides

<400> SEQUENCE: 77
catgagggct gtccctctcc                                               20

<210> SEQ ID NO 78
<211> LENGTH: 20
<212> TYPE: DNA
<213> ORGANISM: Artificial Sequence
<220> FEATURE:
<223> OTHER INFORMATION: Oligonucleotides

<400> SEQUENCE: 78
ttgaccgcgt tgacggcgtt                                               20

<210> SEQ ID NO 79
<211> LENGTH: 20
<212> TYPE: DNA
<213> ORGANISM: Artificial Sequence
<220> FEATURE:
<223> OTHER INFORMATION: Oligonucleotides

<400> SEQUENCE: 79
cagcggtccg cgctcttcgc                                               20

<210> SEQ ID NO 80
<211> LENGTH: 19
<212> TYPE: DNA
<213> ORGANISM: Artificial Sequence
<220> FEATURE:
<223> OTHER INFORMATION: Oligonucleotides

<400> SEQUENCE: 80
tgggcagccc ggtgtcccg                                                19

<210> SEQ ID NO 81
<211> LENGTH: 20
<212> TYPE: DNA
<213> ORGANISM: Artificial Sequence
<220> FEATURE:
<223> OTHER INFORMATION: Oligonucleotides

<400> SEQUENCE: 81
cacgcgctcc tttcagcctt                                               20

<210> SEQ ID NO 82
<211> LENGTH: 20
<212> TYPE: DNA
<213> ORGANISM: Artificial Sequence
<220> FEATURE:
<223> OTHER INFORMATION: Oligonucleotides

<400> SEQUENCE: 82
cagtcacccc gcggccggta                                               20

<210> SEQ ID NO 83
<211> LENGTH: 21
<212> TYPE: DNA
<213> ORGANISM: Artificial Sequence
<220> FEATURE:
<223> OTHER INFORMATION: Oligonucleotides

<400> SEQUENCE: 83
tctactgacc cgcagatcga a                                             21

<210> SEQ ID NO 84
<211> LENGTH: 20
<212> TYPE: DNA
<213> ORGANISM: Artificial Sequence
<220> FEATURE:
<223> OTHER INFORMATION: Oligonucleotides

<400> SEQUENCE: 84
tggccgtcaa ggaccagaac                                               20

<210> SEQ ID NO 85
<211> LENGTH: 20
<212> TYPE: DNA
<213> ORGANISM: Artificial Sequence
<220> FEATURE:
<223> OTHER INFORMATION: Oligonucleotides

<400> SEQUENCE: 85
catgaccctg ccggcgtccc                                               20

<210> SEQ ID NO 86

```
<211> LENGTH: 20
<212> TYPE: DNA
<213> ORGANISM: Artificial Sequence
<220> FEATURE:
<223> OTHER INFORMATION: Oligonucleotides

<400> SEQUENCE: 86
tggcattgga tcgcgtcgga                                               20

<210> SEQ ID NO 87
<211> LENGTH: 20
<212> TYPE: DNA
<213> ORGANISM: Artificial Sequence
<220> FEATURE:
<223> OTHER INFORMATION: Oligonucleotides

<400> SEQUENCE: 87
tcaaacccgg cgagttcttc                                               20

<210> SEQ ID NO 88
<211> LENGTH: 21
<212> TYPE: DNA
<213> ORGANISM: Artificial Sequence
<220> FEATURE:
<223> OTHER INFORMATION: Oligonucleotides

<400> SEQUENCE: 88
atcaggctga cgggattgcc c                                             21

<210> SEQ ID NO 89
<211> LENGTH: 20
<212> TYPE: DNA
<213> ORGANISM: Artificial Sequence
<220> FEATURE:
<223> OTHER INFORMATION: Oligonucleotides

<400> SEQUENCE: 89
tcaacgagtg cacgggaacc                                               20

<210> SEQ ID NO 90
<211> LENGTH: 19
<212> TYPE: DNA
<213> ORGANISM: Artificial Sequence
<220> FEATURE:
<223> OTHER INFORMATION: Oligonucleotides

<400> SEQUENCE: 90
ttgctgcggg aaggttgcc                                                19

<210> SEQ ID NO 91
<211> LENGTH: 21
<212> TYPE: DNA
<213> ORGANISM: Artificial Sequence
<220> FEATURE:
<223> OTHER INFORMATION: Oligonucleotides

<400> SEQUENCE: 91
cgagaacgag atgtgcgtca g                                             21

<210> SEQ ID NO 92
<211> LENGTH: 19
<212> TYPE: DNA
<213> ORGANISM: Artificial Sequence
<220> FEATURE:
<223> OTHER INFORMATION: Oligonucleotides

<400> SEQUENCE: 92
```

-continued gcaggcgttt gcgttcttg                                            19

<210> SEQ ID NO 93
<211> LENGTH: 21
<212> TYPE: DNA
<213> ORGANISM: Artificial Sequence
<220> FEATURE:
<223> OTHER INFORMATION: Oligonucleotides

<400> SEQUENCE: 93
cgaggtccga aatagcgtag g                                         21

<210> SEQ ID NO 94
<211> LENGTH: 21
<212> TYPE: DNA
<213> ORGANISM: Artificial Sequence
<220> FEATURE:
<223> OTHER INFORMATION: Oligonucleotides

<400> SEQUENCE: 94
ccaaggttcg tgacggtatc g                                         21

<210> SEQ ID NO 95
<211> LENGTH: 19
<212> TYPE: DNA
<213> ORGANISM: Artificial Sequence
<220> FEATURE:
<223> OTHER INFORMATION: Oligonucleotides

<400> SEQUENCE: 95
tgaccccagc aggtatggc                                            19

<210> SEQ ID NO 96
<211> LENGTH: 18
<212> TYPE: DNA
<213> ORGANISM: Artificial Sequence
<220> FEATURE:
<223> OTHER INFORMATION: Oligonucleotides

<400> SEQUENCE: 96
gcaaggtggg ctttgaag                                             18

<210> SEQ ID NO 97
<211> LENGTH: 18
<212> TYPE: DNA
<213> ORGANISM: Artificial Sequence
<220> FEATURE:
<223> OTHER INFORMATION: Oligonucleotides

<400> SEQUENCE: 97
tgcgtgggag gataaggc                                             18

<210> SEQ ID NO 98
<211> LENGTH: 18
<212> TYPE: DNA
<213> ORGANISM: Artificial Sequence
<220> FEATURE:
<223> OTHER INFORMATION: Oligonucleotides

<400> SEQUENCE: 98
ttggcactgg cgtttatg                                             18

<210> SEQ ID NO 99
<211> LENGTH: 20
<212> TYPE: DNA

<213> ORGANISM: Artificial Sequence
<220> FEATURE:
<223> OTHER INFORMATION: Oligonucleotides

<400> SEQUENCE: 99
acatcgggaa cacaggtctc                                                    20

<210> SEQ ID NO 100
<211> LENGTH: 18
<212> TYPE: DNA
<213> ORGANISM: Artificial Sequence
<220> FEATURE:
<223> OTHER INFORMATION: Oligonucleotides

<400> SEQUENCE: 100
atgcctacgg ttcggtgc                                                      18

<210> SEQ ID NO 101
<211> LENGTH: 18
<212> TYPE: DNA
<213> ORGANISM: Artificial Sequence
<220> FEATURE:
<223> OTHER INFORMATION: Oligonucleotides

<400> SEQUENCE: 101
aagacagcgt cagccagc                                                      18

<210> SEQ ID NO 102
<211> LENGTH: 969
<212> TYPE: DNA
<213> ORGANISM: Artificial Sequence
<220> FEATURE:
<223> OTHER INFORMATION: 75% sequence identity to Gene 10

<400> SEQUENCE: 102
ctgcgcgcgc tcagcggggg acgcgggaac aggatctagt ggtcgtggtg ctttccctgg         60
gattcgctgg gcgactttct caccgtgcac aacggctaca gcaccttgac tgaagagcgg        120
aggggggcca ggcgcccatt ccagggcccc cactccgacg tcgccgacat tgtggaggcc        180
atcgcgggct cgttggtgca attcctgcgc acgacccttg ccttcctggt gctggcccgg        240
gatgcttccg gtcacctggt gggggagtac ctgcgcgtcg agcacggcgg catccggctc        300
ctgttcgacg accggatatt ggccgacacc gacaccctga tggtgttcgg gctggtcctt        360
ctccccgccg aagtcgtggc ccagccgggg cagaactcgg cgatcggagc cagggtggat        420
cgcgtgggct ccagcctgct cctcgcccgg cagcaggacg acgccggctc cgacgtcaag        480
cccgaccggg aggacgatta gctgcacctc gggcatcggc acgtcccccc gctacatcgg        540
ttatcggcct acacgggctc cctgttcaag gcgctggacc ttgccgtgcg catcacgtcg        600
gggctgcttc cggcgcccct ggccgccacc gctctgatgg ctcccctgag caggtttcgc        660
gtcctcgagg cggccgcggt cctgcacgtt gtctcgaccc tcaacattga ccggcaactc        720
ccccacttcg acctcacccg ccgggtaagg gacggcctag gggagctgcc cagcctacgg        780
gtggacgcgc gccggcccca tcgctatagc gagccggcca actgcgattt ctacgggtag        840
ttcaggatcc cgcggctccc cgtacgtggc gctgtcctcg agctggtcgt ctccacgatc        900
tacaggaggc tgatcggcag atccgacagt ttcagaatct cctagcactt cctgcccagg        960
atgaagtga                                                               969

<210> SEQ ID NO 103
<211> LENGTH: 969

<212> TYPE: DNA
<213> ORGANISM: Artificial Sequence
<220> FEATURE:
<223> OTHER INFORMATION: 80% sequence identity to Gene 10

<400> SEQUENCE: 103

```
ctgcccccgc actccggccg agggccgatc tgcatgtact ggacctcgag caatgcgtgg      60
gattcgcacc gcgagattct gacccaggtc aagcggttct gcaccttgac cgatgtgggc     120
agcgcggcgt cgccccgtta cgtggggggcc gagtgcgacg aggcgcactt tctgcacgcc    180
aacgccggca cgttgcagct ttaccagcgc tggacgctag ccttcctgga gcaggcgggc    240
gtaggaaccg gacaggaggt ggccgagttc gagcgcgtcc tgcaggccgg caacgggctg    300
gtgaacgtcg agccgataat gcccgtcacc gtcaccgtga tcgtgtacgg gctcgacgat    360
ctcggcgggg aagaggaggg ccaggccggg gacatctggg ccttccgtcc ctccctggaa    420
cccgtgggca cctcccctgca cctgggcccg ctccacgtcg tcgccggtac cgacgtcaag    480
gccctgcggg aggacgaaaa ccagcaccag ggcatcccc tcgagccggg gctacaaggg    540
attaccgcct actccggctc gcagatcaag gcgctcgtcg ttgccctccg ctacaggagg    600
cgcgtgcatc cgcccggggt ggccgggacg ggacagttgg cacggctgag ctgctatccc    660
cacctcgacg ggcccgggca ggtggacgtt gtcaggaccc tgaacattct ccggcatctc    720
ccccacttcg tgcacaccgc cccggtaacc gaccggcttc gcgtgcaggc caccgaaccc    780
gtcgtcccgc ccccgccgca tgccttaacc gtggccggca actgcgaaat catcgggttg    840
ttctgcatgc cggcgcaggc cgatcgaccc ggagagatcg tgctggtcgt ctccacctac    900
atcacgtcgc tcttcggggg gtgcgactgc cacagatact tcaggctcaa gctgcccacg    960
aagagctga                                                            969
```

<210> SEQ ID NO 104
<211> LENGTH: 969
<212> TYPE: DNA
<213> ORGANISM: Artificial Sequence
<220> FEATURE:
<223> OTHER INFORMATION: 85% sequence identity to Gene 10

<400> SEQUENCE: 104

```
ctgcgcccgc tcaccgcggg agggcggttc agcatctact ggaggtggag ctttccgtgg     60
gaaacgcagc gggacattct gaccgtggac aagcgctact gcaccttgac cgtagtgcgc    120
tgggcgggct ggccccgtta ccagggcccc gactgcgacg acgcccagtt tcagcagggg    180
atcgccgcca ccatggacct ttacctcccc tcgacccttg cgtaccaggt gctggccggc    240
gaaggaaccg gacaggaggt cgcggtgatc caccgcgtcg tccaggcccg ctaccgggtg    300
gtgatccacg tgcggaaatt ggccgactcc gacagcctga tcgtgttcgg cctgcaccaa    360
ctcgcggggg aacacgaggc cgtgcccggg gacatcacgg ccttccgagc ctggctcgaa    420
cgcgtgggca ccagccagct gctgccccg ctccacgagg tcggccgcag cgaccacatg    480
gcgcagcgcc aggtggaata cctgctccac ggcgatccgg tcctgcggcg gcatcaacgg    540
tttttccgcca agaccggctc gctgatcaag gggctcgacg ttcgcgtccg cttcagctgg    600
ggccagcatc cggccggggt gggcgcgacc ggacagatgg ctccgcagac ctccttttcgg   660
gacctggtcg cgcgccggct gcaggaccat gtcaccacgc tgatctttca ccggcttctg    720
ccgctctacg agcacaccgc cccgcaaacg gacggcctac gggtggtggg caccctacgc    780
ctcgacccgg gccggcgcca tcccattacc gtggcgggca agagcgaata caacgggttg    840
```

```
atgtggaagc cgccgctcgc cgtacgagcc ggagacatgg tgcacgtcca ctcgtccatc      900
ttcacgacgc agtgcggcgc gtccgacagc atcagaaact tctggcacat cccggccacg      960
atgaggtga                                                              969
```

<210> SEQ ID NO 105
<211> LENGTH: 968
<212> TYPE: DNA
<213> ORGANISM: Artificial Sequence
<220> FEATURE:
<223> OTHER INFORMATION: 90% sequence identity to Gene 10

<400> SEQUENCE: 105

```
gtgcggccgc actccggcgg acggcggttc agcttctact ggacgtgcag ctaaccgtgg       60
caatcgcagc gcgacattga gaccgtggac aaccgcatct cgaccatgac cgaagtgcgg      120
agggccgcct ggccgcgata cgagggcccc cactgggacg acgcccacta tctgcagcgc      180
atggccggca ccttcgagct attccaccgc tcgacgctag cgttcagga ggtggccggc       240 gaagcaacgg gtcagctggt ggcgctgttc caccgcgtcg accaggcccg cttccggctg      300
gtgatcgacc aggggatatt ggccgtcacc gtcaccctga tggtgttggg gctggtccat      360
ctggccgggg aagacgagcc cgagcccggc gtgatctcgg ccaaccgtgc ctggctcgaa      420
cccgagggca cctgccagct gcaggccccg caccaccacg tgggcggcac cgacgacttg      480
ggccagcggc aggtcgaatt cctgcacgac gggcatccgc tcgtgccggg gcaacatcgg      540
tttaccgcct agaccccgctc gctgatgaac gggctcgtcg ttcgcgtccg ctacaggtgg      600
ggcctccatc cgggccgggt ggccgcgtcc ggtcacatgg caccgctgag ctgctttcgg      660
gagctggacg cgcccgcgct gctggacgaa gtcacgacgc tcaactttca cccgcttctg      720
ccccactacg agctcacggc cccggtaagc gacgggctag gggtgcaggc cagccaacgc      780
ctcgacccgg cccgcccccca acctttacc gagccgggca acagcgtatt catcgcgttg      840
atctggaagc cgccgcacgg cgaacgtgcc ggtcacatcg tgctcctcga cacgaccaac      900
ttcacgaggc tgtacggcgg gtccgagagc cacagaaact ctggcactac ctggcgacga      960
tgaggtga                                                              968
```

<210> SEQ ID NO 106
<211> LENGTH: 969
<212> TYPE: DNA
<213> ORGANISM: Artificial Sequence
<220> FEATURE:
<223> OTHER INFORMATION: 95% sequence identity to Gene 10

<400> SEQUENCE: 106

```
ctgcgcccgc acaccggcgg acggcggatc agcatctact ggacgtggtg ctatccgtgg       60
gaatcgcacc gcgacattca gaccctggac aacccttct ccaccaagac cgaagtgcgc      120
agggcgccct ggccccgata cgaggggccc gacaggacg acgcccactt tctgcagggc      180
atggccggca ccttggagca tttgcaccgc tcgacgcttc cgttccagga gctggccggc      240
gaagcaaccg gtctgcaggt ggcggtgttg cagcgcgtcg accaggccgg ctaccgggtg      300
gtgatcgagg agcggatatt ggccgacacc cacaccctga tggtgttcgg gctggaccat      360
ctccccgggg aagacgaggc cgtgcccggg gagaactcgg ccatccgtgc gtggctggaa      420
cgcgagggca cctgcctgct gctggccccg caccacgacg tcgccggcac cgacgacatg      480
ggccagcggc aggtggaata ccagcaccac ggggatccgc tcgagccgcg gcaacaacgg      540
ttttccgcct acacgcgctc gctgatgaag cggctcgacg ttcccgtccg caacagctgg      600
```

```
ggcctgcatc cggcgcgggt ggccgcgacc ggtcagatgg caccgctgac ctgctatcgc    660
gtcctggacg cccccgggct gctggacgat ctcacgacgc tgaacattca cccgcatctg    720
ccgcactacg agcaccgc cccggaaagc gacgggctac gggtgctggc cacgcaacgg     780
gtcgacccgg cgcggcccca tcccttttacc gaggcgggca acagcgaata caacgcgttg   840
atctggatcc cgccgcacgc cgatcgagcc ggtgacatcg tggtcgtcga ctcgacgaac    900
ttcacgacgc tgttcggcgg gtccgacagc ctcagaaact tctggcacaa cctggccacg    960
atgaggtga                                                             969
```

<210> SEQ ID NO 107
<211> LENGTH: 969
<212> TYPE: DNA
<213> ORGANISM: Artificial Sequence
<220> FEATURE:
<223> OTHER INFORMATION: 99% sequence identity to Gene 10

<400> SEQUENCE: 107

```
ctgcgcccgc acaccggcgg acggcggatc agcatctact ggacgtggag ctatccgtgg    60
gaatcgcagc gcgacattca gaccctggac aaccgcttct ccaccatgac ggaagtgcgc   120
agggcggcct ggccccgata cgaggggccc gactgggacg acgcccactt tctgcagggc   180
atcgccggca ccttggagct tttccaccgc tcgacgcttg cgttccagga gctggccggc   240
gaagctaccg gtcagcaggt ggcggtgttc cagcgcgtcg accaggccgg ctaccggctg   300
gtgatcgaca gcggatatt ggccgacacc gacaccctga tggtgttcgg gcaggaccat    360
ctcgccgggg aagacgaggc cgagcccggg gagatctcgg ccatccgtgc ctggctggaa   420
cgcgagggca ccctgcctgct gctggccccg caccacgacg tcggcggcac cgacgacatg   480
gcccagcgcc aggtcgaata cctgcaccac ggggatccgc tcgtgccggg gcaacaacgg   540 tttccgcct acaccgctc gctgatgaag gggctcgacg ttcccgtccg caacaggtgg    600
ggcctgcatc cggcccgggt ggccgcgacc ggtcagatgg ctccgctgac ctgctttcgc    660
gacctggacg cgcccgggct gctggacgat gtcacgacgc tgaactttca cccgcatctg    720
ccgcactacg agctcaccgc cccggaaagc gacgggctac gggtgctggc cacccaaggc   780
gtcgacccgg ccggccca tcccttttacc gaggcgggca acagcgaatt caacgcgttg    840
atctgcatgc cgccgcacgc cgaacgagcc ggtgacatcg tgctcgtcga ctcgaccaac    900
ttcacgacgc tgttcggcgg gtccgacagc ctcagaaact tctggcacaa cctggccacg    960
atgaggtga                                                             969
```

<210> SEQ ID NO 108
<211> LENGTH: 25
<212> TYPE: DNA
<213> ORGANISM: Artificial Sequence
<220> FEATURE:
<223> OTHER INFORMATION: Oligonucleotides

<400> SEQUENCE: 108

```
aatcaactcc agcagcgcgg cctcg                                            25
```

<210> SEQ ID NO 109
<211> LENGTH: 24
<212> TYPE: DNA
<213> ORGANISM: Artificial Sequence
<220> FEATURE:
<223> OTHER INFORMATION: Oligonucleotides

```
<400> SEQUENCE: 109
ccgctaattg agagatgcga ttgg                                              24
```